(12) United States Patent
Yano et al.

(10) Patent No.: US 6,777,153 B2
(45) Date of Patent: Aug. 17, 2004

(54) POLYHYDROXYALKANOATE CONTAINING UNIT WITH THIENYL STRUCTURE IN THE SIDE CHAIN, PROCESS FOR ITS PRODUCTION, CHARGE CONTROL AGENT, TONER BINDER AND TONER WHICH CONTAIN THIS POLYHYDROXYALKANOATE, AND IMAGE-FORMING METHOD AND IMAGE-FORMING APPARATUS WHICH MAKE USE OF THE TONER

(75) Inventors: Tetsuya Yano, Kanagawa (JP); Etsuko Sugawa, Kanagawa (JP); Takeshi Imamura, Kanagawa (JP); Tsutomu Honma, Kanagawa (JP); Takashi Kenmoku, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 155 days.

(21) Appl. No.: 10/105,305

(22) Filed: Mar. 26, 2002

(65) Prior Publication Data

US 2003/0096182 A1 May 22, 2003

(30) Foreign Application Priority Data

Mar. 27, 2001 (JP) ......................................... 2001/090026
Apr. 27, 2001 (JP) ......................................... 2001/133551

(51) Int. Cl.$^7$ ........................... G03G 9/00; C08G 63/06; C12P 7/62
(52) U.S. Cl. ........................ 430/110; 528/361; 528/377; 528/380; 527/300; 525/437; 435/41; 435/117; 435/130; 435/135; 435/136; 435/146; 435/874; 435/877; 430/96; 430/97; 430/108; 430/109; 430/110; 430/127
(58) Field of Search ............................... 528/361, 377, 528/380; 527/300; 525/437; 435/41, 117, 130, 135, 136, 146, 874, 877; 430/96, 97, 108, 109, 110, 127

(56) References Cited

U.S. PATENT DOCUMENTS 4,393,167 A 7/1983 Holmes et al. ................ 525/64

(List continued on next page.)

FOREIGN PATENT DOCUMENTS

JP 60-108861 6/1985

(List continued on next page.)

OTHER PUBLICATIONS

K. Fritzsche et al., "An Unusual Bacterial Polyester with a Phenyl Pendant Group," 191 *Makromol. Chem.* 1957–1965 (1990).

(List continued on next page.)

*Primary Examiner*—Samuel A. Acquah
(74) *Attorney, Agent, or Firm*—Fitzpatrick Cella Harper & Scinto

(57) ABSTRACT

A polyhydroxyalkanoate characterized by having in the molecule a unit represented by Chemical Formula (1):

$$\underset{(1)}{\left(O-CH-CH_2-CO\right)}$$

with thienyl-S ring attached via CO—(CH$_2$)$_n$— to CH wherein n may assume any one integral value within the range of from 1 to 8.

Also disclosed are a process for producing the polyhydroxyalkanoate by the use of a microorganism having the ability to produce the polyhydroxyalkanoate and accumulate it in the bacterial body; a charge control agent, a toner binder and a toner which contain this polyhydroxyalkanoate; and an image-forming method and an image-forming apparatus which make use of the toner.

40 Claims, 10 Drawing Sheets

U.S. PATENT DOCUMENTS

| | | | |
|---|---|---|---|
| 4,442,189 A | 4/1984 | Lu et al. | 430/45 |
| 4,480,021 A | 10/1984 | Lu et al. | 430/106.6 |
| 4,795,690 A | 1/1989 | Shindo et al. | 430/109 |
| 4,876,331 A | 10/1989 | Doi | 528/361 |
| 4,925,765 A | 5/1990 | Madeleine | 430/110 |
| 5,004,664 A | 4/1991 | Fuller et al. | 430/106.6 |
| 5,200,332 A | 4/1993 | Yamane et al. | 435/135 |
| 5,292,860 A | 3/1994 | Shiotani et al. | 528/361 |
| 5,334,698 A | 8/1994 | Witholt et al. | 528/354 |
| 5,612,161 A | 3/1997 | Watanabe et al. | 430/110 |
| 5,667,927 A | 9/1997 | Kubota et al. | 430/109 |

FOREIGN PATENT DOCUMENTS

| | | |
|---|---|---|
| JP | 61-3149 | 1/1986 |
| JP | 63-38958 | 2/1988 |
| JP | 63-88564 | 4/1988 |
| JP | 5-49487 | 3/1993 |
| JP | 5-64591 | 3/1993 |
| JP | 5-214081 | 8/1993 |
| JP | 6-145311 | 5/1994 |
| JP | 6-284892 | 10/1994 |
| JP | 6-289644 | 10/1994 |
| JP | 7-48438 | 2/1995 |
| JP | 7-72658 | 3/1995 |
| JP | 7-265065 | 10/1995 |
| JP | 8-89264 | 4/1996 |
| JP | 8-179564 | 7/1996 |
| JP | 8-262796 | 10/1996 |
| JP | 2623684 | 4/1997 |
| JP | 9-191893 | 7/1997 |
| JP | 9-274335 | 10/1997 |
| JP | 9-281746 | 10/1997 |
| JP | 2807795 | 7/1998 |
| JP | 11-32789 | 2/1999 |
| JP | 2989175 | 10/1999 |
| JP | 2000-72865 | 3/2000 |

OTHER PUBLICATIONS

Won Ho Park et al., "Epoxidation of Bacterial Polyesters with Unsaturated Side Chains. I. Production and Epoxidation of Polyesters From 10–Undecanoic Acid," 31 *Macromol.* 1480–1486 (1998).

Won Ho Park et al., "Epoxidation of Bacterial Polyesters with Unsaturated Side Chains. II. Rate of Epoxidation and Polymer Properties," 36 *J. Polym. Sci.* 2381–2387 (1998).

Helmut Ritter et al., "Bacterial Production of Polyesters Bearing Phenoxy Groups in the Side Chain, 1 Poly(3–hydroxy–5–phenoxypentanoate–co–3–hydroxy–9–phenoxy–nonanoate) from *Pseudomonas oleovorans*," 195 *Macromol. Chem. Phys.* 1665–1672 (1994).

Y.B. Kim et al., "Preparation and Characterization of Poly(β–hydroxyalkanoates) Obtained from *Pseudomonas oleovorans* Grown with Mixtures of 5–Phenylvaleric Acid and n–Alkanoic Acids," 24 *Macromol.* 5256–5260 (1991).

Yasuo Takagi et al., "Biosynthesis of Polyhydroxyalkanoate with a Thiophenoxy Side Groups Obtained from *Pseudomonas putida*," 32 *Macromol.* 8315–8318 (1999).

Suzette M. Aróstegui et al., "Bacterial Polyesters Produced by *Pseudomonas oleovorans* Containing Nitrophenyl Groups," 32 *Macromol.* 2889–2895 (1999).

Joanne M. Curley et al., "Production of Poly(3–hydroxyalkanoates) Containing Aromatic Substituents by *Pseudomonas oleovorans*," 29 *Macromol.* 1762–1766 (1996).

Henry J. Vogel et al., "Acetylornithinase of *Escherichia coli*: Partial Purification and Some Properties," *J. Biol. Chem.* 97–108 (1956).

B.A. Ramsay et al., "Effect of Nitrogen Limitation on Long–Side–Chain Poly–β–Hdroxyalkanoate Synthesis by *Pseudomonas resinovarans*," 58(2) *Appl. Environ. Microbiol.* 744–746 (1992).

POLYHYDROXYALKANOATE CONTAINING UNIT WITH THIENYL STRUCTURE IN THE SIDE CHAIN, PROCESS FOR ITS PRODUCTION, CHARGE CONTROL AGENT, TONER BINDER AND TONER WHICH CONTAIN THIS POLYHYDROXYALKANOATE, AND IMAGE-FORMING METHOD AND IMAGE-FORMING APPARATUS WHICH MAKE USE OF THE TONER

BACKGROUND OF THE INVENTION

1. Field of the Invention

This invention relates to a novel polyhydroxyalkanoate (hereinafter simply "PHA"), and also relates to a process for producing the PHA, comprising the step of producing a PHA by the use of a microorganism having the ability to produce the PHA and accumulate it in the bacterial body.

This invention further relates to a charge control agent, a toner binder and a toner for developing electrostatic latent images, used in recording processes which utilize electrophotography, electrostatic recording, magnetic recording or the like, an image-forming method making use of the toner, and an image-forming apparatus therefor. More particularly, it relates to a charge control agent, a toner binder and a toner for developing electrostatic latent images, used in electrophotographic, electrostatic-recording and electrostatic-printing apparatus such as copying machines, printers and facsimile machines, an image-forming method making use of the toner, and an image-forming apparatus therefor. Still more particularly, it relates to a negatively charging charge control agent having higher safety to human bodies and environment, a toner binder and a toner for developing electrostatic latent images, making use of such a charge control agent, an image-forming method making use of the toner, and an image-forming apparatus therefor.

2. Related Background Art

It has hitherto been reported that many microorganisms produce poly-3-hydroxybutyric acid (PHB) or other PHA and accumulate it in the bacterial body ("Handbook of Biodegradable Plastics", Biodegradable-Plastic Institute, K.K. N-T-S, pp.178–197, 1995). Like conventional plastics, these polymers can be utilized for the production of various products by melt processing or the like. Also, since they are biodegradable, they have an advantage of being completely broken down by microorganisms in the natural world, and by no means remain in natural environment to cause pollution as many conventional synthetic polymeric compounds do. They also have superior adaptability to living bodies and are expected to be applicable as medical flexible members.

It is known that such PHAs produced by microorganisms may have various composition and structure depending on the type of microorganisms used for its production, the composition of culture medium, the conditions for culturing and so forth. Researches on how to control such composition and structure have hitherto chiefly been made from the viewpoint of the improvement in physical properties of PHAs.

(1) In the first place, as biosyntheses of PHAs by the polymerization of a monomer unit having a relatively simple structure, including 3-hydroxybutyric acid (hereinafter simply "3HB"), the following cases are available.

(a) Those which contain 3HB and 3-hydroxyvaleric acid (hereinafter "3HV"):
U.S. Pat. Nos. 4,393,167, 4,876,331 and 5,200,332.

(b) those which contain 3HB and 3-hydroxyhexanoic acid (hereinafter "3HHx"):
U.S. Pat. No. 5,292,860 and Japanese Patent Application Laid-Open No. 7-265065.

(c) those which contain 3HB and 4-hydroxybutyric acid (hereinafter "4HB"):
Japanese Patent Application Laid-Open No. 9-191893.

(d) those which contain 3-hydroxyalkanoates having 6 to 12 carbon atoms:
U.S. Pat. No. 5,334,698.

(e) Biosynthesis utilizing a simple fatty acid as a carbon source. Products are substantially the same as those of (d); Appl. Environ. Microbiol., 58(2), 746, 1992.

These are all PHAs each comprised of a monomer unit having an alkyl group in the side chain, i.e., "usual PHA", all synthesized by β-oxidation of hydrocarbons or synthesis of fatty acids from saccharides by the microorganisms.

(2) When, however, broader application of such PHAs produced by microorganisms, e.g., application as functional polymers is taken into account, a PHA in which a substituent other than the alkyl group has been introduced in the side chain, i.e., "unusual PHA" is expected to be very useful. As examples of such a substituent, it may include those containing aromatic rings (such as a phenyl group and a phenoxy group), unsaturated hydrocarbons, an ester group, an ally group, a cyano group, halogenated hydrocarbons and epoxides. Of these, researches are energetically made especially on PHAs having aromatic rings.

(a) Those which contain a phenyl group or a partially substituted phenyl group:
Macromol. Chem. Phys., 191, 1957–1965 (1990) and Macromolecules, 24, 5256–5260 (1991) report that *Pseudomonas oleovorans* produces a PHA containing 3-hydroxy-5-phenylvaleric acid as a unit, using 5-phenylvaleric acid as a substrate.

Macromolecules, 29, 1762–1766 (1996) reports that *Pseudomonas oleovorans* produces a PHA containing 3-hydroxy-5-(4'-tolyl)valeric acid as a unit, using 5-(4'-toyl) valeric acid as a substrate.

Macromolecules, 32, 2889–2895 (1999) reports that *Pseudomonas oleovorans* produces a PHA containing 3-hydroxy-5-(2',4'-dinitrophenyl)valeric acid and 3-hydroxy-5-(4'-nitrophenyl)valeric acid as units, using 5-(2',4'-dinitrophenyl)valeric acid as a substrate.

(b) Those which contain a phenoxyl group or a partially substituted phenoxyl group:
Macromol. Chem. Phys., 195, 1665–1672 (1994) reports that *Pseudomonas oleovorans* produces a PHA copolymer of 3-hydroxy-5-phenoxyvaleric acid with 3-hydroxy-9-phenoxynonanoic acid, using 11-phenoxyundecanoic acid as a substrate.

Japanese Patent No. 2,989,175 discloses invention which is concerned with a homopolymer comprised of a 3-hydroxy-5-(monofluorophenoxy)pentanoate (3H5(MFP) P) unit or a 3-hydroxy-5-(difluorophenoxy)pentanoate (3H5 (DFP)P) unit, and a copolymer containing at least the (3H5(MFP)P) unit or the (3H5(DFP)P) unit; *Pseudomonas putida* capable of synthesizing such a polymer; and a process of producing the above polymer by the use of the genus Pseudomonas. It is reported that as its effect a polymer the side-chain terminal of which has a phenoxyl group substituted with 1 or 2 fluorine atom(s) can be synthesized by utilizing a long-chain fatty acid having a substituent and that stereo-regularity (syndiotacticity) and water repellency can be imparted having a high melting point and retaining good processability.

In addition to such fluorine-group-substituted products, cyano-group- or nitro-group-substituted products are also on researches.

Can. J. Microbiol., 41, 32–43 (1995) and Polymer International, 39, 205–213 (1996) report that a PHA containing 3-hydroxy-p-cyanophenoxyhexanoic acid or 3-hydroxy-p-nitrophenoxyhexanoic acid as a monomer unit is produced using octanoic acid and p-cyanophenoxyhexanoic acid or p-nitrophenoxyhexanoic acid as a substrate by the use of *Pseudomonas oleovorans* strain ATCC 29347 and *Pseudomonas putida* strain KT 2442.

These reports are useful in order to obtain polymers which all have an aromatic ring in the side chain of PHA, different from the commonly available PHAs having an alkyl group in the side chain, and have physical properties arising therefrom.

(3) As a new category, without limitation merely to changes in physical properties, researches are also made intending to produce a PHA having a suitable functional group in the side chain.

For example, Macromolecules, 31, 1480–1486 (1996) and Journal of Polymer Science: Part A: Polymer Chemistry, 36, 2381–2387 (1998) report that a PHA containing at the side-chain terminal a unit having a vinyl group is synthesized and thereafter the product synthesized is epoxidized with an oxidizing agent and this has enabled synthesis of a PHA containing a highly reactive epoxy group at the side-chain terminal.

Besides the vinyl group, as an example of synthesizing a PHA containing a unit having a thioether (—S—; a sulfanyl linkage), expected to provide a high reactivity, Macromolecules, 32, 8315–8318 (1999) reports that *Pseudomonas putida* strain 27N01 produces a PHA copolymer of 3-hydroxy-5-thiophenoxyvaleric acid (3-hydroxy-5-(phenylsulfanyl)valeric acid) with 3-hydroxy-7-thiophenoxyheptanoic acid (3-hydroxy-7-(phenylsulfanyl) heptanoic acid), using 11-thiophenoxyundecanoic acid (11-(phenylsulfanyl)undecanoic acid) as a substrate.

A number of methods are also conventionally known as methods for electrophotography. In general, copied images are obtained by forming an electrostatic latent image on an image-bearing member (photosensitive member) by utilizing a photoconductive material and by various means, subsequently developing the latent image by the use of a toner to form a visible image (toner image), transferring the toner image to a transfer medium as occasion calls, and then fixing the toner image to the transfer medium by heating and/or pressing. As methods by which the electrostatic latent image is formed into a visible image, cascade development, magnetic brush development, pressure development and so forth are known in the art. Another method is also known in which, using a magnetic toner and a rotary developing sleeve provided with magnetic poles at the core, the magnetic toner is caused to fly from the developing sleeve to the photosensitive member by the an electric field.

As development methods used when electrostatic latent images are developed, available are a two-component development method making use of a two-component type developer comprised of a toner and a carrier and a one-component development method making use of no carrier and comprised only of a toner.

Here, fine colored particles commonly called a toner are constituted of a binder resin and a colorant as essential components and besides optionally a magnetic material and so forth. As methods for imparting electric charges to the toner, the charging properties of the binder resin itself may be utilized without use of any charge control agent. If that is the case, however, the binder resin has poor charging stability with time and poor moisture resistance. Accordingly, a charge control agent is usually added for the purpose of charge retention and charge control of the toner.

Conventional charge control agents nowadays known in the present technical field include, e.g., as negative charge control agents, azo dye metal complexes, metal complexes of aromatic dicarboxylic acids and metal complexes of salicylic acid derivatives. Also, known as positive charge control agents are Nigrosine dyes, triphenylmethane dyes, organotin compounds such as quaternary ammonium salt dibutyltin oxides of various types, and so forth. Toners containing any of these as charge control agents, however, do not necessarily well satisfy quality characteristics such as charging performance and stability with time in some cases, depending on their composition; the characteristics being required in toners.

For example, toners containing the azo dye metal complexes known as negative charge control agents are on a reasonable level in respect of the highness of charge quantity. However, since the azo dye metal complexes are crystal compounds with a low molecular weight, they may have a poor dispersibility depending on the type of binder resins in which they are to be incorporated. In such as case, the negative charge control agents are not uniformly distributed in the binder resins, and the resultant toners also have a charge quantity distribution lacking in sharpness greatly, so that the images to be obtained may have a low gradation, showing a poor image formation performance. Moreover, the azo dye metal complexes have color tone specific thereto, and hence, under the existing conditions, they are used only in toners with hues limited mainly to black. When such toners are used as color toners, what is of a great problem is that they have not any sharpness of coloring agents which is required in order to obtain images having a high requirement for color tone.

As an example of nearly colorless negative charge control agents, the metal complexes of aromatic dicarboxylic acids are available, which, however, may have a problem of low dispersibility because of the fact that they are not perfectly colorless and that they are crystal compounds with a low molecular weight.

As for the Nigrosine dyes and the triphenylmethane dyes, known as positive charge control agents, they stand colored in themselves, and hence, under the existing conditions, they are also used only in toners with hues limited mainly to black, and also may have no good stability with time when such toners are used in continuous copying. Conventional quaternary ammonium salts may also have an insufficient moisture resistance when incorporated in toners. In such a case, such toners may have so poor a stability with time as not to afford any good images in their repeated use.

In recent years, from the viewpoint of environmental conservation, too, what has become a worldwide subject of discussion is how waste be curtailed and how the safety of waste be improved. Such a subject is likewise discussed also in the field of electrophotography. More specifically, with wide spread of image-forming apparatus, the disposal of printed paper, waste toner after use and copying paper is increasing year by year, and the safety of such waste is also an important subject from the standpoint of the conservation of global environment.

Taking account of such a point, studies are being made on polymer type charge control agents. They include compounds disclosed in, e.g., U.S. Pat. Nos. 4,480,021, 4,442,189 and 4,925,765 and Japanese Patent Application Laid-Open Nos. 60-108861, 61-3149, 63-38958 and 63-88564. Also, in general, as polymer type charge control agents used when toners are made to exhibit negative chargeability, there are many examples in which copolymers of styrene and/or α-methylstyrene with alkyl acrylates or methacrylates or alkyl acrylate or methacrylate amides having sulfonic acid groups are used (Japanese Patent Application Laid-Open Nos. 7-72658 and 8-179564 and Japanese Patent Nos. 2,114,410, 2,623,684 and 2,807,795). Such materials are advantageous in that they are colorless, but must be added in a large quantity in order to ensure charge quantity.

Thus, these compounds do not have any sufficient performance as charge control agents, and have problems on charge quantity, charging-rise performance, stability with time, environmental stability and so forth. Also, considering not only the aspect of function but also any influence on human bodies and environment, it is strongly sought in respect of compounds and organic solvents used in synthesis, too, to provide a safer compound, a safer and milder synthesis process, and a charge control agent which can achieve use of organic solvents in a smaller quantity.

From the viewpoint of environmental conservation, development is being made on resins degradable with time by the action of microorganisms, i.e., biodegradable resins. For example, as stated previously, it has been reported that many microorganisms are capable of producing the biodegradable resin PHA and accumulating it in the bacterial body. It is known that such PHA can have various composition and structure depending on the type of microorganisms used for its production, the composition of culture medium, the conditions for culturing and so forth. Researches on how to control such composition and structure have hitherto chiefly been made from the viewpoint of the improvement in physical properties of PHA. With regard to its application, too, they have already given reasonable actual results especially in the field of materials for medical use. In the field of agriculture, too, the biodegradable resins are used in multifiles, gardening material and so forth, and also in sustained-release agricultural chemicals, fertilizers and so forth. In the field of leisure industry, too, the biodegradable resins are used in fishing lines, fishing articles, golf goods and so forth.

However, considering their wide application as plastics, under the existing conditions they can not still be said to be satisfactory in respect of physical properties. In order to make the PHA utilizable in much wider ranges, it is important to study the improvement of physical properties more widely. For that end, it is essential to make development and research on PHAs containing monomer units of various structures. Meanwhile, the PHA of the type a substituent has been introduced in the side chain can be expected to be expanded as a "functional polymer" having very useful functions and properties attributable to the properties of the substituent introduced, by selecting according to the desired properties and so forth the substituent to be introduced. Namely, it is also an important subject to make development and research on such a superior PHA that can achieve both such functional factors and the biodegradability.

In the field of electrophotography, too, the application of biodegradable resins to binder resins is proposed especially in the production of toners. For example, U.S. Pat. No. 5,004,664 discloses a toner having as its composition a biodegradable resin, in particular, polyhydroxybutyric acid, polyhydroxyvaleric acid, or a copolymer or blend of these. Japanese Patent Application Laid-Open No. 6-289644 also discloses an electrophotographic toner particularly used for heat-roll fixing, which is characterized in that at least a binder resin contains a vegetable wax and a biodegradable resin (as exemplified by polyesters produced by microorganisms and natural polymeric materials derived from vegetables or animals), and the vegetable wax is added to the binder resin in an amount of from 5 to 50% by weight.

U.S. Pat. No. 5,667,927 also discloses an electrophotographic toner characterized by containing a lactic-acid resin as a binder resin. Japanese Patent Application Laid-Open No. 9-274335 still also discloses a toner for developing electrostatic latent images which is characterized by containing a polyester resin and a colorant; the former being obtained by dehydration polycondensation of a composition containing lactic acid and a tri- or more functional oxycarboxylic acid.

Japanese Patent Application Laid-Open No. 8-262796 also discloses an electrophotographic toner containing a binder resin and a colorant, and is characterized in that the binder resin comprises a biodegradable resin (as exemplified by aliphatic polyester resins) and the colorant comprises a water-insoluble coloring matter. Japanese Patent Application Laid-Open No. 9-281746 still also discloses a toner for developing electrostatic latent images which is characterized by containing a urethanated polyester resin and a colorant; the former being obtained by cross-linking polylactic acid with a tri- or more functional polybasic isocyanate.

In all the electrophotographic toners stated above, biodegradable resins are used as their binder resins, and they are understood to have the effect of contributing to the environmental safeguard and so forth.

However, any report on an example in which biodegradable resins are used in charge control agents is still unknown. Thus, there is room for further progress in respect of the contribution to the environmental safeguard and so forth.

As stated previously, in the PHAs produced by microorganisms, those having various composition and structure are obtained by changing the type of microorganisms used for its production, the composition of culture medium, the conditions for culturing and so forth. However, considering their wide application as plastics, they can not still be said to be satisfactory in respect of physical properties. In order to make the PHA utilizable in much wider ranges, it is important to study the improvement of physical properties more widely. For that end, it is essential to make development and research on PHAs containing monomer units of various structures, on their production processes and on microorganisms capable of producing the desired PHAs efficiently.

Meanwhile, as also stated previously, the PHA of the type a substituent has been introduced in the side chain (the unusual PHA) can be expected to be expanded as a "functional polymer" having very useful functions and properties attributable to the properties of the substituent introduced, by selecting according to the desired properties and so forth the substituent to be introduced. Thus, it is also an important subject to make development and research on such a superior PHA that can achieve both the functional factors and the biodegradability, on its production process and on microorganisms capable of producing the desired PHA efficiently.

More specifically, where PHAs in the side chains of which various substituents have been introduced are produced by microorganisms, a method is used in which, as is seen in the reports given previously on *Pseudomonas oleovorans*, an alkanoate having a substituent intended to be introduced is utilized also as a carbon source for proliferation in addition to its utilization as a raw material for polymers.

However, in the method in which an alkanoate having a substituent intended to be introduced is utilized also as a carbon source for proliferation in addition to its utilization as a raw material for polymers, it is expected that an energy source on the basis of the formation of acetyl-CoA by β-oxidation is supplied from the alkanoate. In such a method, the acetyl-CoA can not be formed by β-oxidation unless the substrate has a chain length which is large to a certain extent. Hence, it is of a great problem that the alkanoate usable as the substrate of PHA is necessarily limited. Also, commonly, substrates whose chain length has come short for two methylene chains each as a result of β-oxidation are newly formed, and these are incorporated as monomer units of the PHA. Hence, the PHA synthesized may often be a copolymer comprised of monomer units whose chain length differs for two methylene chains each. In the reports given previously, produced is a copolymer comprised of three monomer units, 3-hydroxy-8-phenoxyoctanoic acid derived from 8-phenoxyoctanoic acid which is a substrate, 3-hydroxy-6-phenoxyhexanoic acid which is a by-product derived from a metabolic intermediate and 3-hydroxy-4-phenoxybutyric acid. In this regard, it is very difficult to use this method when it is intended to obtain a PHA comprised of single monomer units. Moreover, in the method which conditions that an energy source on the basis of the formation of acetyl-CoA by β-oxidation is supplied, microorganisms may proliferate so slowly that it takes a time to synthesize the PHA and that the PHA synthesized tends to be in a low yield. These are also of great problems.

Accordingly, it is considered effective to use a method in which microorganisms are cultured in a culture medium where, in place of the alkanoate having a substituent to be introduced, a medium-chain fatty acid or the like such as octanoic acid or nonanoic acid is made present together (coexistent) as a carbon source for proliferation, and thereafter the PHA is extracted. Such a method is commonly used.

However, according to studies made by the present inventors, the PHA synthesized through β-oxidation, using the medium-chain fatty acid or the like such as octanoic acid or nonanoic acid as the carbon source for proliferation as in the above may be obtained in a low purity, and 50% or more of the polymer obtained is held by 3-hydroxyalkanoic acid monomer units of mcl (hereinafter often simply "mcl-3HA"), i.e., the units of "usual PHA", which are monomer units derived from the carbon source for proliferation (e.g., 3-hydroxyoctanoic acid and 3-hydroxynonanoic acid). These mcl-3HA monomer units are polymers which are tacky at normal temperature when composed alone, and may make polymers have a greatly low glass transition temperature (Tg) when mixedly present in a large quantity in the PHA intended in the present invention. Hence, where physical properties of polymers which are hard at normal temperature are to be attained, it is not preferable that the mcl-3HA monomer units are mixedly present.

It is also known that such heterogeneous side-chain structure may obstruct the intramolecular or intermolecular mutual action attributable to the side-chain structure to greatly affect crystallizability or orientationality. For the achievement of improvement in physical properties of polymers and impartment of functional performance thereto, it is of a great problem that such mcl-3HA monomer units are mixedly present. As a means for solving this problem, a purification step for separating and removing any "unintended" monomer units such as the mcl-3HA monomer units derived from the carbon source for proliferation may be provided in order to obtain a PHA constituted of only monomer units having specific substituents. This, however, brings about problems that its operation is complicated and also a greatly low yield may inevitably result. A greater problem is that, where the intended monomer units and the unintended monomer units have formed a polymer, it is very difficult to remove only the unintended monomer units. Especially where it is intended to synthesize a PHA containing such monomer units that have as side-chain structure a group obtained from an unsaturated hydrocarbon, an ester group, an allyl group, a cyano group, a nitro group, a group obtained from a halogenated hydrocarbon or a group into which an epoxide has been introduced, the mcl-3HA monomer units often form a copolymer together with the intended monomer units. Thus, it is very difficult to remove the mcl-3HA monomer units after the synthesis of PHA.

Accordingly, the present inventors have come acknowledged that, when the application to functional polymers is taken into account, it is by all means necessary to make development of a biosynthetic process by which the "unusual PHA" can be obtained in a high purity. Thus, it has been considered very useful and important to make development of i) a superior polymer having both the functional performance and the biodegradability as stated above, ii) microorganisms capable of producing such a polymer and accumulating it in the bacterial body, and iii) a process for bio-synthesizing the PHA in a high purity and efficiently.

SUMMARY OF THE INVENTION

The present invention is to solve the problems discussed above, and an object of the present invention is to provide a PHA (unusual PHA) containing a monomer unit having a variety of structure, having in the side chain a substituent, which PHA is useful as device materials and medical materials, and provide a process for producing the unusual PHA by utilizing microorganisms, in particular, a process which can obtain the intended "unusual PHA" in a high purity with less unintended monomer units mixedly present and can promise a high yield.

As a PHA having a suitable functional group in the side chain and expected to have new function attributable to such a functional group, it is foreseen that, in order to make development of functional PHAs, a PHA having an S atom in the side chain for example will be on research more and more in future because of its highness of reactivity. However, examples of research on such a PHA are very few. Only a report concerning a PHA containing a 3-hydroxyphenylsulfanylalkanoic acid unit can be exemplified as a related report.

In order to make development of functional PHAs by chemically modifying the side chain of the PHA obtained, it is desired for the PHA to have a side chain such as a thienyl group or a thienoyl group, having a higher reactivity than a phenyl group. However, there has been no report that any PHA concerned with it has been produced.

Taking account of such a subject, another object of the present invention is to provide a novel PHA containing a unit having a thienyl structure in the side chain, and a process for its production.

A further object of the present invention is, in order to solve the above problems in electrophotographic processes, to provide a negatively charging charge control agent which is more highly contributory to the environmental safeguard and so forth from the aspect of function and also has high performances (i.e., high charge quantity, quick rise in charging, good stability with time and high environmental stability), and has been improved in dispersibility, utilizing the novel PHA containing a unit having a thienyl structure in the side chain; and a toner binder comprising such a charge control agent, a toner for developing electrostatic latent images which comprises the charge control agent, and an image-forming method and an image-forming apparatus which make use of the toner for developing electrostatic latent images Accordingly, aiming at the development of a PHA having in the side chain a functional group, which is useful as device materials and medical materials, the present inventors have repeatedly made investigation of microorganisms having the ability to produce various PHAs and accumulate them in the bacterial body, and extensive researches on a process for producing the desired PHA by using such microorganisms. As a result, they have accomplished the invention as described below. That is, the summary of the present invention is as follows:

The present invention provides a polyhydroxyalkanoate characterized by having in the molecule a unit represented by Chemical Formula (1):

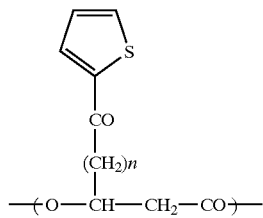

wherein n may assume any one integral value within the range of from 1 to 8.

The present invention is also a process for producing a polyhydroxyalkanoate having in the molecule the unit represented by Chemical Formula (1); the process comprising culturing a microorganism in a culture medium containing at least one compound represented by Chemical Formula (7) or (8):

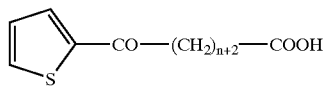

wherein n may assume any one integral value within the range of from 1 to 8,

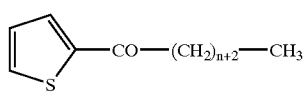

wherein n may assume any one integral value within the range of from 1 to 8, and polypeptone.

The present invention is still also a process for producing a polyhydroxyalkanoate having in the molecule the unit represented by Chemical Formula (1); the process comprising culturing a microorganism in a culture medium containing at least one compound represented by Chemical Formula (7) or (8) and yeast extract.

The present invention is further a process for producing a polyhydroxyalkanoate having in the molecule the unit represented by Chemical Formula (1); the process comprising culturing a microorganism in a culture medium containing at least one compound represented by Chemical Formula (7) or (8) and a saccharide.

The present invention is still further a process for producing a polyhydroxyalkanoate having in the molecule the unit represented by Chemical Formula (1); the process comprising culturing a microorganism in a culture medium containing at least one compound represented by Chemical Formula (7) or (8) and an organic acid or a salt thereof.

The present invention is still further a process for producing a polyhydroxyalkanoate having in the molecule the unit represented by Chemical Formula (1); the process comprising culturing a microorganism in a culture medium containing at least one compound represented by Chemical Formula (7) or (8) and an amino acid or a salt thereof.

The present invention is still further a process for producing a polyhydroxyalkanoate having in the molecule the unit represented by Chemical Formula (1); the process comprising culturing a microorganism in a culture medium containing at least one compound represented by Chemical Formula (7) or (8) and a straight-chain alkanoic acid having 4 to 12 carbon atoms or a salt thereof.

The present inventors have made further extensive studies aiming at the development of a charge control agent which is more highly contributory to the environmental safeguard and so forth and also has high performances. As a result, they have accomplished the present invention.

That is, the present invention is a charge control agent comprising a polyhydroxyalkanoate having in the molecule at least one unit of units represented by Chemical Formula (1):

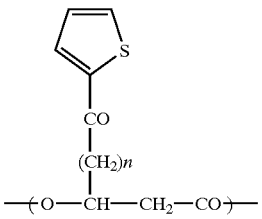

wherein n may assume any one integral value within the range of from 1 to 8.

The present invention is also a charge control agent comprising a polyhydroxyalkanoate having in the molecule at least one unit of units represented by Chemical Formula (12):

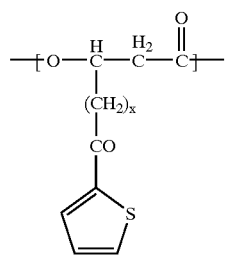

x=1–8 wherein n may assume any one integral value within the range of from 1 to 8.

The present invention is still also a toner binder comprising a charge control agent having the above polyhydroxyalkanoate.

The present invention is further a toner for developing electrostatic latent images which comprises a binder resin, a colorant and a charge control agent having the above polyhydroxyalkanoate.

The present invention is still further an image-forming method comprising:

a charging step of applying a voltage to a charging member from its outside to charge an electrostatic-latent-image-bearing member electrostatically;

a latent-image-forming step of forming an electrostatic latent image on the electrostatic-latent-image-bearing member thus charged;

a developing step of developing the electrostatic latent image by the use of a toner for developing electrostatic latent images, to form a toner image on the electrostatic-latent-image-bearing member;

a transfer step of transferring to a recording medium the toner image formed on the electrostatic-latent-image-bearing member; and a heat fixing step of fixing by heat the toner image held on the recording medium;

wherein the toner for developing electrostatic latent images comprises a binder resin, a colorant and a charge control agent containing the above polyhydroxyalkanoate.

The present invention is still further an image-forming apparatus comprising:

a charging means for applying a voltage to a charging member from its outside to charge an electrostatic-latent-image-bearing member electrostatically;

a latent-image-forming means for forming an electrostatic latent image on the electrostatic-latent-image-bearing member thus charged;

a developing means for developing the electrostatic latent image by the use of a toner for developing electrostatic latent images, to form a toner image on the electrostatic-latent-image-bearing member;

a transfer means for transferring to a recording medium the toner image formed on the electrostatic-latent-image-bearing member; and a heat fixing means for fixing by heat the toner image held on the recording medium;

wherein the toner for developing electrostatic latent images comprises a binder resin, a colorant and a charge control agent containing the above polyhydroxyalkanoate.

DETAILED DESCRIPTION OF THE INVENTION

Figure 1:
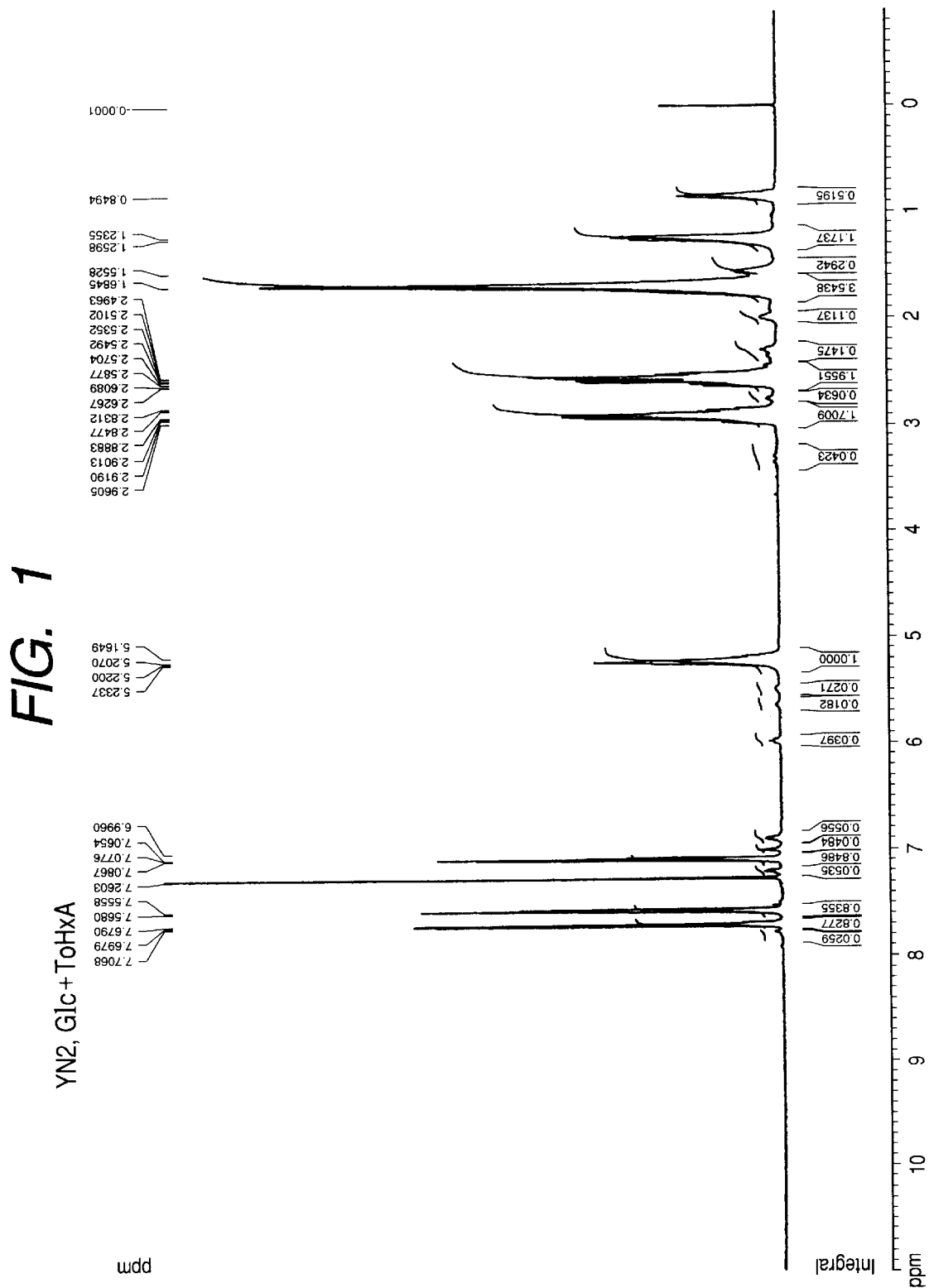
FIG. 1 is a chart showing a $^1$H-NMR spectrum of a polymer in Example 1.

The PHA of the present invention is a PHA having a monomer unit with a variety of structure, having in the side chain a substituent, which PHA is useful as device materials, medical materials and so forth. More specifically, it is a PHA having a thienyl structure in the side chain. The process for producing the PHA according to the present invention also enables production of the desired PHA in a high purity and a high yield by utilizing a microorganism. Also, the PHA of the present invention is an isotactic polymer, which is commonly constituted of only the R-configuration.

Saccharide, And Organic Acid Participating in TCA Cycle; Difference From Prior Art One of PHA production processes of the present invention is characterized in that, when the microorganism is cultured, in addition to alkanoic acid or alkane for introducing the desired monomer unit, a saccharide or an organic acid participating in the TCA cycle is added to a culture medium as a carbon source other than the alkanoic acid or alkane so that the PHA the microorganism produces and accumulates can have the intended monomer unit in a very high content or have only the intended monomer unit. The effect of promoting the predominant occupation by this specific monomer unit is attained by adding to the culture medium only the saccharide or the organic acid participating in the TCA cycle, as the carbon source other than the alkanoic acid or alkane.

More specifically, the present inventors have discovered that, when microorganisms are cultured by the use of the saccharide or the organic acid participating in the TCA cycle as a coexistent substrate together with the alkanoic acid or alkane for introducing the desired monomer unit, the intended PHA can be obtained in a markedly superior yield and purity compared with any conventional methods making use of mcl-alkanoic acid or alkane such as nonanoic acid or octanoic acid as a coexistent substrate, and that such an effect can be obtained because of a culturing process by which the acetyl-CoA which is the carbon source and energy source of the microorganism is produced by a method not relying on the β-oxidation. Thus, they have accomplished the present invention.

In the process of the present invention, saccharide compounds as exemplified by glucose, fructose and mannose come to be utilized as substrates for proliferation of microorganism. The PHA produced is constituted of the alkanoic acid or alkane for introducing the desired monomer unit, which is made coexistent with the saccharide, where monomer units derived from saccharides such as glucose are not contained at all or are contained only in a very small quantity. On account of such a feature, the process of the present invention differs fundamentally in both construction and effect from any conventional processes of producing PHAs by microorganisms; the processes making use of saccharides themselves such as glucose as raw-material substrates of monomer units to be introduced into the PHAs.

Yeast Extract; Difference From Prior Art

One of PHA production processes of the present invention is characterized in that, when the microorganism is cultured, in addition to alkanoic acid or alkane for introducing the desired monomer unit, only yeast extract is added to a culture medium as a carbon source other than the alkanoic acid or alkane so that the PHA the microorganism produces and accumulates can have the intended monomer unit in a very high content or have only the intended monomer unit. The effect of promoting the predominant occupation by this specific monomer unit is attained by adding to the culture medium only the yeast extract as the carbon source other than the alkanoic acid or alkane.

As an example in which yeast extract is used in the culture medium when PHAs are produced by microorganisms, a process making use of a microorganism belonging to the genus Rhodobacter may be given, which is disclosed in Japanese Patent Application Laid-Open No. 5-49487. This conventional process, however, is a process for producing a common PHB and poly-3-hydroxyvaleric acid (hereinafter often "PHV"), having as a monomer unit a hydroxyalkanoate which does not have any substituent. The synthesis pathway of the PHA that is intended in the present invention is known to be a pathway independent from the synthesis pathway for producing the PHB or PHV. The above Japanese Patent Application Laid-Open No. 5-49487 does not mention at all any effect of the yeast extract in the synthesis pathway of the PHA that is intended in the present invention. Also, as to the effect attributable to the yeast extract, the publication only shows that, with regard to the PHA or PHV which microorganisms commonly produce, the addition of yeast extract brings about the effect of making the PHA accumulate in the bacterial body in a larger quantity, and explicitly states that it is not the case that the yeast extract is added for the purpose of proliferation. The present invention is a process in which thienoylalkanoic acid or thienoylalkane is made coexistent with the yeast extract to produce and accumulate the PHA simultaneously with proliferation. Thus, the effect the yeast extract exhibits is absolutely different. Moreover, the publication does not mention at all the predominant occupation by the specific monomer unit, which is an effect brought about by the present invention, and does not disclose any effect such that as in the present invention the specific monomer unit having a thienoyl group as a substituent occupies predominantly in the composition of the PHA the microorganism produces.

As a further example in which yeast extract is used in producing PHAs by microorganisms, a process making use of *Pseudomonas putida* may be given, which is disclosed in Japanese Patent No. 2,989,175. The PHA production process disclosed in this publication is only a process comprising two-stage culturing, and it is disclosed that the accumulation of PHA is effected only in the second-stage culturing on restrictive condition that a nutrient source other than the carbon source is used. In this regard, this differs absolutely in both construction and effect from the process of the present invention, in which the desired PHA is synthesized and accumulated by only one-stage culturing in the culture medium containing the thienoylalkanoic acid or thienoylalkane and the yeast extract.

The effect attributable to the yeast extract in the above Japanese Patent No. 2,989,175 is directed only to the proliferation of a microorganism to be used in the second-stage culturing, effected in the first-stage culturing when the two-stage culturing is used, and the culturing at the first-stage culturing is carried out under conditions of a rich nutrient source, as so stated explicitly. Here, the substrate of the PHA is not coexistent in the first-stage culturing. The effect attributable to the yeast extract in the present invention is attained by making the thienoylalkanoic acid or thienoylalkane coexistent with the yeast extract to produce and accumulate the PHA simultaneously with proliferation. Thus, the effect the yeast extract exhibits is absolutely different. Also, in the above Japanese Patent No. 2,989,175, any of citric acid, octanoic acid and nonanoic acid is coexistent as a carbon source in the first-stage culturing. Thus, this also differs in construction from the present invention, in which the thienoylalkanoic acid or thienoylalkane is made coexistent with the yeast extract.

Polypeptone; Difference From Prior Art

One of PHA production processes of the present invention is characterized in that, when the microorganism is cultured, in addition to alkanoic acid or alkane for introducing the desired monomer unit, only polypeptone is added to a culture medium as a carbon source other than the alkanoic acid or alkane so that the PHA the microorganism produces and accumulates can have the intended monomer unit in a very high content or have only the intended monomer unit. The effect of promoting the predominant occupation by this specific monomer unit is attained by adding to the culture medium only the polypeptone as the carbon source other than the alkanoic acid or alkane.

As examples in which polypeptone is used in the production of PHAs by microorganisms, Japanese Patent Application Laid-Open Nos. 5-49487, 5-64591, 5-214081, 6-145311, 6-284892, 7-48438, 8-89264, 9-191893, 11-32789 and so forth disclose that polypeptone is incorporated in culture mediums when microorganism are made to produce PHAs. In all of these, however, the polypeptone is used in pre-culuring, i.e., at the stage where the bacterial body is merely proliferated, and any substrate made into the microorganism of PHA is not contained at the time of culturing. Also, these do not disclose any example in which the polypeptone is used in the step of making the bacterial body produce the PHA.

In contrast thereto, the present invention is a process in which the alkanoic acid or alkane for introducing the desired monomer unit is made coexistent only with the polypeptone as a carbon source other than the alkanoic acid or alkane to produce and accumulate the PHA simultaneously with proliferation. Thus, this differs absolutely in both construction and effect from the conventional examples of making use of polypeptone. Moreover, these publications do not mention at all the the predominant occupation by the specific monomer unit, which is an effect brought about by the present invention, and do not disclose any effect such that as in the present invention the specific monomer unit having a thienoyl group as a substituent occupies predominantly in the composition of the PHA the microorganism produces.

The microorganism, culturing steps and so forth used in the present invention are described below.

PHA Monomer Unit Feed System

First, "fatty-acid synthesis pathway" is described in detail which is one of systems for feeding the mcl-3HA monomer unit coming mixedly present in the intended PHA. In the case where the saccharide such as glucose is used as the substrate, the alkanoic acid necessary as a cell component is synthesized through a "fatty-acid synthesis pathway" in which an acetyl-CoA produced from a saccharide through "glycolysis system" is used as a starting substance. Also, the fatty-acid synthesis involves a novel (de novo) synthesis pathway and a carbon chain elongation pathway. These are described below.

(1) Novel (de novo) Synthesis Pathway:

Catalyzed by two enzymes, acetyl-CoA carboxylase (EC 6.4.1.2) and fatty-acid synthesis enzyme (EC 2.3.1.85). Also, the acetyl-CoA carboxylase is an enzyme which catalyzes the following reaction finally, via biotin as a coenzyme, to form a malonyl-CoA from the acetyl-CoA. The reaction is represented by the following scheme.

The fatty-acid synthesis enzyme is an enzyme which catalyzes the reaction cycle of transfer-condensation-reduction-dehydration-reduction. The reaction is represented by the following scheme.

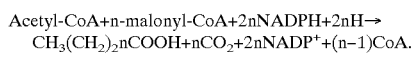

Incidentally, depending on enzymes, the reaction product may be a free acid, a CoA derivative or an ACP (acyl carrier protein) derivative.

Here, the acetyl-CoA is represented by the following chemical formula.

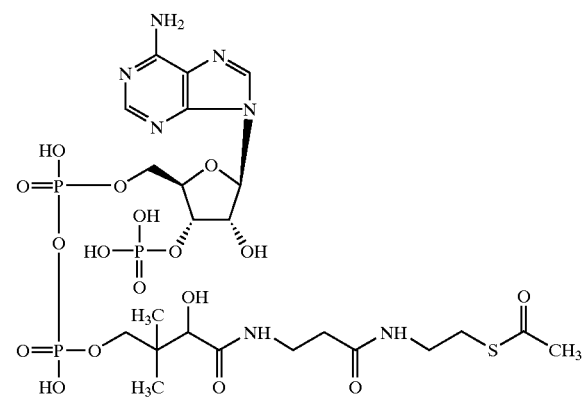

and the malonyl-CoA is represented by the following chemical formula.

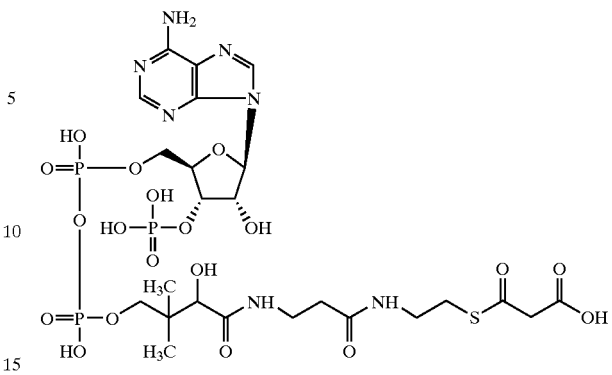

The CoA is the abbreviation for coenzyme A, and is represented by the following chemical formula.

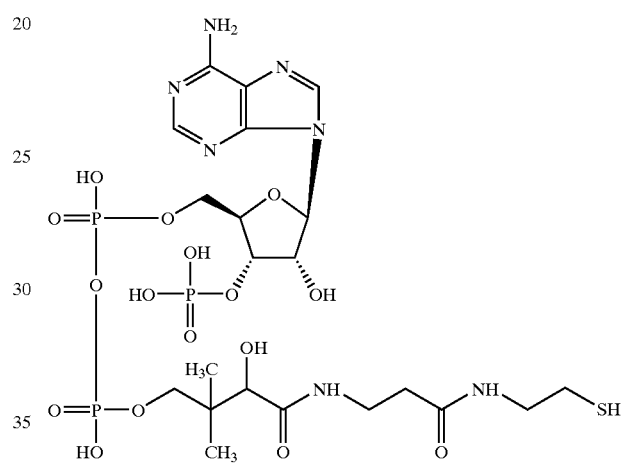

Of the present reaction pathway, "D-3-hydroxyacyl-ACP" serving as a monomer substrate of PHA biosynthesis is fed as an intermediate through a pathway shown below. Also, as shown in the following reaction scheme, the pathway is finally extended up to palmitic acid while carbon atoms are added two by two. Therefore, as the monomer substrate of PHA biosynthesis, seven types of "D-3-hydroxyacyl-ACP" in which the number of carbon atoms of "D-3-hydroxypalmityl-ACP" is an even number come to be fed from "D-3-hydroxybutyryl-ACP".

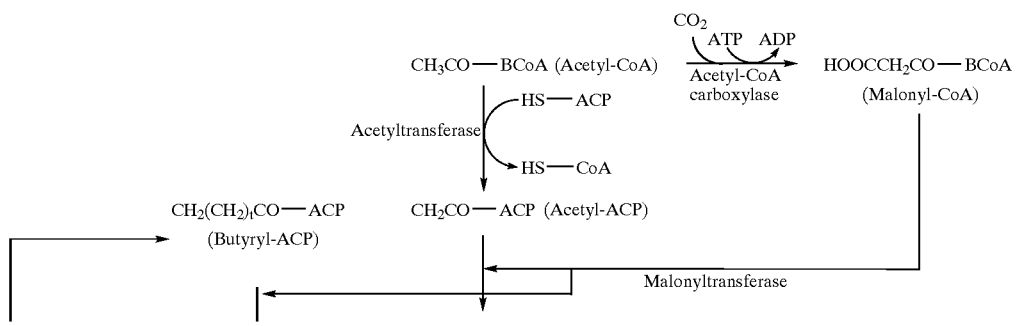

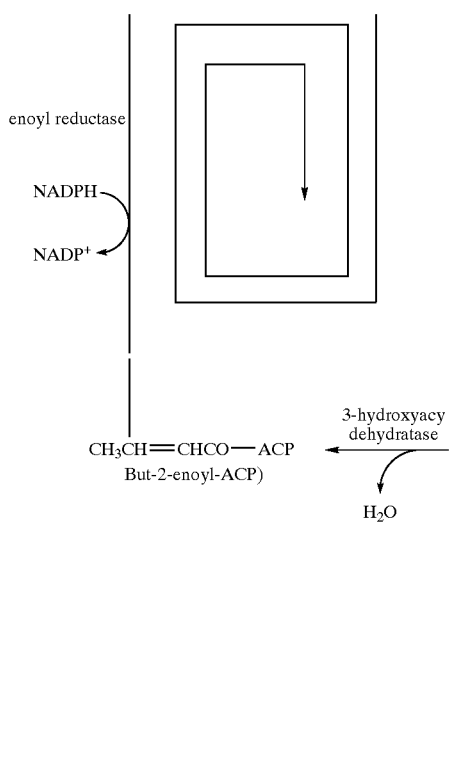
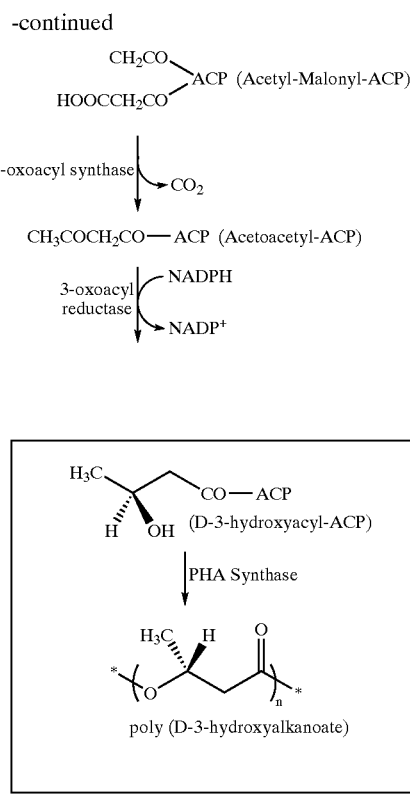

(2) Carbon Chain Elongation Pathway:

This pathway is roughly grouped into two pathways, a pathway in which malonyl-ACP is added to acyl-ACP to come to acyl-ACP (and $CO_2$) the carbon chain of which has finally been elongated by two (herein "pathway A") and a pathway in which acetyl-CoA is added to acyl-CoA to come to acyl-CoA the carbon chain of which has finally been elongated by two (herein "pathway B"). Each pathway is described below.

Pathway A

R—CO—ACP+malonyl-ACP→R—CO—CH$_2$—CO—ACP+CO$_2$

R—CO—CH$_2$—CO—ACP→R—CHOH—CH$_2$—CO—ACP→R—CH=CH—CO—ACP→R—CH$_2$—CH$_2$—CO—ACP

Pathway B

R—CO—CoA+acetyl-CoA→R—CO—CH$_2$—CO—CoA

R—CO—CH$_2$—CO—CoA→R—CHOH—CH$_2$—CO—CoA→R—CH=CH—CO—CoA→R—CH$_2$—CH$_2$—CO—CoA

In either of these systems A and B, "D-3-hydroxyacyl-CoA" or "D-3-hydroxyacyl-ACP" occurs as an intermediate, and the "D-3-hydroxyacyl-CoA" is utilized as the monomer substrate of PHA biosynthesis as it is, and the "D-3-hydroxyacyl-ACP" is utilized as the monomer substrate of PHA biosynthesis after it has been converted into "D-3-hydroxyacyl-CoA" by an ACP-CoA transferase, as so considered.

In the case where the saccharide such as glucose is used as the substrate, it is considered that the mcl-3HA monomer unit is formed in microorganism cells through the "glycolysis system" and "fatty-acid synthesis pathway" as described above. Also, in the case where the organic acid participating in the TCA cycle is used as the substrate, the acetyl-CoA is directly formed from pyruvic acid by the a pyruvic acid dehydrogenase. From oxalacetic acid, phosphoenolpyruvic acid is catalyzed by a pyruvic acid kinase by the a phosphoenolpyruvic acid carboxynase to form pyruvic acid, and the acetyl-CoA is further formed through the above reactions. The acetyl-CoA formed through these reactions passes through the "fatty-acid synthesis pathway" and the mcl-3HA monomer unit is formed, as so considered.

Here, it is considered that mcl-alkanoic acids as exemplified by octanoic acid and nonanoic acid, or alkanoic acids to the terminal of which a functional group other than straight-chain aliphatic alkyl has been added, as exemplified by 5-phenylvaleric acid, 4-phenoxybutyric acid, 4-cyclohexylbutyric acid and 5-(2-thienoyl)valeric acid come to CoA derivatives by the a CoA ligase (EC 6.2.1.3), and come directly to the "D-3-hydroxyacyl-CoA" serving as the monomer substrate of PHA biosynthesis, by the enzymes which undertake the β-oxidation system.

Namely, the mcl-3HA monomer unit formed from the saccharide or the organic acid participating in the TCA cycle is formed through greatly multiple-stage enzymatic reactions (i.e., indirectly), whereas, compared therewith, the mcl-3HA monomer unit comes to be very directly formed from the mcl-alkanoic acid.

The formation of the acetyl-CoA which undertakes the proliferation of microorganisms is described here. In the process in which the mcl-alkanoic acid is made coexistent in addition to the alkanoic acid for introducing the intended monomer unit, these alkanoic acids pass through the β-oxidation system, so that the acetyl-CoA is formed. In general, compared with alkanoic acids having a bulky substituent (alkanoic acids having a substituent such as a phenyl group, a phenoxyl group, a cyclohexyl group or a thienoyl group), the mcl-alkanoic acid is considered to have a superior substrate affinity for the enzymes of the β-oxidation system, and the acetyl-CoA is effectively formed by making the mcl-alkanoic acid coexistent. Hence, it can be advantageous for the proliferation of microorganisms which makes use of the acetyl-CoA as an energy source and a carbon source.

However, since the mcl-alkanoic acid passing through the β-oxidation system comes directly to the monomer unit of the PHA, the PHA thus produced may inevitably come to have the mcl-alkanoic acid mixedly present in a large quantity in addition to the intended monomer unit. This is a great problem.

To solve this problem, a process is preferable in which a substrate that can effectively feed the acetyl-CoA or the energy source and carbon source is selected to make it coexistent with the intended alkanoic acid. As stated previously, the acetyl-CoA can come to the monomer unit of the PHA through the fatty-acid synthesis pathway. Compared with the mcl-alkanoic acid, however, this is an indirect way which must pass through more multiple-stage reactions. Also, a production process which can make any mcl-3HA monomer substantially not, or less, mixedly present can be materialized by appropriately selecting culturing conditions such as the concentration of the substrate that can form the acetyl-CoA.

A production process in which a microorganism is cultured in a first stage only for the purpose of its proliferation and, in a second stage, only the intended alkanoic acid is added as a carbon source to the culture medium is also in general use. Here, an acyl-CoA ligase which is an incipient enzyme of the β-oxidation system where the alkanoic acid is made into the acyl-CoA requires ATP (adenosine triphosphate). From this fact, the studies made by the present inventors have brought out a conclusion that a production process in which the substrate the microorganism can utilize as an energy source is also made coexistent in the second stage, too, is more effective. Thus, they have accomplished the present invention.

As the substrate that can effectively feed the acetyl-CoA or the energy source and carbon source in the process of the present invention, any compound may be used as long as it is a compound capable of forming the acetyl-CoA without passing through the β-oxidation cycle, as exemplified by natural products such as yeast extract, saccharides, organic acids participating to the TCA cycle (organic acids occurring as intermediates in the TCA cycle, and organic acids occurring through one-stage or two-stage biochemical reaction from the TCA cycle) or salts thereof. It may appropriately be selected taking account of its utility as the substrate for microorganism to be use.

Microorganism

As the microorganism used in the present invention, any microorganism may be used as long as it can produce the PHA having as a monomer unit the 3-hydroxythienoylalkanoic acid unit described above, using the thienoylalkanoic acid or thienoylalkane as a raw material. Also, a plurality of microorganisms may optionally be used in the form of a mixture as long as the object of the present invention can be achieved.

Where the thienoylalkane is used as a raw material to produce a PHA containing the corresponding 3-hydroxyalkanoic acid unit as a monomer unit, the microorganism to be used must have at least the ability to convert an alkane into an alkanoic acid and also have the ability to produce the PHA from the alkanoic acid. The ability to convert an alkane into an alkanoic acid is usually brought out by having a group of enzyme systems which contain alkane monooxygenases as incipient enzymes.

The present inventors have investigated microorganisms having the ability to produce PHAs containing as monomer units 3-hydroxythienoylbutyric acid (3HToB), 3-hydroxythienoylvaleric acid (3HToV), 3-hydroxythienoylhexanoic acid (3HToHx) and so forth, using as substrates thienoylbutyric acid (ToBA), thienoylvaleric acid (ToVA), thienoylhexanoic acid (ToHxA) or thienoylhexane (ToHx), and so forth, respectively. As a result, they have found that *Pseudomonas cichorii* strain H45, *Pseudomonas cichorii* strain YN2, *Pseudomonas jessenii* strain P161 and so forth have the desired ability, which are microorganisms the present inventors have isolated from soil, and have the ability to produce the intended PHA. Also, the strain H45, the strain YN2 and the strain P161 are deposited as Deposition Number "FERM BP-7374", Deposition Number "FERM BP-7375" and "FERM BP-7376", respectively, in Patented-Microorganism Deposition Center, Biotechnology Industrial Technology Institute of The Ministry of Economy and Industry.

To enumerate bacteriorogical properties of the above strain H45, strain YN2 and strain P161, they are as shown below. Also, as to the strain P161, the base sequence of 16SrRNA is shown in sequence number 1.

Bacteriological Properties of Strain H45

(1) Morphological Properties

| | |
|---|---|
| Size and shape of cells: | rod-shaped bacteria of 0.8 μm × 1.0 to 1.2 μm. |
| Polymorphism: | no. |
| Mobility: | yes. |
| Sporulation: | no. |
| Gram staining: | negative. |
| Colony formation: | round, entirely smooth periphery low protrusion, smooth surface layer, glossy cream-colored. |

(2) Physiological Properties:

| | |
|---|---|
| Catalase: | positive. |
| Oxidase: | positive. |
| O/F test: | oxidation type. |
| Reduction of nitrate: | negative. |
| Formation of indole: | negative. |
| Souring of D-glucose: | negative. |
| Arginine dihydrolase: | negative. |
| Urease: | negative. |
| Aesculin hydrolysis: | negative. |
| Gelatin hydrolysis: | negative. |
| β-Galactosidase: | negative. |
| Fluorochrome production in King's B agar: | positive. |
| Growth in 4% NaCl: | negative. |
| Accumulation of poly-β-hydroxybutyric acid: | negative. |

Accumulation of poly-β-hydroxybutyric acid: negative.

(3) Substrate Utilization Ability:

| | |
|---|---|
| D-glucose: | positive. |
| L-arabinose: | negative. |
| D-mannose: | positive. |
| D-mannitol: | positive. |
| N-acetyl-D-glucosamine: | positive. |
| Maltose: | negative. |

-continued

| | |
|---|---|
| Potassium gluconate: | positive. |
| n-Capric acid: | positive. |
| Adipic acid: | negative. |
| DL-malic acid: | positive. |
| Sodium citrate: | positive. |
| Phenyl acetate: | positive. |

Bacteriological Properties of Strain YN2

(1) Morphological Properties

| | |
|---|---|
| Size and shape of cells: | rod-shaped bacteria of 0.8 μm × 1.5 to 2.0 μm. |
| Polymorphism: | no. |
| Mobility: | yes. |
| Sporulation: | no. |
| Gram staining: | negative. |
| Colony formation: | round, entirely smooth periphery low protrusion, smooth surface layer, glossy semitransparent. |

(2) Physiological Properties:

| | |
|---|---|
| Catalase: | positive. |
| Oxidase: | positive. |
| O/F test: | oxidation type. |
| Reduction of nitrate: | negative. |
| Formation of indole: | positive. |
| Souring of D-glucose: | negative. |
| Arginine dihydrolase: | negative. |
| Urease: | negative. |
| Aesculin hydrolysis: | negative. |
| Gelatin hydrolysis: | negative. |
| β-Galactosidase: | negative. |
| Fluorochrome production in King's B agar: | positive. |
| Growth in 4% NaCl: | positive (weak growth). |
| Accumulation of poly-β-hydroxybutyric acid: | negative. |
| Hydrolysis of Tween 80: | positive. |

(3) Substrate Utilization Ability:

| | |
|---|---|
| D-glucose: | positive. |
| L-arabinose: | positive. |
| D-mannose: | negative. |
| D-mannitol: | negative. |
| N-acetyl-D-glucosamine: | negative. |
| Maltose: | negative. |
| Potassium gluconate: | positive. |
| n-Capric acid: | positive. |
| Adipic acid: | negative. |
| DL-malic acid: | positive. |
| Sodium citrate: | positive. |
| Phenyl acetate: | positive. |

Bacteriological Properties of Strain P161

(1) Morphological Properties

| | |
|---|---|
| Size and shape of cells: | spherical, 0.6 μm diameter. |
| | rod-shaped, 0.6 μm × 1.5 to 2.0 μm. |
| Polymorphism: | yes (elongation type). |
| Mobility: | yes. |
| Sporulation: | no. |
| Gram staining: | negative. |

-continued

| | |
|---|---|
| Colony formation: | round, entirely smooth periphery low protrusion, smooth surface layer, pale yellow. |

(2) Physiological Properties:

| | |
|---|---|
| Catalase: | positive. |
| Oxidase: | positive. |
| O/F test: | oxidation type. |
| Reduction of nitrate: | positive. |
| Formation of indole: | negative. |
| Souring of D-glucose: | negative. |
| Arginine dihydrolase: | positive. |
| Urease: | negative. |
| Aesculin hydrolysis: | negative. |
| Gelatin hydrolysis: | negative. |
| β-Galactosidase: | negative. |
| Fluorochrome production in King's B agar: | positive. |

(3) Substrate Utilization Ability:

| | |
|---|---|
| D-glucose: | positive. |
| L-arabinose: | positive. |
| D-mannose: | positive. |
| D-mannitol: | positive. |
| N-acetyl-D-glucosamine: | positive. |
| Maltose: | negative. |
| Potassium gluconate: | positive. |
| n-Capric acid: | positive. |
| Adipic acid: | negative. |
| DL-malic acid: | positive. |
| Sodium citrate: | positive. |
| Phenyl acetate: | positive. |

In addition to the microorganisms belonging to the genus Pseudomonas, also usable are microorganisms belonging to the genus Aeromonas, the genus Comamonas, the genus Burkholdera and so forth, and capable of producing the PHA having the 3-hydroxythienoylalkanoic acid unit as a monomer unit, using the thienoylalkanoic acid or thienoylalkane as a raw material.

Culturing

The intended PHA may be produced by culturing any of these microorganisms in a culture medium containing the alkanoic acid or alkane for introducing the desired monomer unit and the substrate for proliferation according to the present invention. Such a PHA is an isotactic polymer, which is commonly constituted of only the R-configuration.

For the usual culturing of microorganisms used in the PHA production process according to the present invention, e.g., for the preparation of storage strains and for the proliferation to ensure the number of microorganism and active state which are required to produce the PHA, a culture medium containing ingredients necessary for the proliferation of microorganisms to be used may be used under appropriate selection. For example, any type of culture mediums such as commonly available natural culture mediums (such as nutrient broth and yeast extract) and synthetic mediums to which nutrient sources have been added may be used as long as they do not adversely affect the growth and existence of microorganisms.

The culturing may be carried out by any culturing method as along as it is a culturing method in which the microorganism proliferates to produce the PHA, such as solid culture. Also usable are batch culture, fed batch culture, semi-continuous culture and continuous culture, without regard to types. As forms of liquid batch culture, a method is available in which the culture medium is shaken in a shaking flask to feed oxygen, and a method in which oxygen is fed by a stirring aeration system using a jar fermenter. Also, a multi-stage system may be employed in which any of these steps are connected in a plurality of stages.

In the case where the PHA containing the 3-hydroxythienoylalkanoic acid unit as a monomer unit is produced by using the PHA-productive microorganism described above, an inorganic culture medium may be used which contains at least i) the thienoylalkanoic acid or thienoylalkane corresponding respectively, as a raw material for producing the PHA and ii) a carbon source for the proliferation of microorganisms.

As a carbon source for proliferation, a culture medium component derived from a natural product such as yeast extract, polypeptone, meet extract or Casamino acid may be used. Also usable are saccharides, organic acids participating to the TCA cycle (organic acids occurring as intermediates in the TCA cycle, and organic acids occurring through one-stage or two-stage biochemical reaction from the TCA cycle) or salts thereof. Any of these compounds may be used as long as they are compounds capable of forming the acetyl-CoA without passing through the β-oxidation cycle. The carbon source may appropriately be selected taking account of its utility as the substrate for microorganism to be use. Also, a plurality of compounds may be used under appropriate selection as long as they are in combination which may have less inclusion of mcl-3HA.

Of these, the saccharides may include aldoses such as glyceraldehyde, erythrose, arabinose, xylose, glucose, galactose, mannose and fructose; alditols such as glycerol, erythritol and xylitol; aldones such as gluconic acid; uronic acids such as glucuronic acid and galacturonic acid; and disaccharides such as maltose, sucrose and lactose. At least one compound selected from these may preferably be used.

The organic acids or salts thereof may include, as examples thereof, pyruvic acid, oxalacetic, citric acid, isocitric acid, ketoglutaric acid, succinic acid, fumaric acid, malic acid and lactic acid, and at least one compound selected from salts of these, any of which may preferably be used.

Of these, it is particularly preferable to use saccharides. In particular, at leas one selected from the group consisting of glucose, fructose and mannose is preferred.

As a method of making the microorganism produce and accumulate the PHA, the microorganism may first sufficiently be proliferated and thereafter the bacterial body may be moved to a culture medium in which a nitrogen source such as ammonium chloride has been restricted, followed by further culturing in the state the compound serving as the substrate of the intended unit has been added. This may bring about an improvement in productivity. Stated specifically, a multi-stage method in which the above step is connected in a multiple stage may be employed. For example, a method is available in which, in an inorganic culture medium which contains approximately from 0.01% to 5.0% of D-glucose and approximately from 0.01% to 1.0% of the thienoylalkanoic acid or thienoylalkane, the microorganism is cultured from the latter phase of logarithmic growth up to a point of time of the stationary phase, and the bacterial body formed is collected by centrifugation or the like, followed by further culturing in a culture medium which contains approximately from 0.01% to 1.0% of the thienoylalkanoic acid or thienoylalkane and in which the nitrogen source has been restricted or is substantially not present.

The inorganic culture medium used in the above culturing method may be any of those which contain ingredients necessary for the proliferation of the microorganism, such as a phosphorus source (e.g., phosphate) and a nitrogen source (e.g., ammonium salt or nitrate), and may include, e.g., MSB medium, E medium (J. Biol. Chem., 218, 97–106, 1956) and M9 medium.

Composition of an inorganic-salt culture medium (M9 medium) used in one method of the present invention is shown below.

M9 Medium:

| | |
|---|---|
| $Na_2HPO_4$ | 6.2 g |
| $KH_2PO_4$ | 3.0 g |
| NaCl | 0.5 g |
| $NH_4Cl$ | 1.0 g |

(in 1 liter of the culture medium; pH: 7.0)

For the purpose of good proliferation and PHA production, about 0.3% (v/v) of a trace-ingredient solution shown below must be added to the above inorganic salt culture medium.

Trace-ingredient Solution:
Nitrilotriacetic acid 1.5 g

| | |
|---|---|
| $MgSO_4$ | 3.0 g |
| $MnSO_4$ | 0.5 g |
| NaCl | 1.0 g |
| $FeSO_4$ | 0.1 g |
| $CaCl_2$ | 0.1 g |
| $CoCl_2$ | 0.1 g |
| $ZnSO_4$ | 0.1 g |
| $CuSO_4$ | 0.1 g |
| $AlK(SO_4)_2$ | 0.1 g |
| $H_3BO_3$ | 0.1 g |
| $Na_2MoO_4$ | 0.1 g |
| NiCl2 | 0.1 g |

(in 1 liter of the solution)

As culturing temperature, it may be temperature at which the above strain can well be proliferated. For example, it may suitably be from 15° C. to 40° C., preferably from 20° C. to 35° C., and more preferably from 20° C. to 30° C., in approximation.

As a specific example, the microorganism is cultured in an inorganic culture medium which contains approximately from 0.05% to 5.0% of D-glucose and approximately from 0.01% to 1.0% of the thienoylalkanoic acid or thienoylalkane, and the bacterial body is collected at the stage of from the latter phase of logarithmic growth up to a point of time of the stationary phase. Thus, the desired PHA can be extracted, in which the unintended monomer units are less mixedly present or not present at all. Such a PHA is an isotactic polymer, which is commonly constituted of only the R-configuration.

In place of D-glucose, the organic acid participating to the TCA cycle, the yeast extract or the polypeptone may be added. Any combination of these may also be used.

Collection of PHA

To gain the PHA from the culture solution according to the present invention, conventionally available methods may be used. Where the PHA is secreted in the culture solution, a method may be used in which it is extracted from the culture solution and purified, and, where the PHA is accumulated in the bacterial body, a method in which it is extracted from the bacterial body and purified. For example, for the collection of the PHA from the cultured bacterial body of a microorganism, extraction with an organic solvent such as chloroform is most simple, which is conventionally made. Besides the chloroform, dioxane, tetrahydrofuran, acetonitrile or acetone is used in some cases. Also, in an environment which should be kept from use of organic solvents, a method may be used in which bacterial-body components other than the PHA are removed to collect the PHA, by treating microorganism cells with a surface-active agent such as SDS (sodium dodecyl sulfate), treating them with an enzyme such as lysozyme, or treating them with a chemical such as EDTA (ethylenediaminetetraacetic acid).

The culturing of microorganisms according to the present invention, the production of the PHA by microorganisms and its accumulation in the bacterial body according to the present invention, and the collection of the PHA from the bacterial body in the present invention are by no means limited to the above methods.

The present inventors have also made extensive studies aiming at the development of a charge control agent which is highly contributory to the environmental safeguard and so forth and also has high performances. As a result, they have discovered that the polyhydroxyalkanoate described above has very good properties as a charge control agent and has a high safety to human bodies and environment, and also that a remarkable effect is brought about when a toner for developing electrostatic latent images which contains this charge control agent is used and such a toner for developing electrostatic latent images is used in an image-forming apparatus having a certain latent-image-developing system. Thus, they have accomplished the present invention.

More specifically, the present invention is a charge control agent comprising the polyhydroxyalkanoate described above, and also a toner for developing electrostatic latent images which comprises the charge control agent. The present invention is further an image-forming method comprising a charging step of applying a voltage to a charging member from its outside to charge an electrostatic-latent-image-bearing member electrostatically; a developing step of developing an electrostatic latent image on the electrostatic-latent-image-bearing member by the use of the above toner for developing electrostatic latent images, to form a toner image thereon; a transfer step of transferring to a recording medium the toner image formed on the electrostatic-latent-image-bearing member, via, or not via, an intermediate transfer member; and a heat fixing step of fixing by heat the toner image held on the recording medium. The present invention is still further an image-forming apparatus having means corresponding respectively to the steps of this method, i.e., a charging means, a developing means, a transfer means and a heat fixing means.

Here, the polyhydroxyalkanoate used in the present invention has a fundamental structure as a biodegradable resin. Hence, like conventional plastic, it can be utilized in the manufacture of various products by melting, and, different from synthetic polymers derived from petroleum, has a striking property that it is broken down by microorganisms and taken into the circulation of substances in the natural world. Accordingly, it does not require any disposal by combustion, and is an effective material also from the viewpoint of the prevention of air pollution and global warming. Thus, it can be utilized as a plastic which enables environmental safeguard.

The polyhydroxyalkanoate preferable as the charge control agent, used in the toner for developing electrostatic latent images according to the present invention is specifically described below.

The polyhydroxyalkanoate used as the charge control agent in the present invention is a polyester resin having a 3-hydroxyalkanoate as a monomer unit, and is a polyhydroxyalkanoate having in the molecule at least one unit of units represented by Chemical Formula (1). In addition to the units represented by Chemical Formula (1):

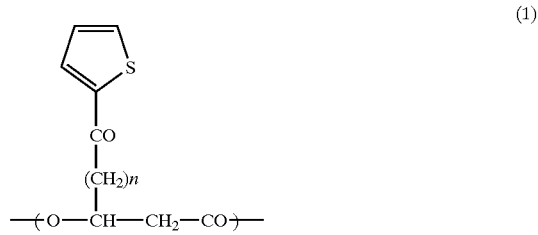

wherein n may assume any one integral value within the range of from 1 to 8, it may further contain simultaneously or independently a straight-chain 3-hydroxyalkanoate and a 3-hydroxyalkenoate containing an unsaturated bond in the side chain.

The polyhydroxyalkanoate used in the present invention is also a polyester resin having a 3-hydroxyalkanoate as a monomer unit, and is a polyhydroxyalkanoate having in the molecule at least one unit of units represented by Chemical Formula (12):

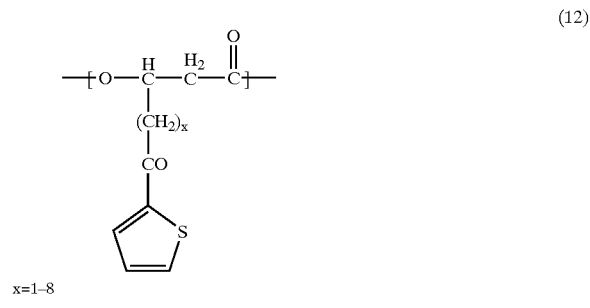

x=1–8 wherein n may assume any one integral value within the range of from 1 to 8.

In addition to the units represented by Chemical Formula (12), it may further contain simultaneously or independently a straight-chain 3-hydroxyalkanoate and a 3-hydroxyalkenoate containing an unsaturated bond in the side chain.

Here, where such a compound is produced by the process having the step of producing it by a microorganism, the above polyhydroxyalkanoate is an isotactic polymer of only R-configuration. As long as the object of the present invention is achievable on both aspects of physical properties and function, it need not especially be the isotactic polymer. An atactic polymer may also be used. Also, the above polyhydroxyalkanoate may also be obtained by a process having in its steps chemical synthesis utilizing, e.g., ring-opening polymerization of a lactone compound.

Examples of the process for producing the polyhydroxyalkanoate used as the charge control agent of the present invention are as described previously. An example of a production process utilizing the thienoylalkanoic acid or thienoylalkane has been described above in detail. With regard to the polyhydroxyalkanoate which contains the units represented by Chemical Formula (12), too, it may likewise be produced utilizing a thienylalkanoic acid or the like.

What is important in the present invention is that the polyhydroxyalkanoate has a thienyl structure, or has a thienyl structure and a carbonyl structure (thienoyl structure). Such structure causes electrons to be localized (localization of electrons) in the molecule, and hence the charge control agent of the present invention can have a superior negative chargeability. The charge control agent of the present invention, having such structure differs from any negatively chargeable polymeric charge control agents having ever been disclosed. It does not contain any ionic functional group and has superior weatherability inclusive of moisture resistance.

It is also possible to control the rise of charge by changing the percentage of the unit having such structure. It is further possible to lessen its environmental dependence by controlling such unit percentage.

The unit having such structure may be in a content of at least 1 mol % in the polymer. Its proportion may be selected taking account of the percentage to other units and the desired chargeability. In order to exhibit sufficient chargeability, it may preferably be in a content of 5 mol % or more. Also, the upper limit of content of the unit to be contained may be selected taking account of the type of a binder resin to be selected and the percentage to other units, and may be within the range the compatibility with the binder resin is not damaged.

The polyhydroxyalkanoate used in the present invention has a good compatibility with the binder resin. In particular, it has a very good compatibility with a polyester type binder resin. The toner incorporated with the polyhydroxyalkanoate of the present invention has a high specific charge quantity and its stability with time is also good. Hence, even after the toner has been stored over a long period of time, it can stably provide sharp images in the formation of images by electrostatic recording. It also has colorless negatively charging performance, and hence it can be employed for any of negatively chargeable black toners and color toners.

In addition, appropriate selection of the types and compositional ratio of monomer units constituting the polyhydroxyalkanoate of the present invention enables control of compatibility over a wide range. Here, the resin composition may be so selected that the charge control agent assumes a microscopically phase-separated structure in the toner binder, where the toner does not come to have any electrical continuity and hence it can stably retain electric charges. Also, the polyhydroxyalkanoate of the present invention does not contain any heavy metal. Hence, when the toner is produced by suspension polymerization or emulsification polymerization, the charge control agent does not have any polymerization inhibitory action which may be seen in heavy-metal-containing charge control agents, and hence the toner can stably be produced.

Addition of PHA to Toner

In the present invention, as a method of incorporating the above compound in the toner, a method of adding it internally to toner particles and a method of adding it externally to toner particles are available. When it is internally added, it may usually be added in an amount ranging from 0.1 to 50% by weight, preferably from 0.3 to 30% by weight, and more preferably from 0.5 to 20% by weight, as weight proportion between the toner binder and the charge control agent. Its addition in an amount of less than 0.1% by weight is not preferable because the toner may not be improved in chargeability in any remarkable extent. On the other hand its addition in an amount of more than 50% by weight is not preferable from an economical viewpoint. Also, when it is externally added, it may usually be added in an amount of from 0.01 to 5% by weight as weight proportion between the toner binder and the charge control agent, and may particularly preferably be made to adhere to toner particle surfaces mechanochemically. The polyhydroxyalkanoate of the present invention may further be used in combination with any known charge control agent.

The polyhydroxyalkanoate of the present invention may usually have a number-average molecular weight of from 1,000 to 500,000, and preferably from 1,000 to 300,000. If it has a number-average molecular weight less than 1,000, it may completely dissolve in the toner binder to form a discontinuous domain with difficulty, resulting in an insufficient charge quantity and also affecting the fluidity of toner adversely. If it has a number-average molecular weight of more than 500,000, it may be dispersed in the toner with difficulty.

The molecular weight of the polyhydroxyalkanoate is measured by GPC (gel permeation chromatography). As a specific method for the measurement by GPC, the molecular weight of a sample prepared by dissolving the polyhydroxyalkanoate previously in dimethylformamide (DMF) containing 0.1% by weight of LiBr is measured through a like mobile phase, and its molecular weight distribution is determined from a calibration curve of a standard polystyrene resin.

In the present invention, as the ratio of weight-average molecular weight (Mw) to number-average molecular weight (Mn) as measure as described above, the polyhydroxyalkanoate may also have an Mw/Mn in the range of from 1 to 10, which may preferably be used.

The polyhydroxyalkanoate used in the present invention may preferably have a melting point of from 20 to 150° C., and particularly from 40 to 150° C., or, though having no melting point, may preferably have a glass transition point of from 20 to 150° C., and particularly from 40 to 150° C. If it has a melting point below 20° C., or has no melting point and has a glass transition point below 20° C., it may adversely affect the fluidity or storage stability of toner. If on the other hand it has a melting point above 150° C., or has no melting point and has a glass transition point above 150° C., the toner may be kneaded in the toner with difficulty, tending to result in a broad charge quantity distribution.

The melting point Tm and the glass transition point Tg in this case may be measured with, e.g., a differential scanning calorimeter of a highly precise, inner-heat input compensation type, such as DSC-7, manufactured by Perkin Elmer Co.

In the toner binder and toner for developing electrostatic latent images according to the present invention, the toner binder and the charge control agent may usually be in a weight proportion of from 0.1 to 50% by weight, preferably from 0.3 to 30% by weight, and more preferably from 0.5 to 20% by weight. The toner for developing electrostatic latent images according to the present invention may have a compositional proportion that usually the charge control agent is in an amount of from 0.1 to 50% by weight, the toner binder from 20 to 95% by weight, and a coloring material from 0 to 15% by weight, on the basis of toner weight. The toner may optionally contain a magnetic powder (such as a powder of a ferromagnetic metal such as iron, cobalt or nickel or a compound such as magnetite, hematite or ferrite) in an amount of 60% by weight or less so as to have also the function as a coloring material. It may further contain various additives such as a lubricant (e.g., polytetrafluoroethylene, a low-molecular weight polyolefin, a fatty acid, or a metal salt or amide thereof), and other charge control agent (e.g., a metal-containing azo dye or a salicylic acid metal salt). Also, in order to improve the fluidity of toner, a fine hydrophobic colloidal silica powder or the like may also be used. Any of these may usually be added in an amount of 10% by weight or less.

In the toner of the present invention, it is preferable that at least part of the toner binder forms a continuous domain and at least part of the charge control agent forms a discontinuous domain. Compared with a case in which the charge control agent completely dissolves in the toner binder without forming any discontinuous domain, the charge control agent added tends to come uncovered to toner particle surfaces, so that it can exhibit the intended effect in its addition in a small quantity. Also, the domains may preferably be dispersed in a particle diameter of from 0.01 to 4 μm, and more preferably from 0.05 to 2 μm. If they are dispersed in a particle diameter larger than 4 μm, they may stand dispersed insufficiently, resulting in a broad charge quantity distribution and also causing a problem that the toner may have a poor transparency. If on the other hand they are dispersed in a particle diameter smaller than 0.01 μm, they stand like the case in which the charge control agent completely dissolves in the toner binder without forming any discontinuous domain, making it necessary to add the charge control agent in a large quantity.

Whether or not at least part of the charge control agent forms a discontinuous domain and what dispersion particle diameter it has can be ascertained by observing slices of toner particles on a transmission electron microscope or the like. To observe interfaces clearly, it is also effective to dye the slices of toner particles with ruthenium tetraoxide or osmium tetraoxide and thereafter observe them on the electron microscope.

For the purpose of making small the discontinuous domain which the polyhydroxyalkanoate of the present invention forms, a polymer having compatibility with the polyhydroxyalkanoate of the present invention and having compatibility also with the toner binder may also be incorporated as a compatibilizer. The compatibilizer may include polymers in which a polymer chain containing 50 mol % or more of a monomer having substantially the same structure as the constituent monomer of the polyhydroxyalkanoate of the present invention and a polymer chain containing 50 mol % or more of a monomer having substantially the same structure as the constituent monomer of the toner binder are combined in the form of a graft or in the form of a block. The compatibilizer may usually be used in an amount of 30% by weight or less, and preferably from 1 to 10% by weight, based on the weight of the polyhydroxyalkanoate of the present invention.

Other Materials

Other constituent materials which constitute the toner for developing electrostatic latent images according to the present invention are described below.

(Binder Resin)

First, as the binder resin, any of those usually used when toners are produced may be used without any particular limitations. Also, before the toner is made up, the charge control agent of the present invention may previously be mixed with the binder resin so that it can be used as a toner binder composition (the toner binder) of the present invention, having a charge controlling ability. For example, the binder resin may include styrene type polymers, polyester type polymers, epoxy type polymers, polyolefin type polymers and polyurethane type polymers, any of which may be used alone or in the form of a mixture.

The styrene type polymers may include copolymers of styrene with acrylate or methacrylate and copolymers of other monomers copolymerizable with these, and copolymers of styrene with diene monomers (such as butadiene and isoprene) and copolymers of other monomers copolymerizable with these. The polyester type polymers may include polycondensation products of aromatic dicarboxylic acids with alkylene oxide addition products of aromatic diols. The epoxy type polymers may include reaction products of aromatic diols with epichlorohydrin, and modified products thereof. The polyolefin type polymers may include polyethylene, polypropylene, and copolymers of any of these with other copolymerizable monomers. The polyurethane type polymers may include polyaddition products of aromatic diisocyanates with alkylene oxide addition products of aromatic diols.

As specific examples of the binder resin used in the present invention, it may include polymers of the following polymerizable monomers, or mixtures of any of these, or copolymerization products obtained using two or more of the following polymerizable monomers. Such resins may specifically include, e.g., styrene type polymers such as styrene-methacrylic acid type polymers, as well as the polyester type polymers, epoxy type polymers, polyolefin type polymers and polyurethane type polymers.

As specific examples of the polymerizable monomers, it may include, e.g., styrene; styrene derivatives such as o-methylstyrene, m-methylstyrene, p-methylstyrene, p-methoxystyrene, p-phenylstyrene, p-chlorostyrene, 3,4-dichlorostyrene, p-ethylstyrenee, 2,4-dimethylstyrene, p-n-butylstyrene, p-tert-butylstyrene, p-n-hexylstyrene, p-n-octylstyrene, p-n-nonylstyrene, p-n-decylstyrene and p-n-dodecylstyrene; ethylene unsaturated monoolefins such as ethylene, propylene, butylene and isobutylene; unsaturated polyenes such as butadiene; vinyl halides such as vinyl chloride, vinylidene chloride, vinyl bromide and vinyl fluoride; vinyl esters such as vinyl acetate, vinyl propionate and vinyl benzoate; α-methylene aliphatic monocarboxylates such as methyl methacrylate, ethyl methacrylate, propyl methacrylate, n-butyl methacrylate, isobutyl methacrylate, n-octyl methacrylate, dodecyl methacrylate, 2-ethylhexyl methacrylate, stearyl methacrylate, phenyl methacrylate, dimethylaminoethyl methacrylate and diethylaminoethyl methacrylate; acrylic esters such as methyl acrylate, ethyl acrylate, n-butyl acrylate, isobutyl acrylate, propyl acrylate, n-octyl acrylate, dodecyl acrylate, 2-ethylhexyl acrylate, stearyl acrylate, 2-chloroethyl acrylate and phenyl acrylate; vinyl ethers such as methyl vinyl ether, ethyl vinyl ether and isobutyl vinyl ether; vinyl ketones such as methyl vinyl ketone, hexyl vinyl ketone and methyl isopropenyl ketone; N-vinyl compounds such as N-vinylpyrrole, N-vinylcarbazole, N-vinylindole and N-vinylpyrrolidone; vinylnaphthalenes; acrylic acid or methacrylic acid derivatives such as acrylonitrile, methacrylonitrile and acrylamide; esters of the above α,β-unsaturated acids and diesters of dibasic acids; dicaroxylic acids such as maleic acid, methyl maleate, butyl maleate, dimethyl maleate, phthalic acid, succinic acid and terephthalic acid; polyol compounds such as ethylene glycol, diethylene glycol, triethylene glycol, 1,2-propylene glycol, 1,3-propylene glycol, 1,4-butanediol, 1,6-hexanediol, bisphenol A, hydrogenated bisphenol A and polyoxyethylene type bisphenol A; isocyanates such as p-phenylenediisocyanate, p-xylylenediisocyanate and 1,4-tetramethylenediisocyanate; amines such as ethylamine, butylamine, ethylenediamine, 1,4-diaminobenzene, 1,4-diaminobutane and monoethanolamine; and epoxy compounds such as diglycidyl ether, ethylene glycol diglycidyl ether, bisphenol-A diglycidyl ether and hydroquinone diglycidyl ether.

(Cross-linking Agent)

When the binder resin used in the present invention is made up, a cross-linking agent as shown below may optionally be used.

For example, it may include, as bifunctional cross-linking agents, divinylbenzene, bis(4-acryloxypolyethoxyphenyl)propane, ethylene glycol diacrylate, 1,3-butylene glycol diacrylate, 1,4-butanediol diacrylate, 1,5-pentanediol diacrylate, 1,6-hexanediol diacrylate, neopentyl glycol diacrylate, diethylene glycol diacrylate, triethylene glycol diacrylate, tetraethylene glycol diacrylate, polyethylene glycol #200 diacrylate, polyethylene glycol #400 diacrylate, polyethylene glycol #600 diacrylate, dipropylene glycol diacrylate, polypropylene glycol diacrylate, polyester type diacrylates (MANDA, trade name; available from Nippon Kayaku Co., Ltd.), and the above diacrylates whose acrylate moiety has been replaced with methacrylate.

As trifunctional or higher polyfunctional cross-linking agents it may include, e.g., pentaerythritol triacrylate, trimethylolethane triacrylate, trimethylolpropane triacrylate, tetramethylolmethane tetraacrylate, oligoester acrylate, and these compounds whose acrylate moiety has been replaced with methacrylate, and also 2,2-bis(4-methacyloxypolyethoxyphenyl)propane, diallyl phthalate, triallyl cyanurate, triallyl asocyanurate triallyl isocyanurate, triallyl trimellitate and diaryl chlorendate.

(Polymerization Initiator)

When the binder resin used in the present invention is made up, a polymerization initiator as shown below may also optionally be used.

For example, it may include butyl peroxy-2-ethylhexanoate, cumin perpivalate, t-butyl peroxylaurate, benzoyl peroxide, lauroyl peroxide, octanoyl peroxide, di-t-butyl peroxide, t-butylcumyl peroxide, dicumyl peroxide, 2,2'-azobis(2-isobutyronitrile), 2,2'-azobis(2-methylbutyronitrile), 2,2'-azobis(2,4-dimethylvaleronitrile), 2,2'-azobis(4-methoxy-2,4-dimethylvaleronitrile), 1,1-bis(t-butylperoxy)-3,3,5-trimethylcyclohexane, 1,1-bis(t-butylperoxy)cyclohexane, 1,4-bis(t-butylperoxycarbonyl)cyclohexane, 2,2-bis(t-butylperoxy)octane, n-butyl-4,4-bis(t-butylperoxy) valylate, 2,2-bis(t-butylperoxy)butane, 1,3-bis(t-butylperoxy-isopropyl)benzene, 2,5-dimethyl-2,5-di(t-butylperoxy)hexane, 2,5-dimethyl-2,5-di(t-butylperoxy)hexane, 2,5-dimethyl-2,5-di(benzoylperoxy)hexane, di-t-butyl peroxyisophthalate, 2,2-bis(4,4-di-t-butylperoxycyclohexyl)propane, di-t-butylperoxy-α-methylsuccinate, di-t-butyl peroxydimethylglutarate, di-t-butyl peroxyhexahydroterephthalate, di-t-butyl peroxyazelate, 2,5-diemthyl-2,5-di(t-butylperoxy)hexane, diethylene glycol-bis(t-butylperoxycarbonate), di-t-butyl peroxytrimethyladipate, tris(t-butylperoxy)triazine and vinyl tris(t-butylperoxy)silane. Any of these may used alone or in combination. The initiator may be used in an amount of not less than 0.05 part by weight, and preferably from 0.1 part by weight to 15 parts by weight, based on 100 parts by weight of the monomer.

(Other Biodegradable Plastic)

In the present invention, a biodegradable plastic may also preferably be used. The biodegradable plastic may include ECOSTAR and ECOSTAR PLUS (trade names; available from Hagiwara Kogyo), BIOPOLE (trade name; available from I.C.I Japan), AJICOAT (trade name; available from Ajinomoto), PLACCELL and POLYCAPROLACTONE (trade names; available from Daicell Chemical), SHOREX and BIONORE (trade names; available from Showa Denko), LACTY (trade name; available from Shimadzu Corporation), and RAYCIA (Mitsui Chemical).

In the combination of any of these resins with the charge control agent of the present invention, the polymer structure of the binder resin and the polymer structure of the polymer chain of the charge control agent may preferably be similar to each other as far as possible. If the polymer structure of the binder resin and the polymer structure of the polymer chain of the charge control agent are greatly different from each other, the charge control agent tends to be insufficiently dispersed in the binder resin.

The charge control agent of the present invention may usually internally be added to the binder resin in a weight proportion of from 0.1 to 50% by weight, preferably from 0.3 to 30% by weight, and more preferably from 0.5 to 20% by weight. Here, if the weight proportion of the charge control agent internally added is less than 0.1% by weight, a low charge quantity may result. If it is more than 50% by weight, the toner may have a poor charging stability.

(Colorant)

As the colorant that constitutes the toner for developing electrostatic latent images according to the present invention, any colorants may be used as long as they are those usually used when toners are produced. For example, carbon black, titanium white and any other all pigments and/or dyes may be used.

For example, when the toner for developing electrostatic latent images according to the present invention is used as a magnetic color toner, the colorant may include, e.g., C.I. Direct Red 1, C.I. Direct Red 2, C.I. Acid Red 1, C.I. Basic Red 1, C.I. Mordant Red 1, C.I. Direct Blue 1, C.I. Direct Blue 2, C.I. Acid Blue 9, C.I. Acid Blue 15, C.I. Basic Blue 3, C.I. Basic Blue 5, C.I. Mordant Blue 7, C.I. Direct Green 6, C.I. Basic Green 4 and C.I. Basic Green 6. As the pigments, usable are chrome yellow, cadmium yellow, mineral fast yellow, navel yellow, Naphthol Yellow S, Hanza Yellow G, Permanent Yellow NCG, Tartrazine Yellow Lake, chrome orange, molybdenum orange, Permanent Orange GTR, Pyrazolone Orange, Benzidine Orange G, cadmium red, Permanent Red 4R, Watching Red calcium salt, Eosine Lake, Brilliant Carmine 3B, manganese violet, Fast Violet B, Methyl Violet Lake, Prussian blue, cobalt blue, Alkali Blue Lake, Victoria Blue Lake, Phthalocyanine Blue, Fast Sky Blue, Indanthrene Blue BC, chrome green, chromium oxide, Pigment Green B, Malachite Green Lake, Final Yellow Green G and so forth.

When the toner for developing electrostatic latent images according to the present invention is used as toners for full-color two-component developers, those shown below may be used as colorants. For example, color pigments for a magenta toner may include, C.I. Pigment Red 1, 2, 3, 4, 5, 6, 7, 8, 9, 10, 11, 12, 13, 14, 15, 16, 17, 18, 19, 21, 22, 23, 30, 31, 32, 37, 38, 39, 40, 41, 48, 49, 50, 51, 52, 53, 54, 55, 57, 58, 60, 63, 64, 68, 81, 83, 87, 88, 89, 90, 112, 114, 122, 123, 163, 202, 206, 207, 209; C.I. Pigment Violet 19; and C.I. Vat Red 1, 2, 10, 13, 15, 23, 29, 35.

In the present invention, any of the pigments listed above may be used alone, or dyes may be used in combination with such pigments so that color sharpness can be improved. This is preferable in view of image quality of full-color images. Magenta dyes usable in such a case may include oil-soluble dyes such as C.I. Solvent Red 1, 3, 8, 23, 24, 25, 27, 30, 49, 81, 82, 83, 84, 100, 109, 121, C.I. Disperse Red 9, C.I. Solvent Violet 8, 13, 14, 21, 27, and C.I. Disperse Violet 1; and basic dyes such as C.I. Basic Red 1, 2, 9, 12, 13, 14, 15, 17, 18, 22, 23, 24, 27, 29, 32, 34, 35, 36, 37, 38, 39, 40, and C.I. Basic Violet 1, 3, 7, 10, 14, 15, 21, 25, 26, 27, 28.

As other color pigments, cyan color pigments may include C.I. Pigment Blue 2, 3, 15, 16, 17, C.I. Vat Blue 6, C.I. Acid Blue 45, or copper phthalocyanine pigments whose phthalocyanine skeleton has been substituted with 1 to 5 phthalimide methyl group(s).

Yellow color pigments may include C.I. Pigment Yellow 1, 2, 3, 4, 5, 6, 7, 10, 11, 12, 13, 14, 15, 16, 17, 23, 65, 73, 83, and C.I. vat Yellow 1, 3, 20.

The dyes and pigments as described above may each be used alone. Otherwise, any of them may arbitrarily be mixed and then used, in order to obtain the desired color tone of toners. Taking account of the environmental conservation and the safety to human bodies, food dyes of various types may preferably be used.

The content of the above colorant in the toner may be changed in a wide range in accordance with the desired coloring effect and so forth. Usually, in order to attain the best toner characteristics, i.e., taking account of coloring power for printing, shape stability of toner particles, toner scattering and so forth, any of these colorants may usually be used in an amount of from 0.1 to 60 parts by weight, and preferably from 0.5 to 20 parts by weight, based on 100 parts by weight of the binder resin.

Other Components of Toner

In the toner for developing electrostatic latent images according to the present invention, in addition to the binder resin and colorant components described above, the following compounds may be added as long as they do not adversely influence the effect of the present invention (i.e., in the proportion smaller than the content of the binder resin component). Such compounds are exemplified by silicone resin, polyester, polyurethane, polyamide, epoxy resin, polyvinyl butyral, rosin, modified rosin, terpene resin, phenolic resin, aliphatic hydrocarbon resin such as low-molecular weight polyethylene or low-molecular weight polypropylene or alicyclic hydrocarbon resin, aromatic petroleum resin and chlorinated paraffin or paraffin wax. Waxes preferably usable among these may specifically include low-molecular weight polypropylene and by-products thereof, low-molecular weight polyester, ester waxes, and aliphatic derivatives. Waxes obtained from these waxes by fractionating the waxes by various methods may also preferably be used. Also, after the fractionation, the waxes may be subjected to oxidation, block copolymerization or graft modification.

In the toner for developing electrostatic latent images according to the present invention, a toner having superior performance can be obtained especially when it contains the above wax component and such a wax component stands dispersed in the binder resin in the form of spherical and/or spindle-shaped islands in its cross-sectional observation of toner particles using a transmission electron microscope (TEM).

Toner Production Process

As a specific process for producing the toner for developing electrostatic latent images according to the present invention, constituted as described above, any conventionally known process may be used. The toner for developing electrostatic latent images according to the present invention may be produced by, e.g., what is called a pulverization process, which produces the toner according to the following steps. That is, stated specifically, the polyhydroxyalkanoate, resins such as the binder resin, and other components such as the wax optionally added are thoroughly mixed by means of a mixing machine such as a Henschel mixer or a ball mill, and then the mixture is melt-kneaded using a heat kneading machine such as a heating roll, a kneader or an extruder to make the resin and so on melt one another, in which the pigment, dye or magnetic material as the colorant and additives such as a metal compound optionally added are then dispersed or dissolved, followed by cooling for solidification. Thereafter, the solidified product is pulverized by means of a grinding machine such as a jet mill or a ball mill, followed by classification. Thus, the toner for developing electrostatic latent images according to the present invention, having the desired particle diameter, can be obtained. Incidentally, in the step of classification, a multi-division classifier may preferably be used in view of production efficiency.

The toner for developing electrostatic latent images according to the present invention, having the desired particle diameter, may also be obtained by mixing the binder resin and the polyhydroxyalkanoate in the form of a solution using a solvent (including aromatic hydrocarbons such as toluene and xylene, halogenated products such as chloroform and ethylene dichloride, ketones such as acetone and methyl ethyl ketone, and amides such as dimethylformamide), stirring the solution, and thereafter introducing the resultant solution into water to effect reprecipitation, followed by filtration and then drying, and thereafter pulverizing the solidified product by means of a grinding machine such as a jet mill or a ball mill, followed by classification. Incidentally, in the step of classification, a multi-division classifier may preferably be used in view of production efficiency.

The toner for developing electrostatic latent images according to the present invention may still also be produced by what is called a polymerization process as described below. That is, in this case, materials such as the polyhydroxyalkanoate, the polymerizable monomer, the pigment, dye or magnetic material as the colorant, and optionally the cross-linking agent, the polymerization initiator, the wax and other additives are mixed and dispersed to prepare a polymerizable monomer composition, which is then subjected to suspension polymerization in an aqueous dispersion medium to synthesize polymerized color resin particles. The resin particles thus obtained are solid-liquid separated, followed by drying and then optionally classification to obtain the toner for developing electrostatic latent images according to the present invention.

As another method, colored fine particles not containing any charge control agent may be prepared by the above process, and then the polyhydroxyalkanoate may be added thereto alone, or together with an external additive such as colloidal silica, by a mechanochemical method to cause the latter to adhere to the former's particle surfaces.

(Silica External Additive)

In the present invention, to the toner produced by the process as described above, it is preferable to add a fine silica powder in order to improve toner's charging stability, fluidity and running performance. As the fine silica powder used here, a fine silica powder having a specific surface area of 20 $m^2/g$ or more, and particularly in the range of from 30 to 400 $m^2/g$, as measured by nitrogen adsorption according to the BET method, gives good results. In this case, the fine silica powder may be used in an amount of from 0.01 to 8 parts by weight, and preferably from 0.1 to 5 parts by weight, based on 100 parts by weight of the toner particles. For the purpose of making hydrophobic and controlling chargeability, the fine silica powder used here may preferably optionally be treated with a treating agent such as a silicone varnish, a modified silicone varnish of various types, a silicone oil, a modified silicone oil of various types, a silane coupling agent, a silane coupling agent having a functional group or other organosilicon compound. Use of such a treated powder is preferred. Any of these treating agents may be used in the form of a mixture.

(Inorganic Powder)

In order to improve toner's developing performance and running performance, it is also preferable to add the following inorganic powder. It may include, e.g., oxides of metals such as magnesium, zinc, aluminum, cerium, cobalt, iron, zirconium, chromium, manganese, strontium, tin and antimony; composite metal oxides such as calcium titanate, magnesium titanate and strontium titanate; metal salts such as calcium carbonate, magnesium carbonate and aluminum carbonate; clay minerals such as kaolin; phosphoric acid compounds such as apatite; silicon compounds such as silicon carbide and silicon nitride; and carbon powders such as carbon black and graphite powder. In particular, fine powder of zinc oxide, aluminum oxide, cobalt oxide, manganese dioxide, strontium titanate or magnesium titanate may preferably be used.

(Lubricant)

A lubricant powder as shown below may also be added to the toner. It may include, e.g., fluorine resins such as Teflon and polyvinylidene fluoride; fluorine compounds such as carbon fluoride; fatty acid metal salts such as zinc stearate; fatty acids, and fatty acid derivatives such as fatty esters; and molybdenum sulfide.

Carrier

The toner for developing electrostatic latent images according to the present invention, constituted as described above, may be used alone as a non-magnetic one-component developer, or may be applied to conventionally known various toners such as a non-magnetic toner which constitutes a magnetic two-component developer together with a magnetic carrier, and a magnetic toner used alone as a magnetic one-component developer. Here, as a carrier used in two-component development, any of conventionally known carriers may be used. Stated specifically, particles formed of metals such as iron, nickel, cobalt, manganese, chromium and rare earth elements, and alloys or oxides thereof, having been surface-oxidized or unoxidized and having an average particle diameter of from 20 to 300 pin, may be used. Also, it is preferable to use carriers comprising such carrier particles to or on the surfaces of which a material such as a styrene resin, an acrylic resin, a silicone resin, a fluorine resin or a polyester resin has been made to adhere or coated.

Magnetic Toner

The toner for developing electrostatic latent images according to the present invention may also be made usable as a magnetic toner by incorporating a magnetic material into toner particles. In this case, the magnetic material may also be made to serve as the colorant. The magnetic material used here may include iron oxides such as magnetite, hematite and ferrite; magnetic metals such as iron, cobalt and nickel, or alloys of any of these metals with a metal such as aluminum, cobalt, copper, lead, magnesium, tin, zinc, antimony, beryllium, bismuth, cadmium, calcium, manganese, selenium, titanium, tungsten or vanadium, and mixtures of any of these. As these magnetic material usable in the present invention, those having an average particle diameter of from 2 $\mu$m or less, and preferably approximately from 0.1 to 0.5 $\mu$m, are preferred. As its quantity in which it is incorporated in the toner, it may preferably be used in an amount of from 20 to 200 parts by weight based on 100 parts by weight of the binder resin, and particularly in an amount of from 40 to 150 parts by weight based on 100 parts by weight of the binder resin.

In order to achieve much higher image quality, it must be made possible to develop finer latent image dots faithfully. For that end, it is preferable that, e.g., the toner for developing electrostatic latent images according to the present invention has toner particles so regulated as to have a weight-average particle diameter of from 4 $\mu$m to 9 $\mu$m. Namely, toner particles having a weight-average particle diameter smaller than 4 $\mu$m are not preferable because they may cause a lowering of transfer efficiency and hence transfer residual toner tends to remain on the photosensitive member in a large quantity, tending to cause non-uniform or uneven images due to fog and faulty transfer. Also, toner particles having a weight-average particle diameter larger than 9 $\mu$m tend to cause spots around characters or line images.

In the present invention, the average particle diameter and particle size distribution of the toner are measured with a Coulter counter Model TA-II or Coulter Multisizer (manufactured by Coulter Electronics, Inc.). An interface (manufactured by Nikkaki k.k.) that outputs number distribution and volume distribution and a personal computer PC9801 (manufactured by NEC.) are connected. As an electrolytic solution used in the measurement, an aqueous 1% NaCl solution is prepared using first-grade sodium chloride. For example, commercially available, ISOTON R-II (available from Coulter Scientific Japan Co.) may be used. As a specific method, measurement is made by adding as a dispersant from 0.1 to 5 mL of a surface active agent (preferably an alkylbenzene sulfonate) to from 100 to 150 ml of the above aqueous electrolytic solution, and further adding from 2 to 20 mg of a sample to be measured. The electrolytic solution in which the sample has been suspended is subjected to dispersion for about 1 minute to about 3 minutes in an ultrasonic dispersion machine. The volume distribution and number distribution are calculated by measuring the volume and number of toner particles with particle diameters of not smaller than 2 $\mu$m by means of the above Coulter counter Model TA-II, using an aperture of 100 $\mu$m as its aperture. Then the values according to the present invention are determined, which are the volume-based, weight-average particle diameter (D4) determined from the volume distribution and the number-based, number-average particle diameter (D1) determined from number distribution.

Charge Quantity

The toner for developing electrostatic latent images according to the present invention may preferably have a charge quantity (two-component method) per unit weight, of from −10 to −80 $\mu$C/g, and more preferably from −15 to −70 $\mu$C/g. This is preferable in order to improve transfer efficiency in a transfer method making use of a transfer member to which a voltage is kept applied.

Figure 10:
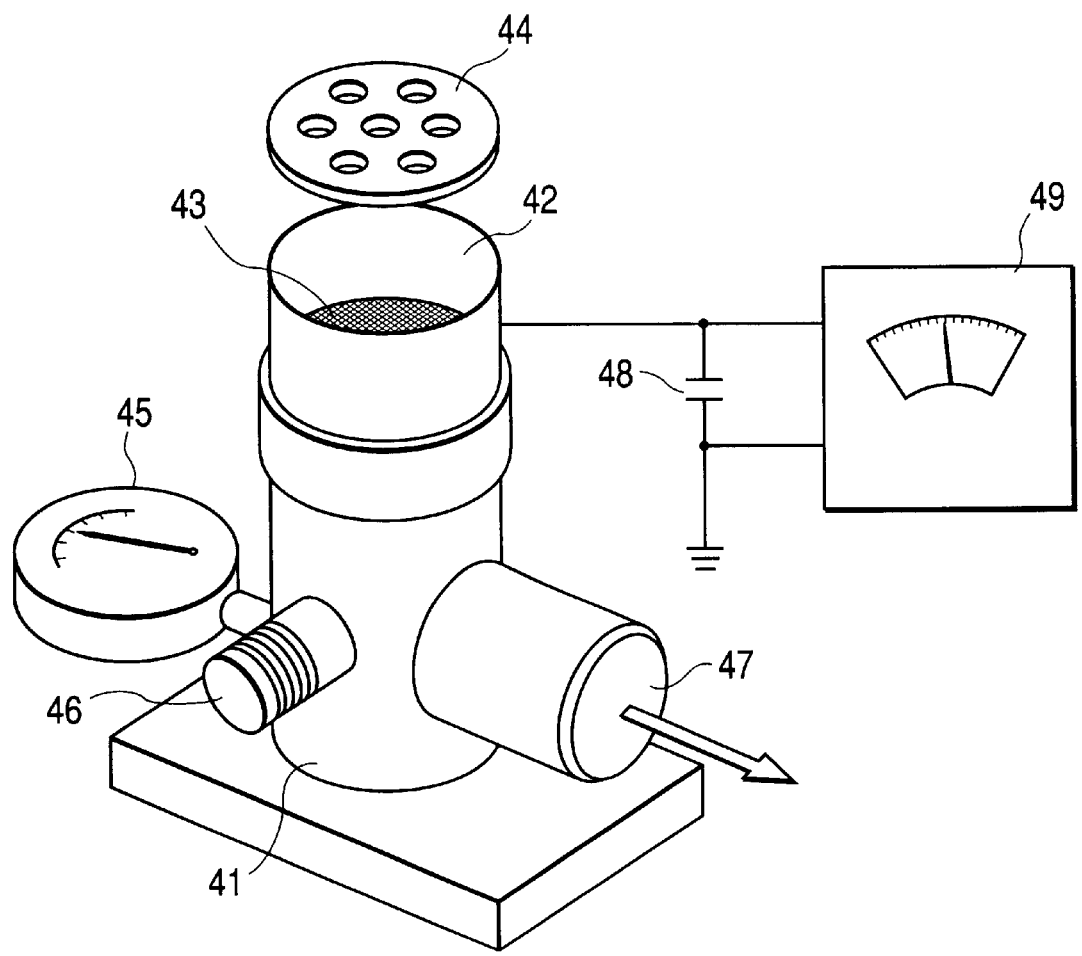
FIG. 10 is a diagrammatic illustration of a blow-off charge quantity measuring unit with which the charge quantity of toners is measured.

A method of measuring the charge quantity quantity (two-component triboelectricity) by the two-component method used in the present invention is described below. In the measurement, a charge quantity measuring device shown in FIG. 10 is used.

First, in a fixed environment and using an iron powder EFV200/300 (available from Powder Teck Co.) as the carrier, a mixture prepared by adding 0.5 g of the measuring-object toner to 9.5 g of the carrier is put in a bottle with a volume of 50 to 100 mL, made of polyethylene, and is set on a shaker having a fixed shaking width, followed by shaking for a fixed time, setting shaking conditions at a shaking width of 100 mm and a shaking speed of 100 to-and-fro times per minute. Then, the resulting mixture is put in a measuring container 42 made of a metal at the bottom of which a screen 43 of 500 meshes is provided, and the container is covered with a plate 44 made of a metal. The total weight of the measuring container 42 at this time is weighed and is expressed as W1 (g). Next, in a suction device (not shown; made of an insulating material at least at the part coming into contact with the measuring container 42), air is sucked from a suction opening 47 and an air-flow control valve 46 is operated to control the pressure indicated by a vacuum indicator 45 to be 2,450 Pa (250 mmAq). In this state, suction is carried out for 1 minute to remove the toner by suction. The potential indicated by a potentiometer 49 at this time is expressed as V (volt). Herein, numeral 48 denotes a capacitor, whose capacitance is expressed as C ($\mu$F). The total weight of the measuring container after completion of the suction is also weighed and is expressed as W2 (g). The quantity of triboelectricity ($\mu$C/g) of the toner is calculated from these measured values according to the following expression.

Quantity of triboelectricity ($\mu$C/g)=C×V/(W1−W2)

Molecular Weight Distribution of Binder Resin

The binder resin used as a constituent material of the toner for developing electrostatic latent images according to the present invention may preferably be made to have, in its molecular weight distribution as measured by GPC, a peak in the range of from 3,000 to 150,000 in the low-molecular weight region especially when the toner is produced by pulverization. Namely, if the binder resin has the GPC peak at more than 150,000 in the low-molecular weight region, it may be difficult to obtain a toner improved sufficiently in transfer efficiency. Also, the use of a binder resin having the GPC peak at less than 3,000 in the low-molecular weight region is not preferable because it tends to cause melt adhesion when toner particles are surface-treated.

In the present invention, the molecular weight of the binder resin is measured by GPC (gel permeation chromatography). As a specific method for measurement by GPC, a sample obtained by beforehand subjecting the toner to extraction with a THF (tetrahydrofuran) solvent for 20 hours by means of a Soxhlet extractor is used for the measurement. As column constitution, A-801, A-802, A-803, A-804, A-805, A-806 and A-807, available from Showa Denko K.K., are connected, and the molecular weight distribution is measured using a calibration curve of standard polystyrene resin.

In the present invention, it is also preferable to use as the binder resin a binder resin having a ratio of weight-average molecular weight (Mw) to number-average molecular weight (Mn), Mw/Mn, of from 2 to 100, as measured in the manner as described above.

Glass Transition Point of Toner

It is further preferable for the toner of the present invention to be so prepared as to have a glass transition point Tg of from 40° C. to 75° C., and more preferably from 52° C. to 70° C., in view of fixing performance and storage stability. The glass transition point Tg in this case may be measured with, e.g., a differential scanning calorimeter of a highly precise, inner-heat input compensation type, such as DSC-7, manufactured by Perkin Elmer Co. It is measured according to ASTM D3418-82. In the present invention, a measuring sample is once heated to take a previous history and thereafter cooled rapidly. Then, the sample is again heated at a heating rate of 10° C./min. within the temperature range of 0 to 200° C., where the DSC curve thus measured may be used.

Image-forming Method

The toner for developing electrostatic latent images according to the present invention, constituted as described above, may particularly preferably be applied to;

an image-forming method comprising a charging step of applying a voltage to a charging member from its outside to charge an electrostatic-latent-image-bearing member electrostatically; a latent-image-forming step of forming an electrostatic latent image on the electrostatic-latent-image-bearing member thus charged; a developing step of developing the electrostatic latent image by the use of a toner to form a toner image on the electrostatic-latent-image-bearing member; a transfer step of transferring to a recording medium the toner image formed on the electrostatic-latent-image-bearing member; and a heat fixing step of fixing by heat the toner image held on the recording medium; or an image-forming method in which the transfer step comprises a first transfer step of transferring to an intermediate transfer member the toner image formed on the electrostatic-latent-image-bearing member and a second transfer step of transferring to a recording medium the toner image held on the intermediate transfer member.

EXAMPLES

Examples are given below. In the following, "%" is by weight unless particularly noted.

Example 1

In 200 mL of M9 medium containing 0.5% of D-glucose and 0.1% of thienoylhexanoic acid (hereinafter "ToHxA"), *Pseudomonas cichorii* strain YN2 was inoculated to effect shaking culture at 30° C. and 125 strokes/minute. After 50 hours, the bacterial body was collected by centrifugation, and then again suspended in 200 mL of M9 medium containing 0.5% of D-glucose and 0.1% of ToHxA and not containing any nitrogen source ($NH_4Cl$), further followed by shaking culture at 30° C. and 125 strokes/minute. After 37 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 $\mu$m in pore diameter, and thereafter concentrated by means of a rotary evaporator. The concentrated liquid was re-precipitated with cold methanol, and further only the precipitate formed was collected, followed by vacuum drying to obtain a PHA.

The PHA thus obtained was analyzed with an NMR instrument (FT-NMR: Bruker DPX400) under the following conditions.

Measurement nuclide: $^1$H.
Solvent used: CDCl$_3$.
Reference: Capillary-encapsulated TMS/CDCl$_3$.
Measurement temperature: room temperature.

The $^1$H-NMR spectrum chart and the results of its identification (see Chemical Formula 13) are shown in FIG. 1 and Table 1, respectively.

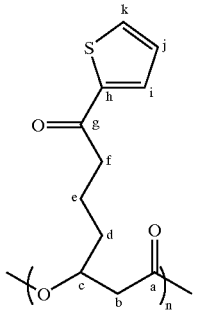

(13)

TABLE 1

| Chemical shift (ppm) | Integral ratio | splitting | Identification results |
|---|---|---|---|
| 1.68 | 4 | m | d, e |
| 2.50 to 2.63 | 2 | m | b |
| 2.83 to 2.96 | 2 | m | f |
| 5.22 | 1 | m | c |
| 7.07 | 1 | T | j |
| 7.56 | 1 | D | k |
| 7.71 | 1 | D | i |

Figure 2:
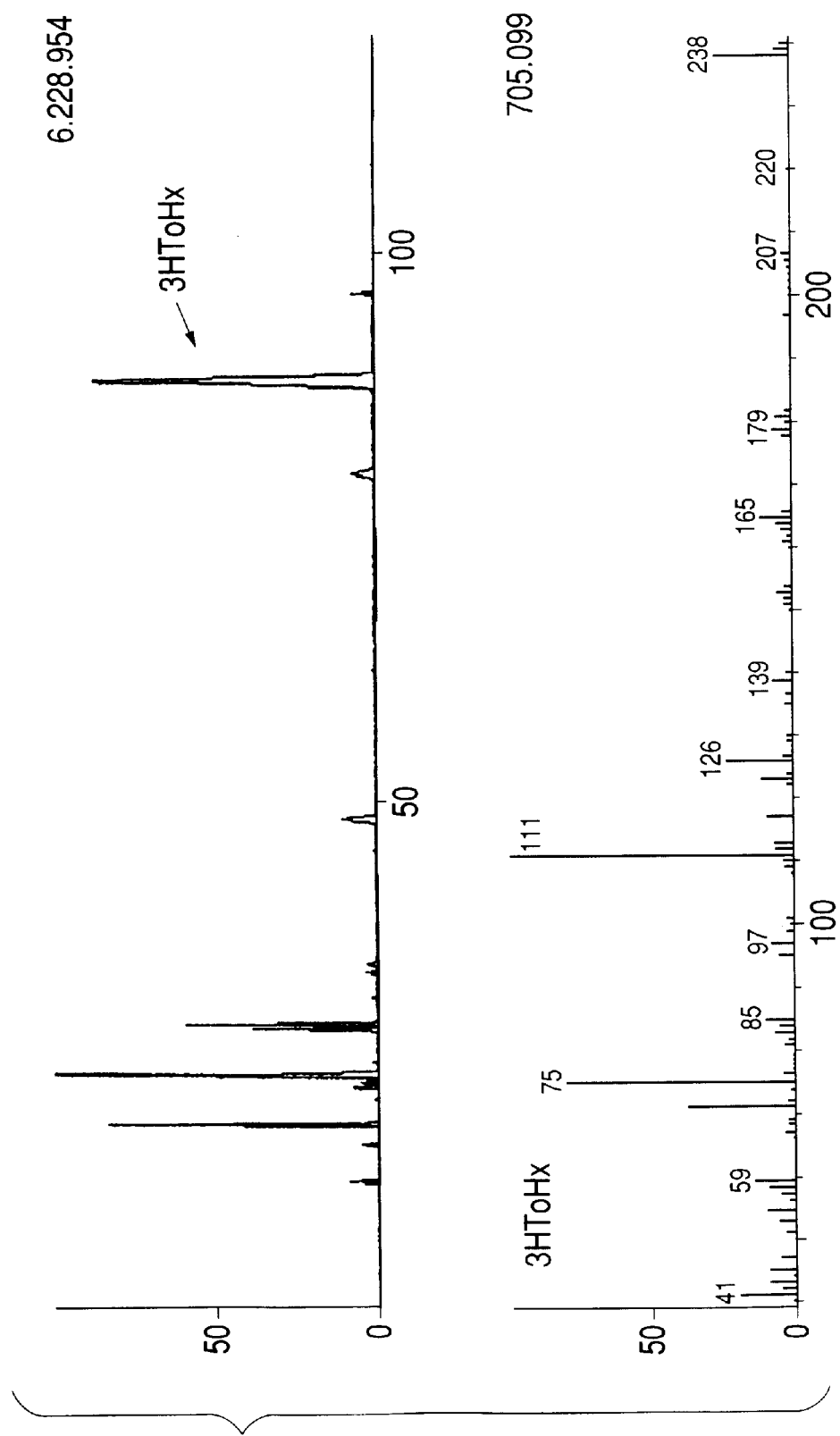
FIG. 2 is a GC-MS chart of a methylated decomposition product of the polymer in Example 1.

The PHA thus obtained was subjected to methanolysis by a conventional method, and thereafter analyzed with a gas chromatography mass spectrometer (GC-MS, Shimadzu QP-5050, EI method) to make identification of the methyl-esterified product of the PHA monomer unit. As a result, as shown in FIG. 2 and Table 2, it was ascertained that the PHA was a PHA containing 3-hydroxy-6-(2-thienoyl)hexanoic acid (hereinafter often "3HToHx") as a monomer unit.

TABLE 2

| Production of PHA by *Pseudomonas cichorii* Strain YN2 | |
|---|---|
| Bacterial-body dry weight | 680 mg/L |
| Polymer dry weight | 180 mg/L |
| Monomer unit composition (GC-MS, TIC peak area ratio): | |
| 3-Hydroxyhexanoic acid | 1% |
| 3-Hydroxyoctanoic acid | 7% |
| 3-Hydroxydecanoic acid | 8% |
| 3-Hydroxydodecanoic acid | 3% |
| 3-Hydroxydodecenoic acid | 6% |
| 3-Hydroxy-6-(2-thienoyl)hexanoic acid | 75% |

TIC: total ion chromatography

The molecular weight of this PHA was also measured by gel permeation chromatography (GPC: Toso HLC-8020; column: Polymer Laboratory PLgel MIXED-C, 5 µm; solvent: chloroform; in terms of polystyrene). As a result, the PHA was found to have Mn (number-average molecular weight) of 39,000 and Mw (weight-average molecular weight) of 110,000.

Example 2

In 200 mL of M9 medium containing 0.5% of D-glucose and 0.1% of ToHxA, *Pseudomonas cichorii* strain H45 was inoculated to effect shaking culture at 30° C. and 125 strokes/minute. After 50 hours, the bacterial body was collected by centrifugation, and then again suspended in 200 mL of M9 medium containing 0.5% of D-glucose and 0.1% of ToHxA and not containing any nitrogen source (NH$_4$Cl), further followed by shaking culture at 30° C. and 125 strokes/minute. After 37 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 µm in pore diameter, and thereafter concentrated by means of a rotary evaporator. The concentrated liquid was re-precipitated with cold methanol, and further only the precipitate formed was collected, followed by vacuum drying to obtain a PHA.

The PHA thus obtained was subjected to methanolysis by a conventional method, and thereafter analyzed with a gas chromatography mass spectrometer (GC-MS, Shimadzu QP-5050, EI method) to make identification of the methyl-esterified product of the PHA monomer unit. As a result, as shown in Table 3, it was ascertained that the PHA was a PHA containing 3HToHx as a monomer unit.

TABLE 3

| Production of PHA by *Pseudomonas cichorii* Strain H45 | |
|---|---|
| Bacterial-body dry weight | 520 mg/L |
| Polymer dry weight | 58 mg/L |
| Monomer unit composition (GC-MS, TIC peak area ratio): | |
| 3-Hydroxybutyric acid | 1% |
| 3-Hydroxyhexanoic acid | 4% |
| 3-Hydroxyoctanoic acid | 38% |
| 3-Hydroxydecanoic acid | 27% |
| 3-Hydroxydodecanoic acid | 5% |
| 3-Hydroxydodecenoic acid | 10% |
| 3-Hydroxy-6-(2-thienoyl)hexanoic acid | 15% |

Example 3

In 200 mL of M9 medium containing 0.5% of D-glucose and 0.1% of ToHxA, *Pseudomonas jessenii* strain P161 was inoculated to effect shaking culture at 30° C. and 125 strokes/minute. After 50 hours, the bacterial body was collected by centrifugation, and then again suspended in 200 mL of M9 medium containing 0.5% of D-glucose and 0.1% of ToHxA and not containing any nitrogen source (NH$_4$Cl), further followed by shaking culture at 30° C. and 125 strokes/minute. After 37 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 µm in pore diameter, and thereafter concentrated by means of a rotary evaporator. The concentrated liquid was re-precipitated with cold methanol, and further only the precipitate formed was collected, followed by vacuum drying to obtain a PHA.

The PHA thus obtained was subjected to methanolysis by a conventional method, and thereafter analyzed with a gas chromatography mass spectrometer (GC-MS, Shimadzu QP-5050, EI method) to make identification of the methyl-esterified product of the PHA monomer unit. As a result, as shown in Table 4, it was ascertained that the PHA was a PHA containing 3HToHx as a monomer unit.

TABLE 4

Production of PHA by *Pseudomonas jessenii* Strain P161

| | |
|---|---|
| Bacterial-body dry weight | 470 mg/L |
| Polymer dry weight | 100 mg/L |
| Monomer unit composition (GC-MS, TIC peak area ratio): | |
| 3-Hydroxyhexanoic acid | 1% |
| 3-Hydroxyoctanoic acid | 7% |
| 3-Hydroxydecanoic acid | 6% |
| 3-Hydroxydodecanoic acid | 1% |
| 3-Hydroxydodecenoic acid | 2% |
| 3-Hydroxy-6-(2-thienoyl)hexanoic acid | 83% |

The molecular weight of this PHA was also measured by gel permeation chromatography (GPC: Toso HLC-8020; column: Polymer Laboratory PLgel MIXED-C, 5 µm; solvent: chloroform; in terms of polystyrene). As a result, the PHA was found to have Mn of 23,000 and Mw of 51,000.

Example 4

In 200 mL of M9 medium containing 0.5% of D-glucose and 0.1% of thienoylvaleric acid (hereinafter "ToVA"), *Pseudomonas cichorii* strain YN2 was inoculated to effect shaking culture at 30° C. and 125 strokes/minute. After 63 hours, the bacterial body was collected by centrifugation, and then again suspended in 200 mL of M9 medium containing 0.5% of D-glucose and 0.1% of ToVA and not containing any nitrogen source (NH$_4$Cl), further followed by shaking culture at 30° C. and 125 strokes/minute. After 64 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 µm in pore diameter, and thereafter concentrated by means of a rotary evaporator. The concentrated liquid was re-precipitated with cold methanol, and further only the precipitate formed was collected, followed by vacuum drying to obtain a PHA.

Figure 3:
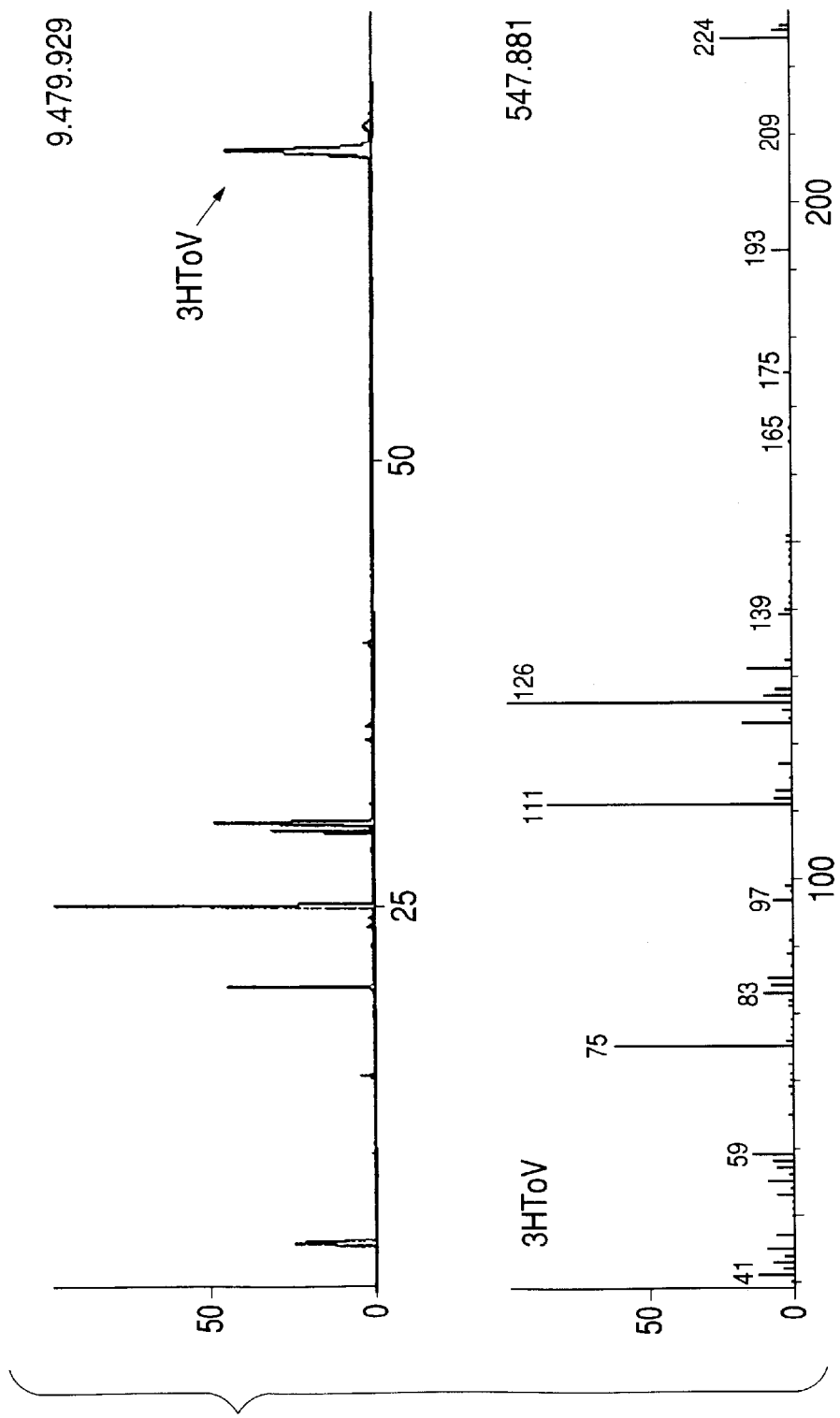
FIG. 3 is a GC-MS chart of a methylated decomposition product of a polymer in Example 5.

The PHA thus obtained was subjected to methanolysis by a conventional method, and thereafter analyzed with a gas chromatography mass spectrometer (GC-MS, Shimadzu QP-5050, EI method) to make identification of the methyl-esterified product of the PHA monomer unit. As a result, as shown in FIG. 3 and Table 5, it was ascertained that the PHA was a PHA containing 3-hydroxy-5-(2-thienoyl)valeric acid (hereinafter often "3HToV") as a monomer unit.

TABLE 5

Production of PHA by *Pseudomonas cichorii* Strain YN2

| | |
|---|---|
| Bacterial-body dry weight | 1,100 mg/L |
| Polymer dry weight | 120 mg/L |
| Monomer unit composition (GC-MS, TIC peak area ratio): | |
| 3-Hydroxyhexanoic acid | 1% |
| 3-Hydroxyoctanoic acid | 8% |
| 3-Hydroxydecanoic acid | 18% |
| 3-Hydroxydodecanoic acid | 6% |
| 3-Hydroxydodecenoic acid | 10% |
| 3-Hydroxy-5-(2-thienoyl)valeric acid | 57% |

The molecular weight of this PHA was also measured by gel permeation chromatography (GPC: Toso HLC-8020; column: Polymer Laboratory PLgel MIXED-C, 5 µm; solvent: chloroform; in terms of polystyrene). As a result, the PHA was found to have Mn of 110,000 and Mw of 260,000.

Example 5

In 200 mL of M9 medium containing 0.5% of D-glucose and 0.1% of ToVA, *Pseudomonas cichorii* strain H45 was inoculated to effect shaking culture at 30° C. and 125 strokes/minute. After 63 hours, the bacterial body was collected by centrifugation, and then again suspended in 200 mL of M9 medium containing 0.5% of D-glucose and 0.1% of ToVA and not containing any nitrogen source (NH$_4$Cl), further followed by shaking culture at 30° C. and 125 strokes/minute. After 64 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 µm in pore diameter, and thereafter concentrated by means of a rotary evaporator. The concentrated liquid was re-precipitated with cold methanol, and further only the precipitate formed was collected, followed by vacuum drying to obtain a PHA.

The PHA thus obtained was subjected to methanolysis by a conventional method, and thereafter analyzed with a gas chromatography mass spectrometer (GC-MS, Shimadzu QP-5050, EI method) to make identification of the methyl-esterified product of the PHA monomer unit. As a result, as shown in Table 6, it was ascertained that the PHA was a PHA containing 3HToV as a monomer unit.

TABLE 6

Production of PHA by *Pseudomonas cichorii* Strain H45

| | |
|---|---|
| Bacterial-body dry weight | 460 mg/L |
| Polymer dry weight | 5 mg/L |
| Monomer unit composition (GC-MS, TIC peak area ratio): | |
| 3-Hydroxyoctanoic acid | 7% |
| 3-Hydroxydecanoic acid | 6% |
| 3-Hydroxydodecanoic acid | 1% |
| 3-Hydroxy-5-(2-thienoyl)valeric acid | 86% |

Example 6

In 200 mL of M9 medium containing 0.5% of D-glucose and 0.1% of ToVA, *Pseudomonas jessenii* strain P161 was inoculated to effect shaking culture at 30° C. and 125 strokes/minute. After 63 hours, the bacterial body was collected by centrifugation, and then again suspended in 200 mL of M9 medium containing 0.5% of D-glucose and 0.1% of ToVA and not containing any nitrogen source (NH$_4$Cl), further followed by shaking culture at 30° C. and 125 strokes/minute. After 64 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 µm in pore diameter, and thereafter concentrated by means of a rotary evaporator. The concentrated liquid was re-precipitated with cold methanol, and further only the precipitate formed was collected, followed by vacuum drying to obtain a PHA.

The PHA thus obtained was subjected to methanolysis by a conventional method, and thereafter analyzed with a gas chromatography mass spectrometer (GC-MS, Shimadzu QP-5050, EI method) to make identification of the methyl-esterified product of the PHA monomer unit. As a result, as shown in Table 7, it was ascertained that the PHA was a PHA containing 3HToV as a monomer unit.

TABLE 7

Production of PHA by *Pseudomonas cichorii* Strain YN2

| | |
|---|---|
| Bacterial-body dry weight | 510 mg/L |
| Polymer dry weight | 30 mg/L |
| Monomer unit composition (GC-MS, TIC peak area ratio): | |
| 3-Hydroxyhexanoic acid | 1% |
| 3-Hydroxyoctanoic acid | 11% |
| 3-Hydroxydecanoic acid | 22% |
| 3-Hydroxydodecanoic acid | 6% |
| 3-Hydroxydodecenoic acid | 7% |
| 3-Hydroxy-5-(2-thienoyl)valeric acid | 53% |

Example 7

In 200 mL of M9 medium containing 0.5% of D-glucose and 0.1% of ToVA, *Pseudomonas cichorii* strain YN2 was inoculated to effect shaking culture at 30° C. and 125 strokes/minute. After 63 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain a PHA.

The PHA thus obtained was subjected to methanolysis by a conventional method, and thereafter analyzed with a gas chromatography mass spectrometer (GC-MS, Shimadzu QP-5050, EI method) to make identification of the methyl-esterified product of the PHA monomer unit. As a result, as shown in Table 8, it was ascertained that the PHA was a PHA containing 3HToV as a monomer unit.

TABLE 8

Production of PHA by *Pseudomonas cichorii* Strain YN2

| | |
|---|---|
| Bacterial-body dry weight | 390 mg/L |
| Polymer dry weight | 2 mg/L |
| Monomer unit composition (GC-MS, TIC peak area ratio): | |
| 3-Hydroxyoctanoic acid | 3% |
| 3-Hydroxydecanoic acid | 5% |
| 3-Hydroxydodecanoic acid | 3% |
| 3-Hydroxydodecenoic acid | 9% |
| 3-Hydroxy-5-(2-thienoyl)valeric acid | 80% |

Example 8

In 200 mL of M9 medium containing 0.5% of polypeptone (Nippon Seiyaku K.K.) and 0.1% of ToVA, *Pseudomonas cichorii* strain YN2 was inoculated to effect shaking culture at 30° C. and 125 strokes/minute. After 63 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain a PHA.

The PHA thus obtained was subjected to methanolysis by a conventional method, and thereafter analyzed with a gas chromatography mass spectrometer (GC-MS, Shimadzu QP-5050, EI method) to make identification of the methyl-esterified product of the PHA monomer unit. As a result, as shown in Table 9, it was ascertained that the PHA was a PHA containing 3HToV as a monomer unit.

TABLE 9

Production of PHA by *Pseudomonas cichorii* Strain YN2

| | |
|---|---|
| Bacterial-body dry weight | 390 mg/L |
| Polymer dry weight | 2 mg/L |
| Monomer unit composition (GC-MS, TIC peak area ratio): | |
| 3-Hydroxybutyric acid | 73% |
| 3-Hydroxy-5-(2-thienoyl)valeric acid | 27% |

Example 9

In 200 mL of M9 medium containing 0.5% of yeast extract (Difco) and 0.1% of ToVA, *Pseudomonas cichorii* strain YN2 was inoculated to effect shaking culture at 30° C. and 125 strokes/minute. After 63 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain a PHA.

The PHA thus obtained was subjected to methanolysis by a conventional method, and thereafter analyzed with a gas chromatography mass spectrometer (GC-MS, Shimadzu QP-5050, EI method) to make identification of the methyl-esterified product of the PHA monomer unit. As a result, as shown in Table 10, it was ascertained that the PHA was a PHA containing 3HToV as a monomer unit.

TABLE 10

Production of PHA by *Pseudomonas cichorii* Strain YN2

| | |
|---|---|
| Bacterial-body dry weight | 650 mg/L |
| Polymer dry weight | 2 mg/L |
| Monomer unit composition (GC-MS, TIC peak area ratio): | |
| 3-Hydroxybutyric acid | 27% |
| 3-Hydroxyoctanoic acid | 2% |
| 3-Hydroxynonanoic acid | 2% |
| 3-Hydroxydecanoic acid | 3% |
| 3-Hydroxy-5-(2-thienoyl)valeric acid | 66% |

Example 10

In 200 mL of M9 medium containing 0.5% of sodium malate and 0.1% of ToVA, *Pseudomonas cichorii* strain YN2 was inoculated to effect shaking culture at 30° C. and 125 strokes/minute. After 63 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain a PHA.

The PHA thus obtained was subjected to methanolysis by a conventional method, and thereafter analyzed with a gas chromatography mass spectrometer (GC-MS, Shimadzu QP-5050, EI method) to make identification of the methyl-esterified product of the PHA monomer unit. As a result, as shown in Table 11, it was ascertained that the PHA was a PHA containing 3HToV as a monomer unit.

TABLE 11

| Production of PHA by *Pseudomonas cichorii* Strain YN2 | |
|---|---|
| Bacterial-body dry weight | 470 mg/L |
| Polymer dry weight | 2 mg/L |
| Monomer unit composition (GC-MS, TIC peak area ratio): | |
| 3-Hydroxybutyric acid | 6% |
| 3-Hydroxyheptanoic acid | 1% |
| 3-Hydroxyoctanoic acid | 3% |
| 3-Hydroxynonanoic acid | 5% |
| 3-Hydroxydecanoic acid | 2% |
| 3-Hydroxy-5-(2-thienoyl)valeric acid | 83% |

Example 11

In 200 mL of M9 medium containing 0.5% of D-glucose and 0.1% of thienoylhexane (hereinafter "ToHx"), *Pseudomonas cichorii* strain YN2 was inoculated to effect shaking culture at 30° C. and 125 strokes/minute. After 48 hours, the bacterial body was collected by centrifugation, and then again suspended in 200 mL of M9 medium containing 0.5% of D-glucose and 0.1% of ToHx and not containing any nitrogen source ($NH_4Cl$), further followed by shaking culture at 30° C. and 125 strokes/minute. After 46 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain a PHA.

The PHA thus obtained was subjected to methanolysis by a conventional method, and thereafter analyzed with a gas chromatography mass spectrometer (GC-MS, Shimadzu QP-5050, EI method) to make identification of the methyl-esterified product of the PHA monomer unit. As a result, as shown in Table 12, it was ascertained that the PHA was a PHA containing 3HToHx as a monomer unit.

TABLE 12

| Production of PHA by *Pseudomonas cichorii* Strain YN2 | |
|---|---|
| Bacterial-body dry weight | 520 mg/L |
| Polymer dry weight | 100 mg/L |
| Monomer unit composition (GC-MS, TIC peak area ratio): | |
| 3-Hydroxybutyric acid | 3% |
| 3-Hydroxyhexanoic acid | 1% |
| 3-Hydroxyheptanoic acid | 4% |
| 3-Hydroxyoctanoic acid | 10% |

TABLE 12-continued

| Production of PHA by *Pseudomonas cichorii* Strain YN2 | |
|---|---|
| 3-Hydroxydecanoic acid | 36% |
| 3-Hydroxyundecanoic acid | 1% |
| 3-Hydroxydodecanoic acid | 15% |
| 3-Hydroxydodecenoic acid | 23% |
| 3-Hydroxytetradecanoic acid | 2% |
| 3-Hydroxy-6-(2-thienoyl)hexanoic acid | 5% |

Example 12

In 200 mL of M9 medium containing 0.5% of D-glucose and 0.1% of ToHx, *Pseudomonas cichorii* strain YN2 was inoculated to effect shaking culture at 30° C. and 125 strokes/minute. After 48 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain a PHA.

The PHA thus obtained was subjected to methanolysis by a conventional method, and thereafter analyzed with a gas chromatography mass spectrometer (GC-MS, Shimadzu QP-5050, EI method) to make identification of the methyl-esterified product of the PHA monomer unit. As a result, as shown in Table 13, it was ascertained that the PHA was a PHA containing 3HToHx as a monomer unit.

TABLE 13

| Production of PHA by *Pseudomonas cichorii* Strain YN2 | |
|---|---|
| Bacterial-body dry weight | 480 mg/L |
| Polymer dry weight | 47 mg/L |
| Monomer unit composition (GC-MS, TIC peak area ratio): | |
| 3-Hydroxybutyric acid | 6% |
| 3-Hydroxyhexanoic acid | 1% |
| 3-Hydroxyheptanoic acid | 23% |
| 3-Hydroxyoctanoic acid | 12% |
| 3-Hydroxynonanoic acid | 1% |
| 3-Hydroxydecanoic acid | 23% |
| 3-Hydroxyundecanoic acid | 1% |
| 3-Hydroxydodecanoic acid | 11% |
| 3-Hydroxydodecenoic acid | 1% |
| 3-Hydroxytetradecanoic acid | 1% |
| 3-Hydroxy-6-(2-thienoyl)hexanoic acid | 20% |

Example 13

In 200 mL of M9 medium containing 0.5% of polypeptone (Nippon Seiyaku K.K.) and 0.1% of ToHx, *Pseudomonas cichorii* strain YN2 was inoculated to effect shaking culture at 30° C. and 125 strokes/minute. After 68 hours, the bacterial body was collected by centrifugation, and then washed once with cold methanol, followed by freeze-drying.

The resultant freeze-dried pellets were suspended in 20 mL of chloroform, which were then stirred at 60° C. for 20 hours to extract a PHA. The liquid extract obtained was filtered with a membrane filter of 0.45 μm in pore diameter, and thereafter concentrated by means of a rotary evaporator. The concentrated liquid was re-precipitated with cold methanol, and further only the precipitate formed was collected, followed by vacuum drying to obtain a PHA.

The PHA thus obtained was subjected to methanolysis by a conventional method, and thereafter analyzed with a gas chromatography mass spectrometer (GC-MS, Shimadzu QP-5050, EI method) to make identification of the methyl-esterified product of the PHA monomer unit. As a result, as shown in Table 14, it was ascertained that the PHA was a PHA containing 3HToHx as a monomer unit.

TABLE 14

Production of PHA by *Pseudomonas cichorii* Strain YN2

| | |
|---|---|
| Bacterial-body dry weight | 530 mg/L |
| Polymer dry weight | 28 mg/L |
| Monomer unit composition (GC-MS, TIC peak area ratio): | |
| 3-Hydroxybutyric acid | 46% |
| 3-Hydroxyhexanoic acid | 1% |
| 3-Hydroxyheptanoic acid | 21% |
| 3-Hydroxyoctanoic acid | 12% |
| 3-Hydroxynonanoic acid | 1% |
| 3-Hydroxydecanoic acid | 10% |
| 3-Hydroxydodecanoic acid | 3% |
| 3-Hydroxy-6-(2-thienoyl)hexanoic acid | 6% |

Example 14

To 500 mL volume shaking flask, M9 medium containing 0.5% of yeast extract (Difco) was added, and *Pseudomonas cichorii* strain YN2 (FERM BP-7375) was inoculated therein to effect shaking culture at 30° C. for 8 hours. Into a 2 L volume shaking flask, 1 L of M9 medium containing 0.5% of D-glucose (Kishida Chemical Co., Ltd.) and 0.1% of 5-(2-thienyl)valeric acid were charged, on which two sets were prepared for use. To these flasks, 2 mL each of the culture solution in which the strain YN2 was previously cultured was added to effect shaking culture at 30° C. and 125 strokes/minute.

After 48 hours, the bacterial body was collected by centrifugation. Into a 2 L volume shaking flask, 1 L of M9 medium containing 0.5% of D-glucose (Kishida Chemical Co., Ltd) and 0.1% of 5-(2-thienyl)valeric acid and not containing any nitrogen source ($NH_4Cl$) was charged, on which two sets were prepared for use. The bacterial body having been collected was again suspended therein, and was further cultured at 30° C. and 125 strokes/minute. After 48 hours, the bacterial body was collected by centrifugation, and was again suspended in 400 mL of deionized water, followed by centrifugation, which was then again suspended in 80 mL of deionized water. To the suspension formed, 40 mL of a sodium hypochlorite (Kishida Chemical Co., Ltd.; containing about 12% NaClO at the time of manufacture; active chlorine: 5% or more) to carry out reaction at 4° C. with stirring. After 2 hours, 240 mL of deionized water was added, followed by centrifugation (4° C., 29,400 m/s2 (=3,000 G), 30 minutes), and then the precipitated component was collected. The precipitate thus collected was again suspended in 150 mL of deionized water, followed by centrifugation (4° C., 29,400 m/s2 (=3,000 G), 30 minutes) and then washing. This washing operation was further repeated twice, and the precipitate obtained was freeze-dried. The resultant freeze-dried samples were each in a weight of 1,580 mg.

Using one of the samples thus obtained, its molecular weight was measured by gel permeation chromatography (GPC). Conditions for the GPC were: apparatus: Toso HLC-8020; column: Polymer Laboratory PLgel MIXED-C, 5 μm, two columns; mobile-phase solvent: DMF containing 0.1% by weight of LiCl; and in terms of polystyrene.

Using the other sample, its structure was examined by methanolysis GC-MS. More specifically, about 10 mg of the sample was put into a 25 mL volume eggplant type flask, and dissolved in 2 mL of chloroform, followed by addition of 2 mL of a methanol solution containing 3% sulfuric acid to carry out reaction for 3.5 hours under reflux at 100° C. After the reaction was completed, 10 mL of deionized water was added to the reaction mixture, which was then vigorously shaked for 10 minutes. Thereafter, of the two layers separated, the lower layer chloroform layer was taken out, and then dehydrated with magnesium sulfate. Thereafter, this chloroform layer was put to a gas chromatography mass spectrometer (GC-MS, Shimadzu QP-5050, EI method) to make identification of the methyl-esterified product of a PHA monomer unit. Conditions for the GC-MS were: apparatus: Shimadzu QP-5050; column: J & W DB-WAXETR; ionization method: EI method.

As a result, the molecular weight measured by GPC was found to be number-average molecular weight (Mn)=55,000 and weight-average molecular weight (Mw)=131,000. Also, as to the unit percentage obtained from the results of the area ratio (%) of GC-MS total ion chromatography (TIC), a 3-hydroxy-5(2-thienyl)valeric acid unit was 97%, and 3-hydroxyoctanoic acid, 3-hydroxydecanoic acid and 3-hydroxydodecanoic acid were each 1%.

Example 15

Samples were obtained in the same manner as in Example 14 except that the strain YN2, which was the strain used in Example 14, was changed to *Pseudomonas cichorii* strain H45 (FERM BP-7374). The resultant freeze-dried samples were each in a weight of 480 mg.

On the samples thus obtained, molecular weight and structure were examined by GPC and GC-MS, respectively, in the same manner as in Example 14.

As a result, the molecular weight was found to be number-average molecular weight (Mn)=57,000 and weight-average molecular weight (Mw)=124,000. Also, as to the unit percentage determined from GC-MS data, a 3-hydroxy-5-(2-thienyl)valeric acid unit was 99%, and the remaining 1% was held by 3-hydroxyoctanoic acid.

Example 16

Samples were obtained in the same manner as in Example 14 except that the strain YN2, which was the strain used in Example 14, was changed to *Pseudomonas jessenii* strain P161 (FERM BP-7376). The resultant freeze-dried samples were each in a weight of 810 mg.

On the samples thus obtained, molecular weight and structure were examined by GPC and GC-MS, respectively, in the same manner as in Example 14.

As a result, the molecular weight was found to be number-average molecular weight (Mn)=55,000 and weight-average molecular weight (Mw)=128,000. Also, as to the unit percentage determined from GC-MS data, a 3-hydroxy-5-(2-thienyl)valeric acid unit was 98%, and 3-hydroxyoctanoic acid and 3-hydroxydecanoic acid were each 1%.

Example 17

To 500 mL volume shaking flask, M9 medium containing 0.5% of yeast extract (Difco) was added, and strain YN2 was inoculated therein to effect shaking culture at 30° C. for 8 hours. Into a 2 L volume shaking flask, 1 L of M9 medium containing 0.5% of polypeptone (Wako Pure Chemical Industries, Ltd.) and 0.1% of 6-(2-thienyl)hexanoic acid were charged, on which two sets were prepared for use. To these flasks, 2 mL each of the culture solution in which the strain YN2 was previously cultured was added to effect shaking culture at 30° C. and 125 strokes/minute. After 48 hours, the bacterial body was collected by centrifugation, and was again suspended in 400 mL of deionized water, followed by centrifugation, which was then again suspended in 80 mL of deionized water. Treatment with sodium hypochlorite, a series of washing treatment subsequent thereto and freeze-drying were carried out in the same manner as in Example 14. The resultant freeze-dried samples were each in a weight of 560 mg.

On the samples thus obtained, molecular weight and structure were examined by GPC and GC-MS, respectively, in the same manner as in Example 14.

As a result, the molecular weight was found to be number-average molecular weight (Mn)=53,000 and weight-average molecular weight (Mw)=121,000. Also, as to the unit percentage determined from GC-MS data, it was found that a 3-hydroxy-6-(2-thienyl)hexanoic acid unit was 80%, a 3-hydroxy-4-(2-thienyl)valeric acid unit was 4%, and the remaining 16% was held by 3-hydroxybutyric acid.

Example 18

To 500 mL volume shaking flask, M9 medium containing 0.5% of yeast extract was added, and strain YN2 was inoculated therein to effect shaking culture at 30° C. for 8 hours. Into a 2 L volume shaking flask, 1 L of M9 medium containing 0.5% of D-glucose and 0.1% of 5-(2-thienyl)valeric acid were charged, on which two sets were prepared for use. To these flasks, 2 mL each of the culture solution in which the strain YN2 was previously cultured was added to effect shaking culture at 30° C. and 125 strokes/minute.

After 60 hours, the bacterial body was collected by centrifugation. Into a 2 L volume shaking flask, 1 L of M9 medium containing 0.5% of D-glucose and 0.1% of 5-(2-thienyl)valeric acid and not containing any nitrogen source ($NH_4Cl$) was charged, on which two sets were prepared for use. The bacterial body having been collected was again suspended therein, and was further cultured at 30° C. and 125 strokes/minute. After 60 hours, the bacterial body was collected by centrifugation, and was again suspended in 400 mL of deionized water, followed by centrifugation, which was then again suspended in 80 mL of deionized water. Treatment with sodium hypochlorite, a series of washing treatment subsequent thereto and freeze-drying were carried out in the same manner as in Example 14. The resultant freeze-dried samples were each in a weight of 220 mg.

On the samples thus obtained, molecular weight and structure were examined by GPC and GC-MS, respectively, in the same manner as in Example 14.

As a result, the molecular weight was found to be number-average molecular weight (Mn)=98,000 and weight-average molecular weight (Mw)=199,000. Also, as to the unit percentage determined from GC-MS data, a 3-hydroxy-6-(2-thienyl)hexanoic acid unit was 57%. As other units, 3-hydroxyhexanoic acid was 1%, 3-hydroxyoctanoic acid was 8%, 3-hydroxydecanoic acid was 18%, 3-hydroxydodecanoic acid was 6% and 3-hydroxydodecenoic acid was 10%.

Example 19

To 500 mL volume shaking flask, M9 medium containing 0.5% of yeast extract was added, and strain P161 was inoculated therein to effect shaking culture at 30° C. for 8 hours. Into a 2 L volume shaking flask, 1 L of M9 medium containing 0.5% of D-glucose and 0.1% of 6-(2-thienyl) hexanoic acid were charged, on which two sets were prepared for use. To these flasks, 2 mL each of the culture solution in which the strain P161 was previously cultured was added to effect shaking culture at 30° C. and 125 strokes/minute.

After 50 hours, the bacterial body was collected by centrifugation. Into a 2 L volume shaking flask, 1 L of M9 medium containing 0.5% of D-glucose and 0.1% of 6-(2-thienyl)hexanoic acid and not containing any nitrogen source ($NH_4Cl$) was charged, on which two sets were prepared for use. The bacterial body having been collected was again suspended therein, and was further cultured at 30° C. and 125 strokes/minute. After 50 hours, the bacterial body was collected by centrifugation, and was again suspended in 400 mL of deionized water, followed by centrifugation, which was then again suspended in 80 mL of deionized water. Treatment with sodium hypochlorite, a series of washing treatment subsequent thereto and freeze-drying were carried out in the same manner as in Example 14. The resultant freeze-dried samples were each in a weight of 190 mg.

On the samples thus obtained, molecular weight and structure were examined by GPC and GC-MS, respectively, in the same manner as in Example 14.

As a result, the molecular weight was found to be number-average molecular weight (Mn)=38,000 and weight-average molecular weight (Mw)=89,000. Also, as to the unit percentage determined from GC-MS data, a 3-hydroxy-6-(2-thienyl)hexanoic acid unit was 83%. As other units, 3-hydroxyhexanoic acid was 1%, 3-hydroxyoctanoic acid was 7%, 3-hydroxydecanoic acid was 6%, 3-hydroxydodecanoic acid was 1% and 3-hydroxydodecenoic acid was 2%.

The compounds obtained in the Examples 14 to 19 were used as exemplified compounds (1) to (6) in the subsequent examples.

Example 20

First $Na_3PO_4$ aqueous solution was introduced into a 2 l flask with four necks equipped with a high speed agitator, TK-Homomixer, the rotary speed of the agitator was adjusted to 10,000 rpm, and the solution was heated to 60° C. Then $CaCl_2$ aqueous solution was added little by little to prepare a water-base dispersing medium containing a very small amount of difficultly water-soluble dispersant $Ca_3(PO_4)_2$.

On the other hand, the composition shown below was dispersed with a ball mill for 3 hours, and 10 parts by mass of surface tack eliminator (ester wax) and 10 parts by mass of polymerization initiator, 2,2'-azobis(2,4-dimethylvaleronitrile), were added to prepare a polymerizable monomer composition.

| | |
|---|---|
| Styrene monomer | 82 parts by mass |
| Ethylhexyl acrylate monomer | 18 parts by mass |
| Divinylbenzene monomer | 0.1 parts by mass |
| Cyan colorant (C.I. pigment Blue 15) | 6 parts by mass |
| Polyethylene oxide resin (molecular weight 3200, acid value 8) | 5 parts by mass |
| Exemplified compound (1) | 2 parts by mass |
| Then the polymerizable monomer composition | |

Then the polymerizable monomer composition obtained as above was introduced into the previously prepared water-base dispersing medium, and granulation was carried out while maintaining a rotary speed of 10,000 rpm. After that, the polymerizable monomer composition was reacted at 65° C. for 3 hours and polymerized at 80° C. for 6 hours while agitating the dispersion with paddle agitating elements, and the polymerization reaction was terminated. After terminating the reaction, the suspension was cooled, acid was added to dissolve the difficultly water-soluble dispersant $Ca_3(PO_4)_2$, and filtration, rinsing and drying were carried out to obtain blue polymer particles (1). When measuring the particle size of the obtained blue polymer particles (1) with Kolter Counter Multi-Sizer (by Kolter), the weight-average particle size was 7.4 μm and the amount of the fine powder (the existing rate of the particles of 3.17 μm or smaller in the number distribution) was 5.0% by number.

Then 1.3 parts by mass of finely powdered hydrophobic silica (BET: 270 $m^2/g$) having been treated with hexamethyldisilazane, as a flow improver, was externally attached to 100 parts by mass of the blue polymer particles (1) having been prepared as above by dry mixing with a Henschel mixer, to obtain blue toner (1) of this example. And 7 parts by mass of the blue toner (1) and 93 parts by mass of resin-coated magnetic ferrite carrier (average particle size: 45 μm) were mixed with each other to prepare a two-component blue developer (1) for magnetic brush development.

Examples 21 to 25

Blue toners (2) to (6) of the Examples 21 to 25 were obtained in the same manner as in the Example 20 except that 2.0 parts by mass of the exemplified compound (2) to (6) were used instead of the exemplified compound (1). The properties of the toners were determined in the same manner as in the Example 14 and the results are shown in Table 15. And a two-component blue developers (2) to (6) were obtained with this toner in the same manner as in the Example 20.

Comparative Example 1

Blue toner (7) of the Comparative Example 1 was obtained in the same manner as in the Example 20 except that none of the exemplified compounds were used. The properties of the toner were determined in the same manner as in the Example 14 and the results are shown in Table 15. And a two-component blue developer (7) of the Comparative Example 1 was obtained with this toner in the same manner as in the Example 20.

<Evaluation>

The amount of electrical charge of the toners was measured of two-component blue developers (1) to (6) obtained in the Examples 20 to 25 and two-component blue developer (7) obatained in the Comparative Example 1, respectively, after 10-second and 300-second agitation under the environmental conditions of normal temperature and humidity (25° C., 60% RH) and of high temperature and humidity (30° C., 80% RH) adopting the method of measuring the amount of electrical charge described above. Evaluation was made with the values obtained by rounding off the measured values of the amount of the two-component blow-off electrical charge to nearest tenth on the basis of the criteria below. The results are shown in Table 15 together.

(Charging Property)

AA: very good (–20 μC/g or less)
A: good (–19.9 to –10.0 μC/g)
B: practically permissible (–9.9 to –5.0 μC/g)
C: practically impermissible (–4.9 μC/g or more)

TABLE 15

Particle Size Distribution and Charging Property of Blue Toners (1) to (6)

| | Exemplified Compound No. | Toner No.: Blue | Particle Size Distribution Weight-Average Particle Size (μm) | Amount of Fine Powder (% by number) | Charging Property Normal Temperature and Humidity (Q/M) | | High Temperature and Humidity (Q/M) | |
|---|---|---|---|---|---|---|---|---|
| | | | | | 10-Second Agitation | 300-Second Agitation | 10-Second Agitation | 300-Second Agitation |
| Example | | | | | | | | |
| 20 | 1 | 1 | 7.4 | 5.0 | A | AA | A | AA |
| 21 | 2 | 2 | 7.1 | 5.0 | A | AA | A | AA |
| 22 | 3 | 3 | 7.0 | 5.1 | A | AA | A | AA |
| 23 | 4 | 4 | 7.4 | 5.3 | A | A | A | A |
| 24 | 5 | 5 | 6.9 | 5.5 | A | A | B | B |
| 25 | 6 | 6 | 7.0 | 5.5 | B | A | B | B |
| Comparative Example 1 | — | 7 | 7.0 | 5.2 | C | C | C | C |

Examples 26 to 31

Yellow toners (1) to (6) of the Examples 26 to 31 were obtained using 2.0 parts by mass of the exemplified compounds (1) to (6), respectively, in the same manner as the Example 20 except that a yellow colorant (Hansa yellow G) was used instead of a cyan colorant. The properties of the toners were determined in the same manner as in the Example 20 and the results are shown in Table 16. And two-component yellow developers (1) to (6) were obtained in the same manner as in the Example 20.

Comparative Example 2

Yellow toner (7) of the Comparative Example 2 was obtained in the same manner as in the Example 20 except that no exemplified compounds were used and a yellow colorant (Hansa yellow G) was used instead of a cyan colorant. The properties of the toner were determined in the same manner as in the Example 20 and the results are shown in Table 16. And a two-component yellow developer (7) of the Comparative Example 2 was obtained with this toner in the same manner as in the Example 20.

<Evaluation>

The amount of electrical charge of the toners was measured of two-component yellow developers (1) to (6) obtained in the Examples 26 to 31 and two-component yellow developer (7) obtained in the Comparative Example 2, respectively, after 10-second and 300-second agitation under the environmental conditions of normal temperature and humidity (25° C., 60% RH) and of high temperature and humidity (30° C., 80% RH) adopting the method of measuring the amount of electrical charge described above. Evaluation was made with the values obtained by rounding off the measured values of the amount of the two-component blow-off electrical charge to nearest tenth on the basis of the criteria below. The results are shown in Table 16 together.

(Charging Property)

AA: very good (−20 $\mu$C/g or less)

A: good (−19.9 to −10.0 $\mu$C/g)

B: practically permissible (−9.9 to −5.0 $\mu$C/g)

C: practically impermissible (−4.9 $\mu$C/g or more)

as in the Example 20 and the results are shown in Table 20. And two-component black developers (1) to (6) were obtained in the same manner as in the Example 20.

Comparative Example 3

Black toner (7) of the Comparative Example 3 was obtained in the same manner as in the Example 20 except that no exemplified compounds were used and carbon black (DBP oil absorption 110 mL/100 g) was used instead of a cyan colorant. The properties of the toner were determined in the same manner as in the Example 20 and the results are shown in Table 17. And a two-component black developer (7) of the Comparative Example 3 was obtained with this toner in the same manner as in the Example 20.

<Evaluation>

The amount of electrical charge of the toners was measured of two-component black developers (1) to (6) obtained in the Examples 32 to 37 and two-component black developer (7) obtained in the Comparative Example 3, respectively, after 10-second and 300-second agitation under the environmental conditions of normal temperature and humidity (25° C., 60% RH) and of high temperature and humidity (30° C., 80% RH) adopting the method of measuring the amount of electrical charge described above. Evaluation was made with the values obtained by rounding off the measured values of the amount of the two-component blow-off electrical charge to nearest tenth on the basis of the criteria below. The results are shown in Table 17 together.

TABLE 16

Particle Size Distribution and Charging Property of Yellow Toners (1) to (6)

| | | | | Charging Property | | | |
|---|---|---|---|---|---|---|---|
| | | | | Normal Temperature and Humidity (Q/M) | | High Temperature and Humidity (Q/M) | |
| Exemplified Compound No. | Toner No.: Yellow | Weight-Average Particle Size ($\mu$m) | Amount of Fine Powder (% by number) | 10-Second Agitation | 300-Second Agitation | 10-Second Agitation | 300-Second Agitation |
| Example | | | | | | | |
| 26 | 1 | 1 | 6.9 | 5.2 | AA | AA | A | AA |
| 27 | 2 | 2 | 7.0 | 5.3 | A | AA | A | A |
| 28 | 3 | 3 | 7.1 | 5.3 | A | AA | A | A |
| 29 | 4 | 4 | 7.1 | 5.8 | A | AA | A | A |
| 30 | 5 | 5 | 7.0 | 5.9 | A | A | B | A |
| 31 | 6 | 6 | 6.9 | 5.1 | B | A | B | A |
| Comparative Example 2 | — | 7 | 7.2 | 4.9 | C | C | C | C |

Examples 32 to 37

Black toners (1) to (6) of the Examples 32 to 37 were obtained using 2.0 parts by mass of the exemplified compounds (1) to (6), respectively, in the same manner as the Example 20 except that carbon black (DBP oil absorption 110 mL/100 g) was used instead of a cyan colorant. The properties of the toners were determined in the same manner (Charging Property)

AA: very good (−20 $\mu$C/g or less)

A: good (−19.9 to −10.0 $\mu$C/g)

B: practically permissible (−9.9 to −5.0 $\mu$C/g)

C: practically impermissible (−4.9 $\mu$C/g or more)

TABLE 17

Particle Size Distribution and Charging Property of Black Toners (1) to (6)

| | | | | | Charging Property | | | |
|---|---|---|---|---|---|---|---|---|
| | | | Particle Size Distribution | | Normal Temperature and Humidity (Q/M) | | High Temperature and Humidity (Q/M) | |
| | | | Weight- Average Particle Size ($\mu$m) | Amount of Fine Powder (% by number) | 10- Second Agitation | 300- Second Agitation | 10- Second Agitation | 300- Second Agitation |
| | Exemplified Compound No. | Toner No.: Black | | | | | | |
| Example | | | | | | | | |
| 32 | 1 | 1 | 7.4 | 5.3 | A | AA | A | A |
| 33 | 2 | 2 | 6.9 | 5.5 | A | AA | A | A |
| 34 | 3 | 3 | 7.0 | 6.0 | A | AA | A | A |
| 35 | 4 | 4 | 7.0 | 6.1 | A | A | A | A |
| 36 | 5 | 5 | 7.4 | 5.4 | B | A | B | B |
| 37 | 6 | 6 | 7.2 | 5.5 | B | A | B | B |
| Comparative Example 3 | — | 7 | 6.9 | 5.3 | C | B | C | B |

Example 38

| | |
|---|---|
| Styrene-butyl acrylate copolymer resin (glass transition temperature 70° C.) | 100 parts by mass |
| Magenta pigment (C.I. pigment Red 114) | 5 parts by mass |
| Exemplified compound (1) | 2 parts by mass |

The above composition was mixed and melt-kneaded with a biaxial extruder (L/D=30). The kneaded mixture was cooled, hammer milled, jet milled, classified, followed by grinding to obtain magenta coloring particles (1). For the particle size of the magenta coloring particles (1), the weight-average particle diameter was 7.2 $\mu$m and the amount of the fine powder was 5.3% by number.

Then 1.5 parts by mass of finely powdered hydrophobic silica (BET: 250 m$^2$/g) having been treated with hexamethyldisilazane, as a flow improver, was dry mixed with 100 parts by mass of the magenta coloring particles (1) with a Henschel mixer, to obtain magenta toner (1) of this example. And 7 parts by mass of the obtained magenta toner (1) and 93 parts by mass of resin-coated magnetic ferrite carrier (average particle size: 45 $\mu$m) were mixed with each other to prepare a two-component magenta developer (1) for magnetic brush development.

Examples 39 to 43

Magenta toner (2) to (6) of the Examples 39 to 43 was obtained in the same manner as in the Example 38 except that 2.0 parts by mass of the exemplified compounds (2) to (6) were used instead of the exemplified compound (1). The properties of the toner were determined in the same manner as in the Example 20 and the results are shown in Table 18. And a two-component magenta developers (2) to (6) were obtained with this toner in the same manner as in the Example 38.

Comparative Example 4

Magenta toner (7) of the Comparative Example 4 was obtained in the same manner as in the Example 38 except that none of the exemplified compounds were used. The properties of the toner were determined in the same manner as in the Example 20 and the results are shown in Table 18. And a two-component magenta developer (9) of the Comparative Example 4 was obtained with this toner in the same manner as in the Example 38.

<Evaluation>

The amount of electrical charge of the toners was measured of the two-component magenta developers (1) to (6) obtained in the Examples 38 to 43 and the two-component magenta developer (7) obtained in the Comparative Example 4, respectively, after 10-second and 300-second agitation under the environmental conditions of normal temperature and humidity (25° C., 60% RH) and of high temperature and humidity (30° C., 80% RH) adopting the method of measuring the amount of electrical charge described above. Evaluation was made with the values obtained by rounding off the measured values of the amount of the two-component blow-off electrical charge to nearest tenth on the basis of the criteria below. The results are shown in Table 18 together.

(Charging Property)

AA: very good (−20 $\mu$C/g or less)
A: good (−19.9 to −10.0 $\mu$C/g)
B: practically permissible (−9.9 to −5.0 $\mu$C/g)
C: practically impermissible (−4.9 $\mu$C/g or more)

TABLE 18

Particle Size Distribution and Charging Property of Magenta Toners (1) to (6)

| | | | | | Charging Property | | | |
|---|---|---|---|---|---|---|---|---|
| | | | Particle Size Distribution | | Normal Temperature and Humidity (Q/M) | | High Temperature and Humidity (Q/M) | |
| | Exemplified Compound No. | Toner No.: Red | Weight-Average Particle Size (μm) | Amount of Fine Powder (% by number) | 10-Second Agitation | 300-Second Agitation | 10-Second Agitation | 300-Second Agitation |
| Example | | | | | | | | |
| 38 | 1 | 1 | 7.2 | 5.3 | AA | AA | A | A |
| 39 | 2 | 2 | 6.9 | 5.2 | AA | AA | A | A |
| 40 | 3 | 3 | 7.2 | 5.0 | AA | AA | A | A |
| 41 | 4 | 4 | 7.1 | 5.5 | AA | A | A | A |
| 42 | 5 | 5 | 7.0 | 5.7 | B | A | B | A |
| 43 | 6 | 6 | 7.1 | 5.3 | B | A | B | A |
| Comparative Example 4 | — | 7 | 7.1 | 5.1 | C | B | C | B |

Examples 44 to 49

Black toners (8) to (13) of the Examples 44 to 49 were obtained using 2.0 parts by mass of the exemplified compounds (1) to (6), respectively, in the same manner as the Example 38 except that carbon black (DBP oil absorption 110 mL/100 g) was used instead of a magenta pigment. The properties of the toners were determined in the same manner as in the Example 20 and the results are shown in Table 19. And two-component black developers (8) to (13) were obtained in the same manner as in the Example 20.

Comparative Example 5

Black toner (14) of the Comparative Example 5 was obtained in the same manner as in the Example 38 except that no exemplified compounds were used and carbon black (DBP oil absorption 110 mL/100 g) was used instead of a magenta pigment. The properties of the toner were determined in the same manner as in the Example 20 and the results are shown in Table 19. And a two-component black developer (14) of the Comparative Example 5 was obtained with this toner in the same manner as in the Example 20.

<Evaluation>

The amount of electrical charge of the toners was measured of two-component black developers (8) to (13) obtained in the Examples 44 to 49 and two-component black developer (14) obtained in the Comparative Example 5, respectively, after 10-second and 300-second agitation under the environmental conditions of normal temperature and humidity (25° C., 60% RH) and of high temperature and humidity (30° C., 80% RH) adopting the method of measuring the amount of electrical charge described above. Evaluation was made with the values obtained by rounding off the measured values of the amount of the two-component blow-off electrical charge to nearest tenth on the basis of the criteria below. The results are shown in Table 19 together.

(Charging Property)

AA: very good (−20 μC/g or less)
A: good (−19.9 to −10.0 μC/g)
B: practically permissible (−9.9 to −5.0 μC/g)
C: practically impermissible (−4.9 μC/g or more)

TABLE 19

Particle Size Distribution and Charging Property of Black Toners (9) to (14)

| | | | | | Charging Property | | | |
|---|---|---|---|---|---|---|---|---|
| | | | Particle Size Distribution | | Normal Temperature and Humidity (Q/M) | | High Temperature and Humidity (Q/M) | |
| | Exemplified Compound No. | Toner No.: Black | Weight-Average Particle Size (μm) | Amount of Fine Powder (% by number) | 10-Second Agitation | 300-Second Agitation | 10-Second Agitation | 300-Second Agitation |
| Example | | | | | | | | |
| 44 | 1 | 8 | 7.1 | 5.0 | AA | AA | A | A |
| 45 | 2 | 9 | 7.2 | 5.1 | A | AA | A | A |

TABLE 19-continued

Particle Size Distribution and Charging Property of Black Toners (9) to (14)

| | | | Particle Size Distribution | | Charging Property | | | |
|---|---|---|---|---|---|---|---|---|
| | | | | | Normal Temperature and Humidity (Q/M) | | High Temperature and Humidity (Q/M) | |
| | Exemplified Compound No. | Toner No.: Black | Weight- Average Particle Size (μm) | Amount of Fine Powder (% by number) | 10- Second Agita- tion | 300- Second Agita- tion | 10- Second Agita- tion | 300- Second Agita- tion |
| 46 | 3 | 10 | 7.1 | 5.2 | A | AA | A | A |
| 47 | 4 | 11 | 6.9 | 4.9 | A | A | A | A |
| 48 | 5 | 12 | 7.1 | 5.0 | B | A | B | A |
| 49 | 6 | 13 | 7.0 | 4.9 | B | A | B | A |
| Compa- rative Example 5 | — | 14 | 7.0 | 5.7 | C | B | C | C |

Example 50

| | |
|---|---|
| Polyester resin | 100 parts by mass |
| Carbon black (DBP oil absorption 110 mL/100 g) | 5 parts by mass |
| Exemplified compound (1) | 2 parts by mass |

Polyester resin was synthesized as follows. 751 parts of adduct with 2 mol of bisphenol A propylene oxide, 104 parts of terephthalic acid and 167 parts of trimellitic anhydride were polycondensed in the presence of 2 parts of dibutyltin oxide as a catalyst to obtain polyester resin with a softening point of 125° C.

The above composition was mixed and melt-kneaded with a biaxial extruder (L/D=30). After cooled, the kneaded mixture was hammer milled, jet milled, classified, followed by grinding to obtain black coloring particles (15). For the particle size of the black coloring particles (15), the weight-average particle diameter was 7.7 μm and the amount of the fine powder was 5.0% by number.

Then 1.5 parts by mass of finely powdered hydrophobic silica (BET: 250 m²/g) having been treated with hexamethyldisilazane, as a flow improver, was dry mixed with 100 parts by mass of the black coloring particles (15) with a Henschel mixer. And 7 parts by mass of (the obtained black toner (15)) and 93 parts by mass of resin-coated magnetic ferrite carrier (average particle size: 45 μm) were mixed with each other to prepare a two-component black developer (15) for magnetic brush development.

Example 51 to 55

Black toners (16) to (20) of the Examples 51 to 55 were obtained in the same manner as in the Example 50 except that 2.0 parts by mass of the exemplified compounds (2) to (6) were used instead of the exemplified compound (1). The properties of the toner were determined in the same manner as in the Example 20 and the results are shown in Table 20. And a two-component black developers (16) to (20) were obtained with this toner in the same manner as in the Example 50.

Comparative Example 6

Black toner (27) of the Comparative Example 6 was obtained in the same manner as in the Example 50 except that none of the exemplified compounds were used. The properties of the toner were determined in the same manner as in the Example 20 and the results are shown in Table 20. And a two-component black developer (21) of the Comparative Example 6 was obtained with this toner in the same manner as in the Example 50.

<Evaluation>

The amount of electrical charge of the toners was measured of the two-component black developers (15) to (20) obtained in the Examples 50 to 55 and the two-component black developer (21) obtained in the Comparative Example 6, respectively, after 10-second and 300-second agitation under the environmental conditions of normal temperature and humidity (25° C., 60% RH) and of high temperature and humidity (30° C., 80% RH) adopting the method of measuring the amount of electrical charge described above. Evaluation was made with the values obtained by rounding off the measured values of the amount of the two-component blow-off electrical charge to nearest tenth on the basis of the criteria below. The results are shown in Table 20 together.

(Charging Property)

AA: very good (−20 μC/g or less)
A: good (−19.9 to −10.0 μC/g)
B: practically permissible (−9.9 to −5.0 μC/g)
C: practically impermissible (−4.9 μC/g or more)

TABLE 20

Particle Size Distribution and Charging Property of Black Toners (15) to (20)

| | | | | Charging Property | | | |
|---|---|---|---|---|---|---|---|
| | | Particle Size Distribution | | Normal Temperature and Humidity (Q/M) | | High Temperature and Humidity (Q/M) | |
| | | | Amount | | | | |
| Exemplified Compound No. | Toner No.: Black | Weight- Average Particle Size ($\mu$m) | of Fine Powder (% by number) | 10- Second Agita- tion | 300- Second Agita- tion | 10- Second Agita- tion | 300- Second Agita- tion |
| Example | | | | | | | |
| 50 | 1 | 15 | 7.7 | 5.0 | A | AA | A | AA |
| 51 | 2 | 16 | 8.0 | 5.2 | A | AA | A | AA |
| 52 | 3 | 17 | 7.6 | 5.3 | A | AA | A | AA |
| 53 | 4 | 18 | 7.9 | 5.3 | A | AA | A | A |
| 54 | 5 | 19 | 8.1 | 5.0 | B | A | B | A |
| 55 | 6 | 20 | 7.7 | 5.1 | B | A | B | A |
| Compa- rative Example 6 | — | 21 | 7.5 | 4.9 | C | B | C | B |

Examples 56 to 71 and Comparative Examples 7 to 12

Figure 4:
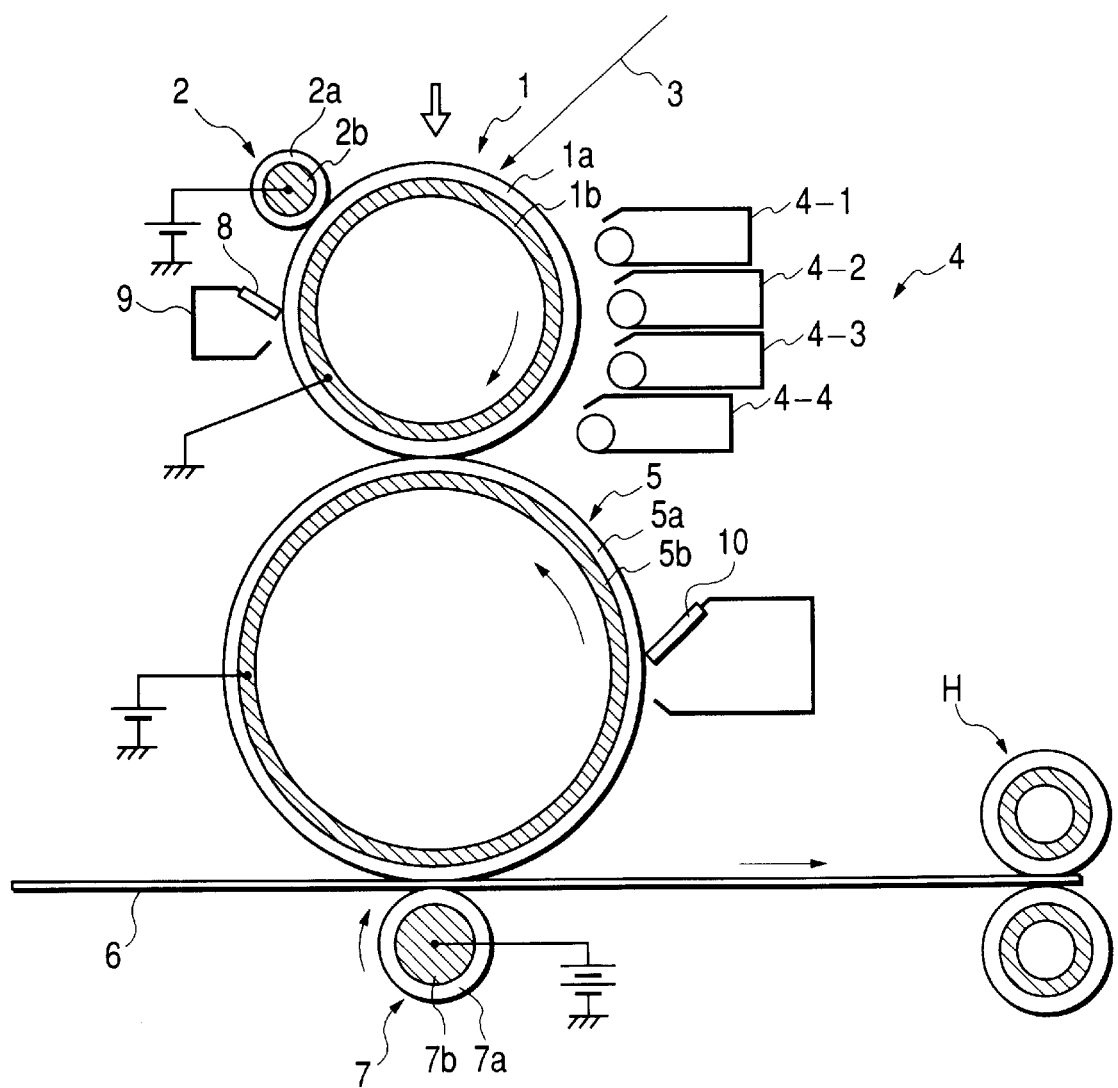
FIG. 4 is a schematic illustration of an image-forming apparatus used in Examples 56 to 71 and Comparative Examples 7 to 12.

First, an image forming apparatus having been used in the method of image formation in the Examples 56 to 71 and in the Comparative Examples 7 to 12 will be described. FIG. 4 is a schematic view illustrating a cross section of an image forming apparatus for carrying out the image forming method of the Examples and Comparative Examples of this invention. The photosensitive drum 1 shown in FIG. 4 has a photosensitive layer 1a, which includes organic optical semiconductor, on a base material 1b and is structured in such a manner as to rotate in the direction shown by the arrow. The surface of the photosensitive drum 1 is charged at about −600V surface electric potential by a charging roller 2 as a charging member which rotates in contact with the above drum 1. As shown in FIG. 4, the charging roller 2 consists of a conductive elastic layer 2a and a core bar 2b which is coated with the above conductive elastic layer.

Figure 5:
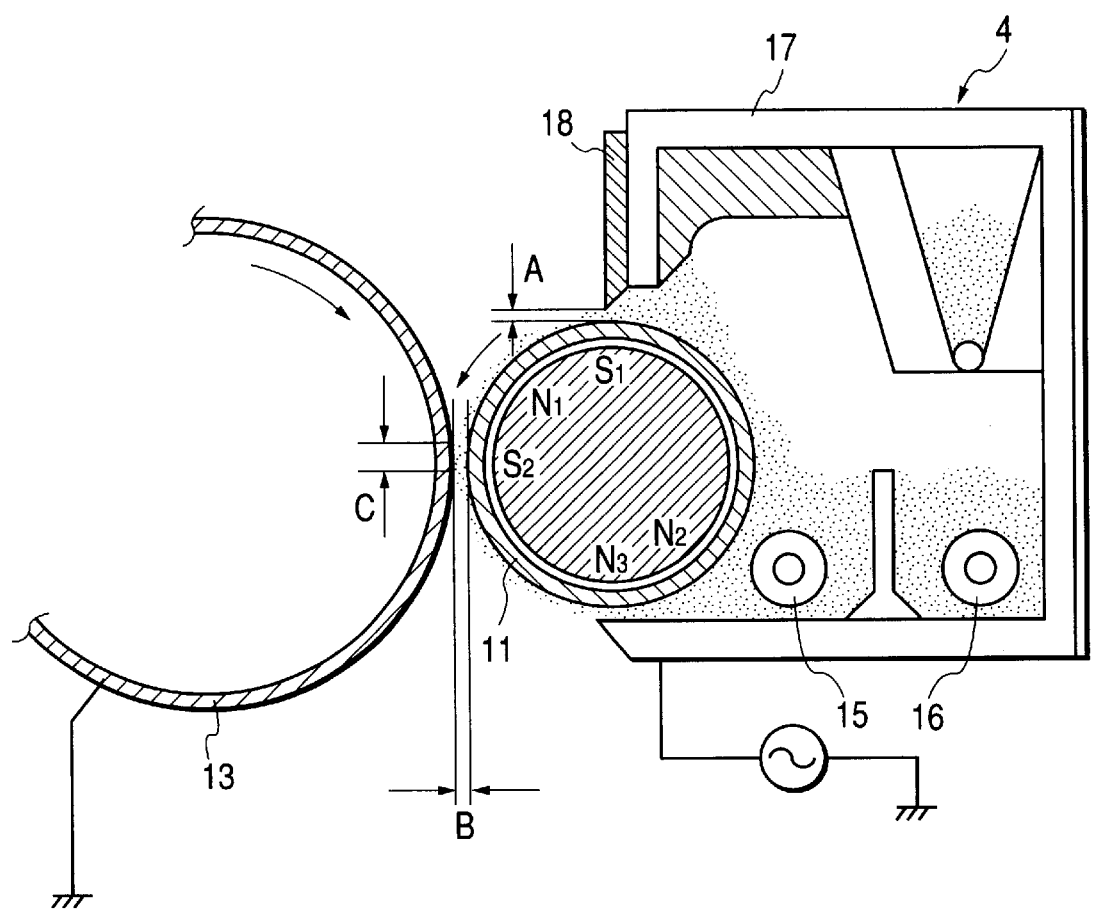
FIG. 5 is a sectional view of the main part of a developing assembly for two-component developer, used in Examples 56 to 71 and Comparative Examples 7 to 12.

The photosensitive drum 1 with its surface electrically charged is exposed to light 3, and at the time of the exposure an image of electrostatic charges with −100V electrical potential at the exposed portion and −600V electrical potential at the dark portion is on the drums formed by turning on and off the light with a polygon mirror according to the digital image information. Then the image of electrostatic charges on the photosensitive drum 1 is reversely developed with a plurality of developing equipment 4-1, 4-2, 4-3 and 4-4 to become tangible; thus, a toner image is formed on the photosensitive drum 1. In this developing, two-component developers obtained in the Examples 20 to 26, 29, 32, 35, 38, 41, 44, 47, 50 and 53 and in the Comparative Examples 1 to 6 were used and the toner image was formed with yellow, magenta, cyan or black toner. FIG. 5 is an enlarged sectional view illustrating the main part of each developing equipment 4 used with the two-component developers.

Then the toner image on the photosensitive drum 1 is transferred to an intermediate transfer body 5, which rotates in contact with the photosensitive drum 1. As a result, a developed image made up of four colors of toner overlaid is formed on the intermediate transfer body 5. The residual toner, which has not been transferred to the intermediate transfer body 5 and left on the photosensitive drum 1, is collected into a container 9 for residual toner with a cleaning member 8.

The intermediate transfer body 5 consists of a core bar 5b, as a base material, and an elastic layer 5a laminated on the core bar, as shown in FIG. 4. In this example, an intermediate transfer body 5 was used which consisted of an elastic layer 5a of nitrile-butadiene rubber in which carbon black, as a conductivity-imparting material, was fully dispersed and a pipe-like core bar 5b coated with the elastic layer 5a. The hardness of the elastic layer 5a measured in accordance with "JIS K-6301" was 30 degree and the volume resistivity of the same was $10^9$ $\Omega\cdot$cm. Transfer current needed for transferring the toner image from the photosensitive drum 1 to the intermediate transfer body 5 was about 5 $\mu$A and the current was obtained by applying +500V from a voltage source to the core bar 5b.

The developed image made up of four colors of toner overlaid having been formed on the intermediate transfer body 5 is transferred to a transfer medium such as paper by a transfer roller 7 and fixed thereon with a heat fixing equipment H. The transfer roller 7 consists of an elastic layer 7a of a cellular material of ethylene-propylene-diene terpolymer (EPDM) in which carbon black, as a conductivity-imparting material, has fully dispersed and a core bar 7b of 10 mm in outer diameter coated with the elastic layer 7a. The volume resistivity of the used elastic layer 7a was $10^6$ $\Omega\cdot$cm and the hardness of it measured in accordance with "JIS K-6301" was 35. A transfer current of 15 $\mu$A was allowed to flow through the transfer roller 7 by applying a voltage thereto.

Figure 8:
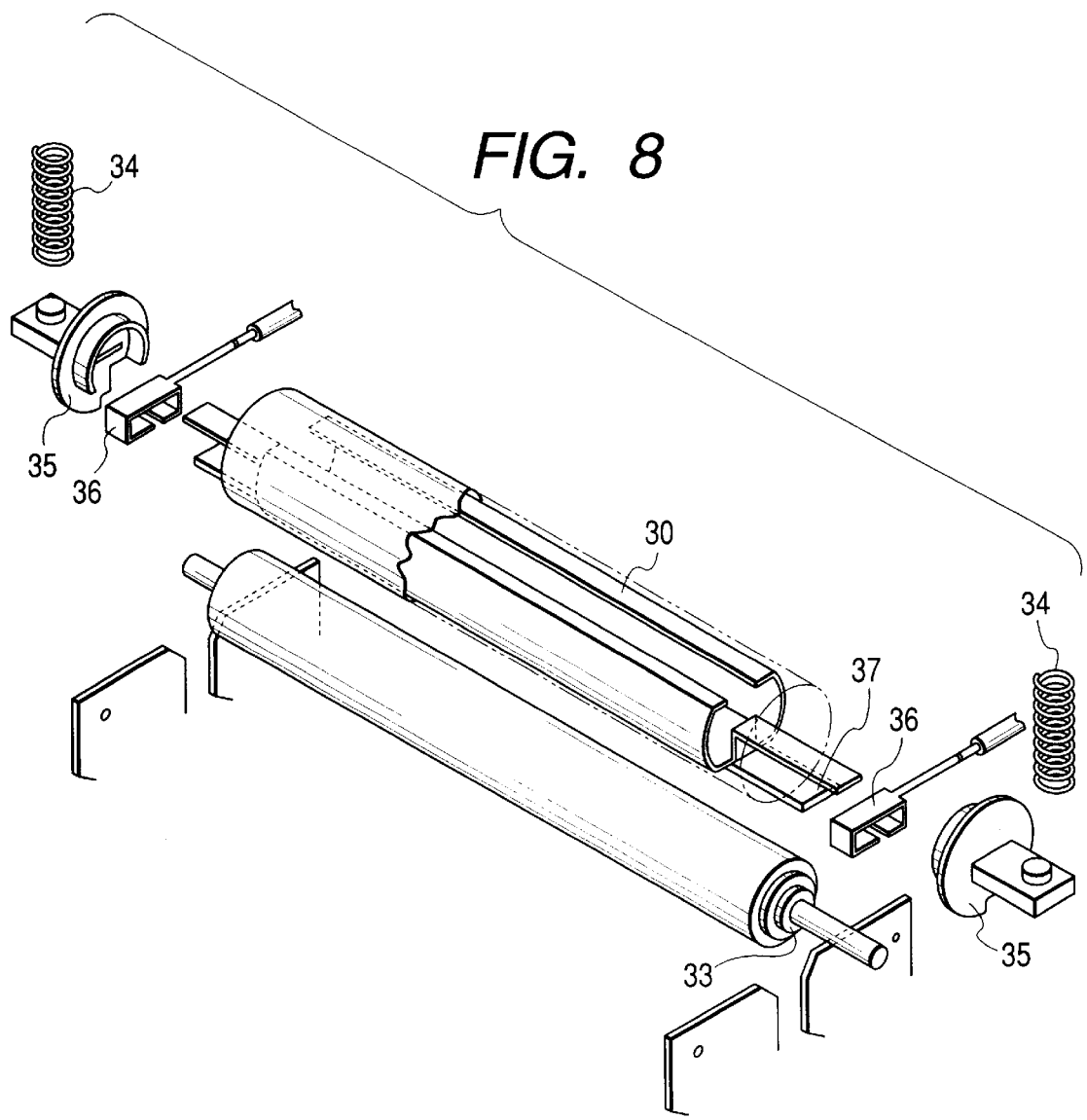
FIG. 8 is an exploded, perspective view of the main part of a fixing assembly used in Examples of the present invention.
Figure 9:
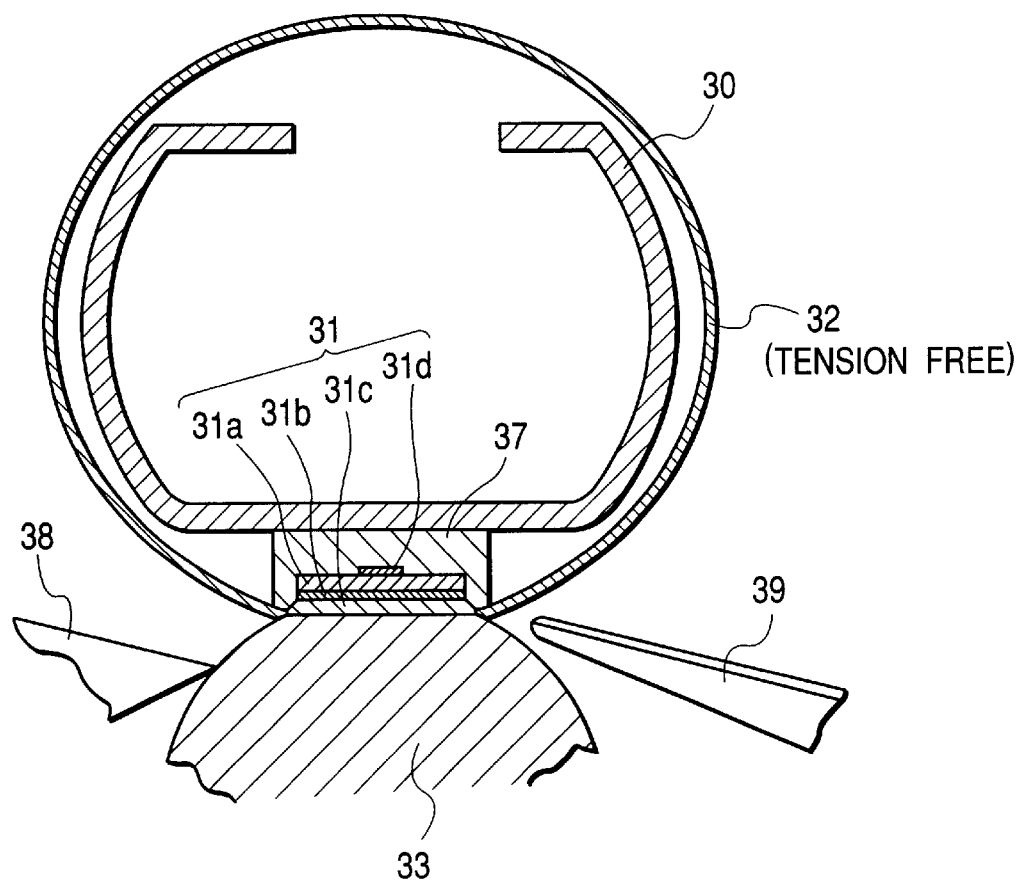
FIG. 9 is an enlarged sectional view of the main part of a fixing assembly used in Examples of the present invention, which shows how a fixing film stands when the fixing assembly is not driven.

In the apparatus shown in FIG. 4, a heat roll type of fixing equipment without an oil coating mechanism, as shown in FIGS. 8 and 9, was used as a heat fixing equipment H. And the apparatus used was such that both its upper roller and lower roller were provided with a surface layer of fluorocarbon resin. The diameter of each roller was 60 nm. The temperature at the time of fixing was 160° C. and the nip between the rolls was set at 7 mm. The residual toner, which had not been transferred to the intermediate transfer body 5 and left on the photosensitive drum 1, collected by cleaning was conveyed to the developing equipment by a reuse mechanism to be reused.

<Evaluation>

Printout tests were conducted on the above image forming apparatus at a print speed of 8 sheets of paper (A4 size) per minute in monochrome in an intermittent mode (that is, a mode in which developing equipment is stopped over 10 seconds every time printing is done on a sheet of paper, so as to accelerate the degradation of toner by the spare operation at the time of restart) under the environmental conditions of normal temperature and humidity (25° C., 60% RH) and of high temperature and humidity (30° C., 80% RH), while supplying sequentially two-component developers prepared using the toner of the Examples 20 to 26, 29, 32, 35, 38, 41, 44, 47, 50 and 53 and of the Comparative Examples 1 to 6, and the obtained printout images were evaluated on the following items. The evaluation results are shown in Table 21 together.

(Evaluation of Printout Image)

1. Image Density

Printing was done on a prescribed number of sheets of paper, ordinary plain paper for copying (75 g/m$^2$), and evaluation was made in terms of the degree to which the density of the printout image at the very beginning of printing was maintained by the printout image at the very end of printing. The image density was measured with a Macbeth reflection densitometer (manufactured by Macbeth) and the relative density of printout image on a white background with a copy density of 0.00 was measured and used for the evaluation.

AA: Excellent (image density at the very end of printing was 1.40 or more)

A: Good (image density at the very end of printing was 1.35 or more and less than 1.40)

B: Fair (image density at the very end of printing was 1.00 or more and less than 1.35)

C: Bad (image density at the very end of printing was less than 1.00)

2. Image Fog

Printing was done on a prescribed number of sheets of paper, ordinary plain paper for copying (75 g/m$^2$), and evaluation was made in terms of the white solid image at the very end of printing. Specifically, the evaluation was made in the following manner. First the fog density was obtained from the following formula: (Ds-Dr), where Ds is the worst value of the reflection density on the white background portion after printing measured with a reflection densitometer (REFLECTOMETER ODEL TC-6DS by TOKYO DENSHOKU CO., LTD) and Dr is the mean value of the reflection density of the paper before printing. Then evaluation was made based on the following criteria.

AA: Very good (fog density was 0% or more and less than 1.5%)

A: Good (fog density was 1.5% or more and less than 3.0%)

B: Practically permissible (fog density was 3.0% or more and less than 5.0%)

C: Practically impermissible (fog density was 5.0% or more)

3. Transfer Properties

A black solid image was printed out on a prescribed number of sheets of paper, ordinary plain paper for copying (75 g/m$^2$), and the image missing at the very end of printing was visually observed. Evaluation was made based on the following criteria.

AA: Very good (almost no image missing occurred)

A: Good (slight image missing was observed)

B: Practically permissible

C: Practically impermissible

In Examples 56 to 71 and in Comparative Examples 7 to 12, an image was printed out on 5,000 sheets of paper, and visual evaluation was made on scratches and retention of the toner occurring on the photosensitive drum and on the surface of the intermediate transfer body as well as the effect on the printout image (match between the toners and the image forming apparatus). The results were as follows. In the system of the Examples 56 to 71 using the two-component developers, neither scratches nor retention of the residual toner was observed on the surface of the photosensitive drum and of the intermediate transfer body and the match between the toners and the image forming apparatus was very good. On the other hand, in the system of the Comparative Examples 7 to 12 using the two-component developers, retention of the toner was observed on the surface of the photosensitive drum. Furthermore, in the system of the Comparative Examples 7 to 12 using the two-component developers, retention of the toner and scratches were observed on the surface of the intermediate transfer body and defects in the form of vertical lines was also observed in the image. Thus problems arouse in the match between the toners and the image forming apparatus.

TABLE 21

| | | Evaluation of Printout Image | | | | | |
|---|---|---|---|---|---|---|---|
| | Two- | Normal Temperature and Humidity | | | High Temperature and Humidity | | |
| | component Developer | Image Density | Image Fog | Transfer Properties | Image Density | Image Fog | Transfer Properties |
| Example | | | | | | | |
| 56 | blue 1 | AA | AA | AA | A | A | A |
| 57 | blue 2 | AA | AA | AA | A | A | A |
| 58 | blue 3 | AA | AA | AA | A | A | B |
| 59 | blue 4 | AA | A | A | A | B | B |
| 60 | blue 5 | A | A | A | A | B | B |
| 61 | blue 6 | A | A | B | A | B | B |
| 62 | yellow 1 | AA | AA | AA | A | A | A |
| 63 | yellow 4 | AA | AA | A | A | A | B |
| 64 | black 1 | AA | AA | AA | A | A | A |
| 65 | black 4 | AA | A | A | A | B | B |

TABLE 21-continued

Evaluation of Printout Image

|  | Two-component Developer | Normal Temperature and Humidity | | | High Temperature and Humidity | | |
|---|---|---|---|---|---|---|---|
|  |  | Image Density | Image Fog | Transfer Properties | Image Density | Image Fog | Transfer Properties |
| 66 | red 1 | AA | AA | AA | A | AA | A |
| 67 | red 4 | AA | A | A | A | B | B |
| 68 | black 8 | AA | AA | AA | A | AA | A |
| 69 | black 11 | AA | A | A | A | A | B |
| 70 | black 15 | AA | AA | AA | A | AA | A |
| 71 | black 18 | AA | A | A | A | A | B |
| Co. Ex |  |  |  |  |  |  |  |
| 7 | blue 7 | C | C | C | C | C | C |
| 8 | yellow 7 | C | C | C | C | C | C |
| 9 | black 7 | B | B | C | B | C | C |
| 10 | red 7 | B | B | C | B | C | C |
| 11 | black 14 | B | B | C | C | C | C |
| 12 | black 21 | B | B | C | B | C | C |

Note: Co. Ex 7 in Table 21 is the abbreviation for Comparative Example 7.

Examples 72 to 74, Comparative Examples 13 to 15

Figure 6:
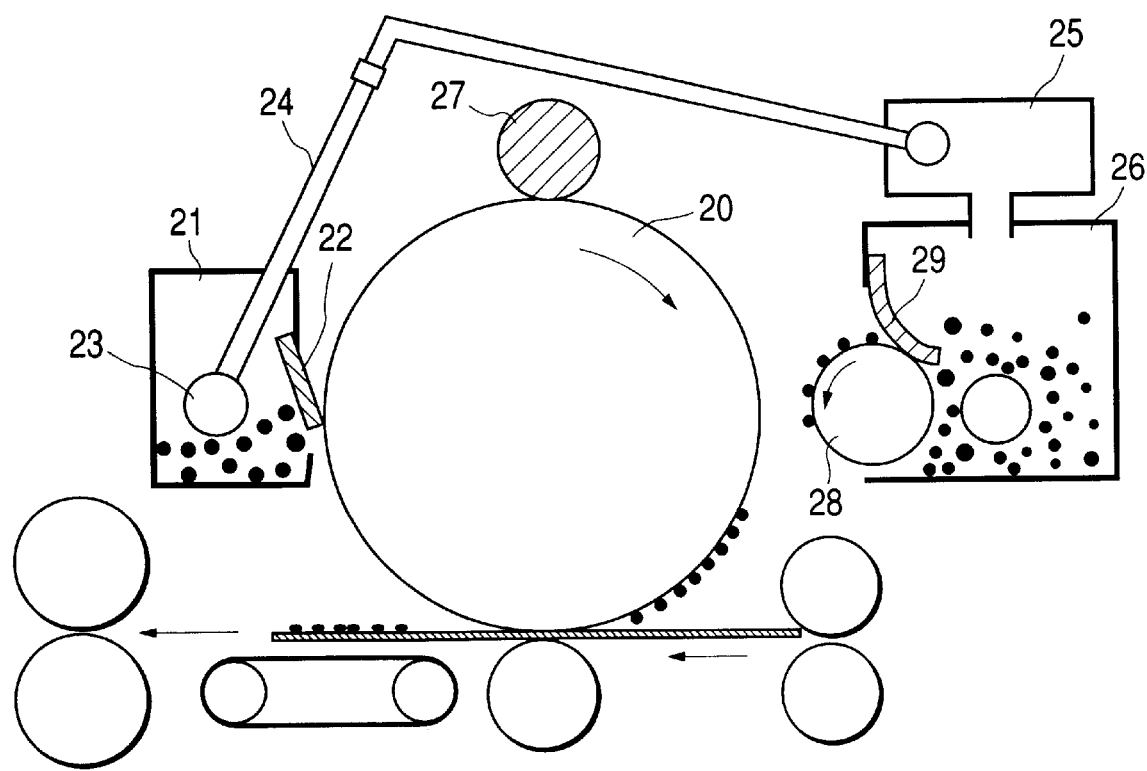
FIG. 6 is a schematic illustration of an image-forming apparatus having a toner reuse mechanism, used in Examples 72 to 74 and Comparative Examples 13 to 15.

When carrying out the image forming methods of the Examples 72 to 74 and the Comparative Examples 13 to 15, the toners obtained in the Examples 20, 26 and 32 and in the Comparative Examples 1 to 3 were used as developers, respectively. And as means of forming an image, used was an image forming apparatus obtained by remolding a commercially available laser beam printer, LBP-EX (manufactured by Canon), in such a manner as to be mounted with a reuse mechanism and by resetting the same, as shown in FIG. 6. Specifically, the image forming apparatus shown in FIG. 6 was mounted with a system for reusing toner in which the toner having not been transferred and remaining on the photosensitive drum 20 was scraped off with the elastic blade 22 of the cleaner 21 in contact with the photosensitive drum 20, conveyed to the inside of the cleaner 21 with a cleaner roller, passed through the cleaner reuse 23, and returned to the developing equipment 26 via the hopper 25 with a supplying pipe 24 provided with a conveying screw.

In the image forming apparatus shown in FIG. 6, the surface of the photosensitive drum 20 was charged with a primary charging roller 27. As the primary charging roller 27 a nylon-resin coated rubber roller (12 mm in diameter, contact pressure 50 g/cm) in which conductive carbon was dispersed was used, and the electrostatic latent image carrier (photosensitive drum 20) was exposed to laser beam (600 dpi, not shown in the Figure) to form an electrostatic latent image with a dark portion potential VD of −700V and a light portion potential VL of −200V. As a toner carrier, a developing sleeve 28 coated with resin, in which carbon black was dispersed, and having a surface roughness Ra of 1.1 was used.

Figure 7:
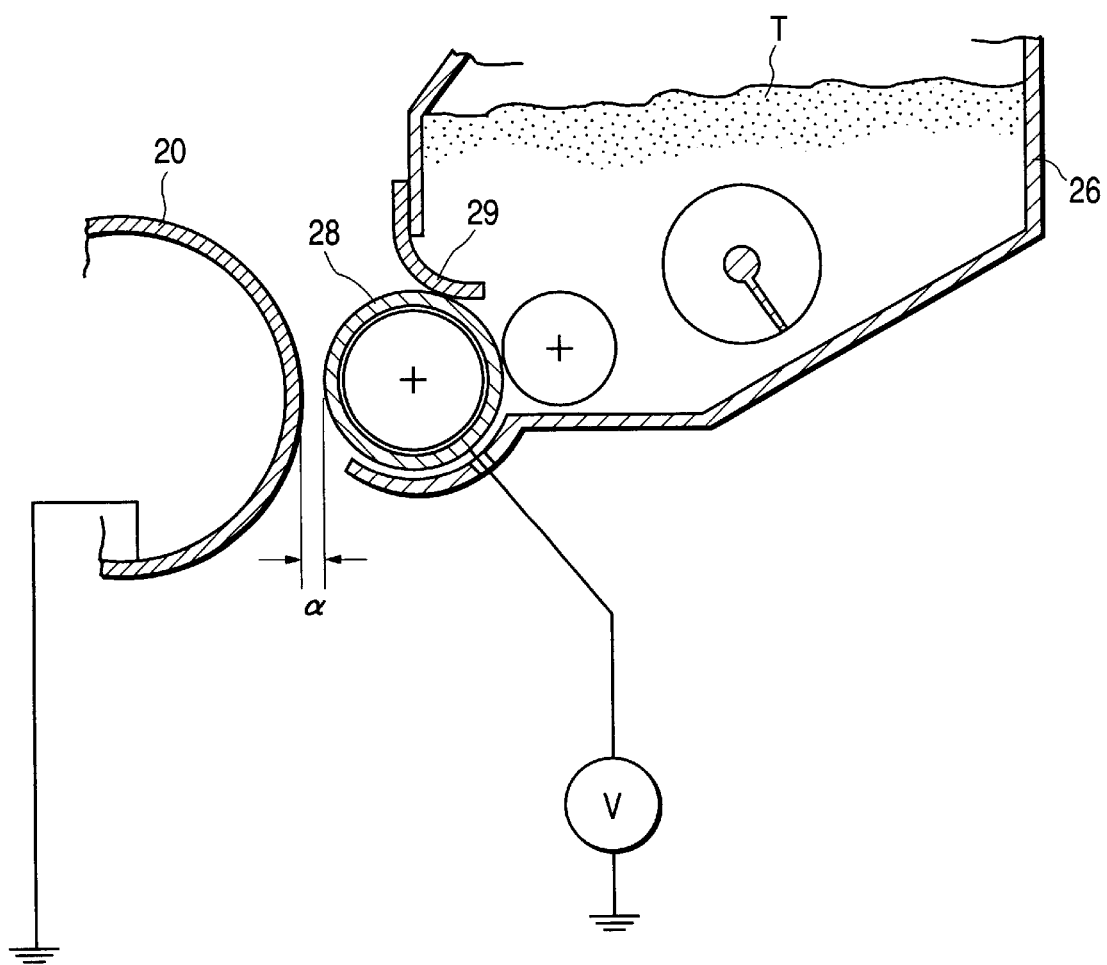
FIG. 7 is a sectional view of the main part of a developing assembly for one-component developer, used in Examples 72 to 74 and Comparative Examples 13 to 15.

FIG. 7 is an enlarged sectional view of the main part of the developing equipment for single-component developer used in the Examples 72 to 74 and in the Comparative Examples 13 to 15. The conditions under which an electrostatic latent image was developed were such that the moving speed of the developing sleeve 28 was set at 1.1 times as fast as that of the surface of the photosensitive drum 20 facing the developing sleeve and the space α between the photosensitive drum 20 and the developing sleeve 28 (space S-D) was set at 270 μm. As a member for regulating the thickness of the toner layer, a urethane rubber blade 29 was used in such a manner as to be in contact with the developing sleeve 28. The temperature of a heat fixing equipment for fixing the toner image was set at 160° C. As a heat fixing equipment, the fixing equipment shown in FIGS. 8 and 9 was used.

Printing was done on 30,000 sheets of paper on the above image forming apparatus at a print speed of 8 sheets of paper (A4 size) per minute in a continuous mode (that is, a mode in which the consumption of toner was accelerated without stopping developing equipment) under the environmental conditions of normal temperature and humidity (25° C., 60% RH), while sequentially supplying toner. The density of the obtained printout image was measured and the durability was evaluated based on the criteria described below. Further, the image of the 10,000th printout was observed and the image fog was evaluated based on the criteria described below. The state of equipment constituting the image forming apparatus was also observed after the durability test and the match between the apparatus and each toner was evaluated. The results are shown in Table 22 together.

(Change in Image Density Within the Durability Limit)

Printing was done on a prescribed number of sheets of paper, ordinary plain paper for copying (75 g/m$^2$), and evaluation was made in terms of the degree to which the density of the printout image at the very beginning of printing was maintained by the printout image at the very end of printing. The image density was measured with a Macbeth reflection densitometer (manufactured by Macbeth) and the relative density of printout image on a white background with a copy density of 0.00 was measured and used for the evaluation.

AA: Excellent (image density at the very end of printing was 1.40 or more)
   A: Good (image density at the very end of printing was 1.35 or more and less than 1.40)
   B: Fair (image density at the very end of printing was 1.00 or more and less than 1.35)
   C: Bad (image density at the very end of printing was less than 1.00)

(Image Fog)

Printing was done on a prescribed number of sheets of paper, ordinary plain paper for copying (75 g/m$^2$), and evaluation was made in terms of the white solid image at the very end of printing. Specifically, the evaluation was made in the following manner. First the fog density was obtained from the following formula: (Ds-Dr), where Ds is the worst value of the reflection density on the white background portion after printing measured with a reflection densitometer (REFLECTOMETER ODEL TC-6DS by TOKYO DENSHOKU CO., LTD) and Dr is the mean value of the reflection density of the paper before printing. Then evaluation was made based on the following criteria.

AA: Very good (fog density was 0% or more and less than 1.5%)

A: Good (fog density was 1.5% or more and less than 3.0%)

B: Practically permissible (fog density was 3.0% or more and less than 5.0%)

C: Practically impermissible (fog density was 5.0% or more)

(Evaluation of Match Between Toner and Image Forming Apparatus)

1. Match between Toner and Developing Sleeve

After completing the printout tests, the retention of the residual toner on the surface of the developing sleeve and its effects on the printout image were visually observed and evaluated.

C: Practically impermissible (much retention occurred and defects occurred in the printout image in the form of vertical lines)

3. Match between Toner and Fixing Equipment

The state of the fixing film surface was observed, and the durability was evaluated through totaling and averaging the results of the surface quality and the retention of the residual toner.

(1) Surface Quality

After completing the printout tests, scratches and scrapes occurring on the surface of the fixing film were visually observed and evaluated.

AA: Very good (no scratches and scrapes occurred)

A: Good (almost no scratches and scrapes occurred)

B: Practically permissible

C: Practically impermissible (2) Retention of Residual Toner

After completing the printout tests, the retention of the residual toner on the surface of the film was visually observed and evaluated.

AA: Very good (no retention occurred)

A: Good (almost no retention occurred)

B: Practically permissible

C: Practically impermissible

TABLE 22

Evaluation of Printout Image and Match between Toner and Image Forming Apparatus

| | | Evaluation of Printout Image | | | | | Evaluation of Match between Toner and Equipment | | | |
| --- | --- | --- | --- | --- | --- | --- | --- | --- | --- | --- |
| | | Change in Image Density within the Durability Limit | | | | Image Fog | Developing Sleeve | Photosensitive Drum | Fixing Equipment | |
| | Toner | Initial Printout | 1000th Printout | 10,000th Printout | 30,000th Printout | 10,000th Printout | | | Surface Quality | Retention of Toner |
| Example | | | | | | | | | | |
| 72 | blue 1 | AA | AA | AA | A | AA | AA | AA | AA | AA |
| 73 | Yellow 1 | AA | AA | AA | A | AA | AA | AA | AA | AA |
| 74 | black 1 | AA | AA | AA | A | AA | AA | AA | AA | AA |
| Comparative Example | | | | | | | | | | |
| 13 | blue 15 | B | C | C | C | C | C | C | C | C |
| 14 | Yellow 15 | B | C | C | C | C | C | C | C | C |
| 15 | black 15 | A | B | C | C | C | C | C | C | C |

AA: Very good (no retention occurred)

A: Good (almost no retention occurred)

B: Practically permissible (retention occurred but did not affect the image)

C: Practically impermissible (a large amount of retention occurred and unevenness of image occurred)

2. Match between Toner and Photosensitive Drum

Scratches and retention of the toner occurring on the surface of the photosensitive drum as well as their effects on the printout image were visually observed and evaluated.

AA: Very good (no scratches and retention occurred)

A: Good (scratches and retention slightly occurred, but did not affect the printout image)

B: Practically permissible (scratches and retention occurred, but the effects on the printout image were small)

Example 75

Printout tests were conducted in the same manner as in the Example 72, except that the toner reuse mechanism was dismounted from the image forming apparatus of FIG. 6 and the print speed was set at 16 sheets of paper (A4 size) per minute, in a continuous mode (that is, a mode in which the consumption of toner is accelerated without stopping develop equipment) while supplying sequentially the blue toner (1) of the Example 20. The obtained images and the match between the toner and the used image forming apparatus were evaluated on the same items as those of the Examples 72 to 74 and of the Comparative Examples 13 to 15. The results were good for any of the items.

SEQUENCE LISTING

<160> NUMBER OF SEQ ID NOS: 1

<210> SEQ ID NO 1
<211> LENGTH: 1501
<212> TYPE: DNA
<213> ORGANISM: Pseudomonas jessenii 161 strain.

<400> SEQUENCE: 1

| | | | | | |
|---|---|---|---|---|---|
| tgaacgctgg | cggcaggcct | aacacatgca | agtcgagcgg | atgacgggag | cttgctcctg | 60 |
| aattcagcgg | cggacgggtg | agtaatgcct | aggaatctgc | ctggtagtgg | gggacaacgt | 120 |
| ctcgaaaggg | acgctaatac | cgcatacgtc | ctacgggaga | aagcagggga | ccttcgggcc | 180 |
| ttgcgctatc | agatgagcct | aggtcggatt | agctagttgg | tgaggtaatg | gctcaccaag | 240 |
| gcgacgatcc | gtaactggtc | tgagaggatg | atcagtcaca | ctggaactga | gacacggtcc | 300 |
| agactcctac | gggaggcagc | agtggggaat | attggacaat | gggcgaaagc | ctgatccagc | 360 |
| catgccgcgt | gtgtgaagaa | ggtcttcgga | ttgtaaagca | ctttaagttg | ggaggaaggg | 420 |
| cattaaccta | atacgttagt | gttttgacgt | taccgacaga | ataagcaccg | gctaactctg | 480 |
| tgccagcagc | cgcggtaata | cagagggtgc | aagcgttaat | cggaattact | gggcgtaaag | 540 |
| cgcgcgtagg | tggtttgtta | agttggatgt | gaaagcccccg | ggctcaacct | gggaactgca | 600 |
| ttcaaaactg | acaagctaga | gtatggtaga | gggtggtgga | atttcctgtg | tagcggtgaa | 660 |
| atgcgtagat | ataggaagga | acaccagtgg | cgaaggcgac | cacctggact | gatactgaca | 720 |
| ctgaggtgcg | aaagcgtggg | gagcaaacag | gattagatac | cctggtagtc | cacgccgtaa | 780 |
| acgatgtcaa | ctagccgttg | ggagccttga | gctcttagtg | gcgcagctaa | cgcattaagt | 840 |
| tgaccgcctg | gggagtacgg | ccgcaaggtt | aaaactcaaa | tgaattgacg | ggggcccgca | 900 |
| caagcggtgg | agcatgtggt | ttaattcgaa | gcaacgcgaa | gaaccttacc | aggccttgac | 960 |
| atccaatgaa | ctttccagag | atggatgggt | gccttcggga | acattgagac | aggtgctgca | 1020 |
| tggctgtcgt | cagctcgtgt | cgtgagatgt | tgggttaagt | cccgtaacga | gcgcaaccct | 1080 |
| tgtccttagt | taccagcacg | taatggtggg | cactctaagg | agactgccgg | tgacaaaccg | 1140 |
| gaggaaggtg | gggatgacgt | caagtcatca | tggcccttac | ggcctgggct | acacacgtgc | 1200 |
| tacaatggtc | ggtacagagg | gttgccaagc | cgcgaggtgg | agctaatccc | acaaaaccga | 1260 |
| tcgtagtccg | gatcgcagtc | tgcaactcga | ctgcgtgaag | tcggaatcgc | tagtaatcgc | 1320 |
| gaatcagaat | gtcgcggtga | atacgttccc | gggccttgta | cacaccgccc | gtcacaccat | 1380 |
| gggagtgggt | tgcaccagaa | gtagctagtc | taaccttcgg | gaggacggtt | accacggtgt | 1440 |
| gattcatgac | tggggtgaag | tcgtaccaag | gtagccgtag | gggaacctgc | ggctggatca | 1500 |
| c | | | | | | 1501 |

What is claimed is:

1. A polyhydroxyalkanoate having in the molecule a unit represented by Chemical Formula (1):

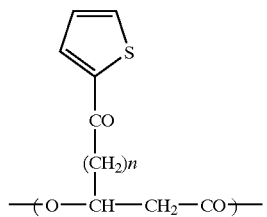

(1)

wherein n may assume any one integral value within the range of from 1 to 8.

2. The polyhydroxyalkanoate according to claim 1, which contains, in addition to the unit represented by Chemical Formula (1), at least one of units represented by Chemical Formulas (2) and (3):

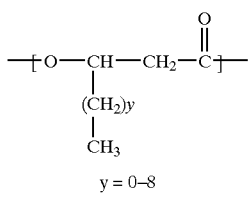

(2), y = 0–8

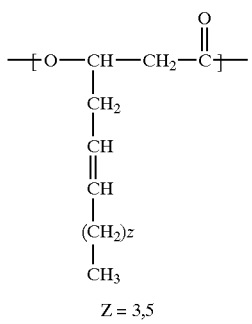

(3)

Z = 3,5 wherein y and z may assume any one integral value within the range shown in the chemical formulas, independently from the unit represented by Chemical Formula (1).

3. The polyhydroxyalkanoate according to claim 1, which has a number-average molecular weight in the range of from 1,000 to 500,000.

4. The polyhydroxyalkanoate according to claim 1, which contains as the unit represented by Chemical Formula (1) a unit represented by Chemical Formula (4):

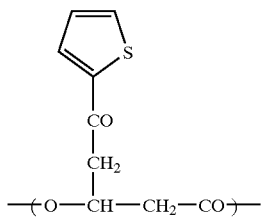

(4).

5. The polyhydroxyalkanoate according to claim 1, which contains as the unit represented by Chemical Formula (1) a unit represented by Chemical Formula (5):

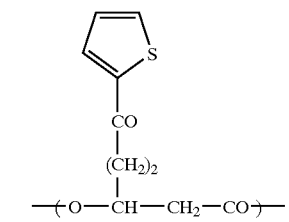

(5).

6. The polyhydroxyalkanoate according to claim 1, which contains as the unit represented by Chemical Formula (1) a unit represented by Chemical Formula (6):

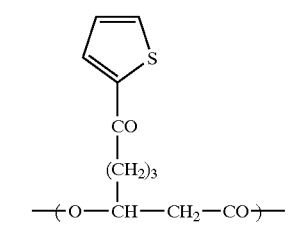

(6).

7. A process for producing a polyhydroxyalkanoate having in the molecule a unit represented by Chemical Formula (1):

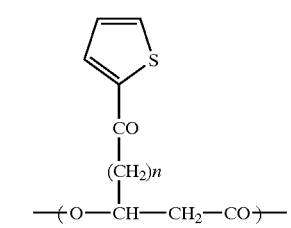

(1)

wherein n may assume any one integral value within the range of from 1 to 8, the process comprising culturing a microorganism in a culture medium containing at least one compound represented by Chemical Formula (7) or (8):

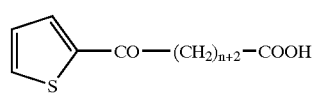

(7)

wherein n may assume any one integral value within the range of from 1 to 8,

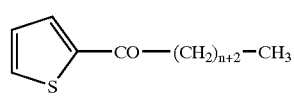

(8)

wherein n may assume any one integral value within the range of from 1 to 8.

8. The process according to claim 7 for producing the polyhydroxyalkanoate having in the molecule a unit represented by Chemical Formula (1):

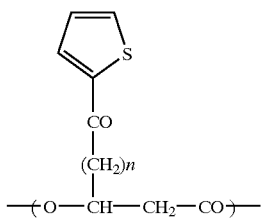

(1)

wherein n may assume any one integral value within the range of from 1 to 8, the process comprising culturing the microorganism in a culture medium containing at least one compound represented by Chemical Formula (7) or (8):

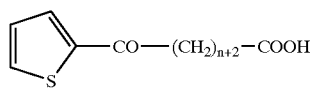

(7)

wherein n may assume any one integral value within the range of from 1 to 8,

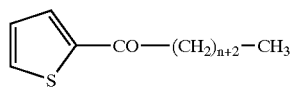

(8)

wherein n may assume any one integral value within the range of from 1 to 8, and polypeptone.

9. The process according to claim 7 for producing the polyhydroxyalkanoate having in the molecule a unit represented by Chemical Formula (1):

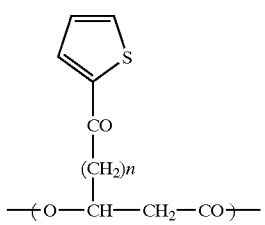

(1)

wherein n may assume any one integral value within the range of from 1 to 8, the process comprising culturing the microorganism in a culture medium containing at least one compound represented by Chemical Formula (7) or (8):

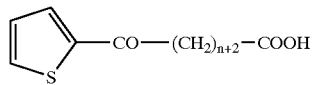

(7)

wherein n may assume any one integral value within the range of from 1 to 8,

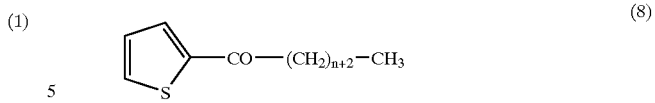

(8)

wherein n may assume any one integral value within the range of from 1 to 8, and yeast extract.

10. The process according to claim 7 for producing the polyhydroxyalkanoate having in the molecule a unit represented by Chemical Formula (1):

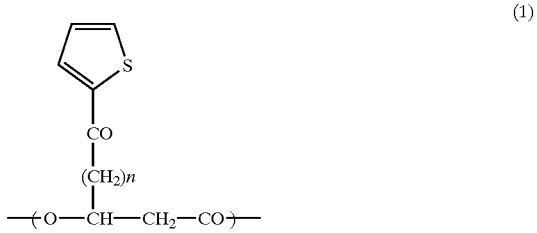

(1)

wherein n may assume any one integral value within the range of from 1 to 8, the process comprising culturing the microorganism in a culture medium containing at least one compound represented by Chemical Formula (7) or (8):

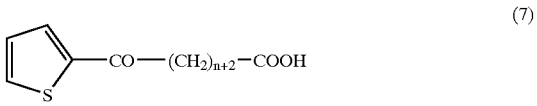

(7)

wherein n may assume any one integral value within the range of from 1 to 8,

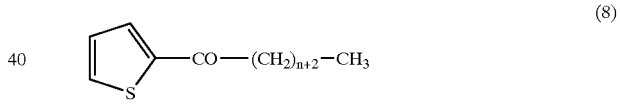

(8)

wherein n may assume any one integral value within the range of from 1 to 8, and a saccharide.

11. The process according to claim 10, wherein the saccharide is at least one compound selected from the group consisting of glyceraldehyde, erythrose, arabinose, xylose, glucose, galactose, mannose, fructose, glycerol, erythritol, xylitol, gluconic acid, glucuronic acid, galacturonic acid, maltose, sucrose and lactose.

12. The process according to claim 7 for producing the polyhydroxyalkanoate having in the molecule a unit represented by Chemical Formula (1):

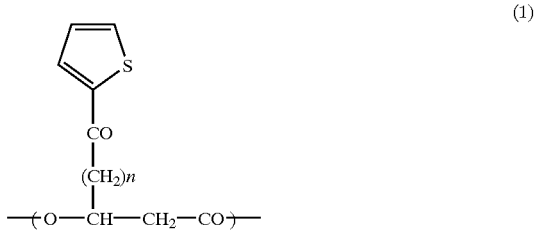

(1)

wherein n may assume any one integral value within the range of from 1 to 8, the process comprising culturing the microorganism in a culture medium containing at least one compound represented by Chemical Formula (7) or (8):

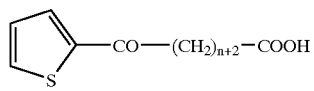  (7)

wherein n may assume any one integral value within the range of from 1 to 8,

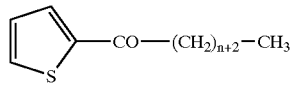  (8)

wherein n may assume any one integral value within the range of from 1 to 8, and an organic acid or a salt thereof.

13. The process according to claim 12, wherein the organic acid or the salt thereof is at least one compound selected from the group consisting of pyruvic acid, malic acid, lactic acid, citric acid and succinic acid and a salt of any of these.

14. The process according to claim 7 for producing the polyhydroxyalkanoate having in the molecule a unit represented by Chemical Formula (1):

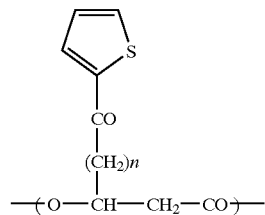  (1)

wherein n may assume any one integral value within the range of from 1 to 8, the process comprising culturing the microorganism in a culture medium containing at least one compound represented by Chemical Formula (7) or (8):

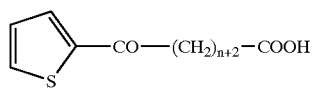  (7)

wherein n may assume any one integral value within the range of from 1 to 8,

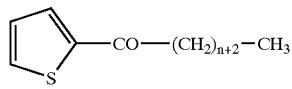  (8)

wherein n may assume any one integral value within the range of from 1 to 8, and an amino acid or a salt thereof.

15. The process according to claim 14, wherein the amino acid or the salt thereof is at least one compound selected from the group consisting of glutamic acid and aspartic acid and a salt of any of these.

16. The process according to claim 7 for producing the polyhydroxyalkanoate having in the molecule a unit represented by Chemical Formula (1):

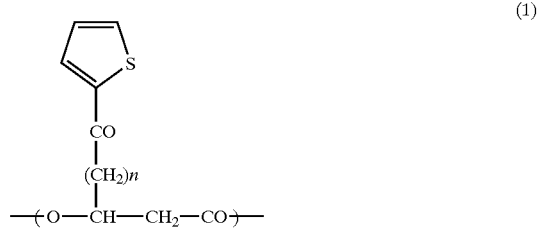  (1)

wherein n may assume any one integral value within the range of from 1 to 8, the process comprising culturing the microorganism in a culture medium containing at least one compound represented by Chemical Formula (7) or (8):

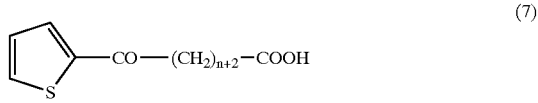  (7)

wherein n may assume any one integral value within the range of from 1 to 8,

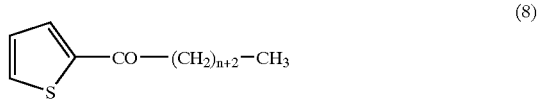  (8)

wherein n may assume any one integral value within the range of from 1 to 8, and a straight-chain alkanoic acid having 4 to 12 carbon atoms or a salt thereof.

17. The process according to claim 7 for producing the polyhydroxyalkanoate having in the molecule a unit represented by Chemical Formula (1):

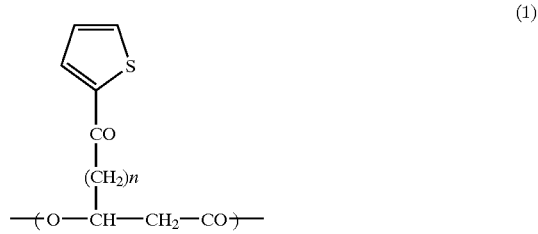  (1)

wherein n may assume any one integral value within the range of from 1 to 8, the process comprising the steps of:
(step 1-1) culturing a microorganism in a culture medium containing at least one compound represented by Chemical Formula (7) or (8):

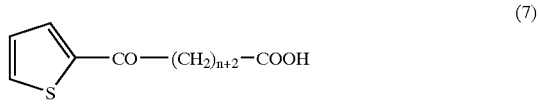  (7)

wherein n may assume any one integral value within the range of from 1 to 8,

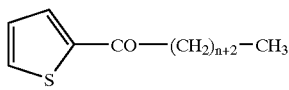 (8)

wherein n may assume any one integral value within the range of from 1 to 8, and containing polypeptone; and subsequently thereto (step 2-1) further culturing the microorganism cultured in the step 1-1, in a culture medium containing at least one compound represented by Chemical Formula (7) or (8) and an organic acid or a salt thereof.

18. The process according to claim 17, wherein the culture medium used in the step 2-1 does not contain any nitrogen source.

19. The process according to claim 17, wherein the organic acid or the salt thereof is at least one compound selected from the group consisting of pyruvic acid, malic acid, lactic acid, citric acid and succinic acid and a salt of any of these.

20. The process according to claim 7 for producing the polyhydroxyalkanoate having in the molecule a unit represented by Chemical Formula (1):

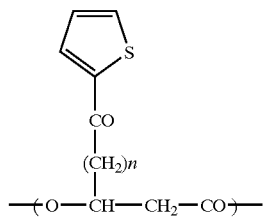 (1)

wherein n may assume any one integral value within the range of from 1 to 8, the process comprising the steps of:

(step 1-2) culturing a microorganism in a culture medium containing at least one compound represented by Chemical Formula (7) or (8):

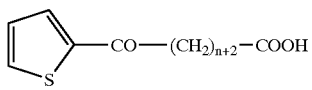 (7)

wherein n may assume any one integral value within the range of from 1 to 8,

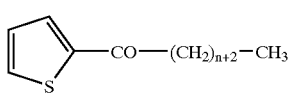 (8)

wherein n may assume any one integral value within the range of from 1 to 8, and containing a saccharide; and subsequently thereto (step 2-2) further culturing the microorganism cultured in the step 1-2, in a culture medium containing at least one compound represented by Chemical Formula (7) or (8) and containing a saccharide.

21. The process according to claim 20, wherein the culture medium used in the step 2-2 does not contain any nitrogen source.

22. The process according to claim 20, wherein the saccharide is at least one compound selected from the group consisting of glyceraldehyde, erythrose, arabinose, xylose, glucose, galactose, mannose, fructose, glycerol, erythritol, xylitol, gluconic acid, glucuronic acid, galacturonic acid, maltose, sucrose and lactose.

23. The process according to claim 7, wherein the polyhydroxyalkanoate contains, as a unit other than the unit represented by Chemical Formula (1), at least one of units represented by Chemical Formulas (2) and (3):

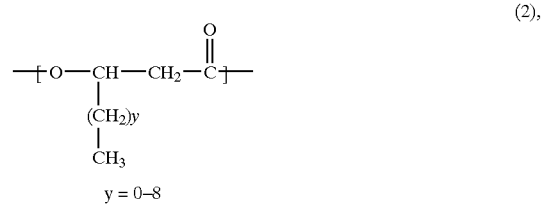 (2), $y = 0-8$

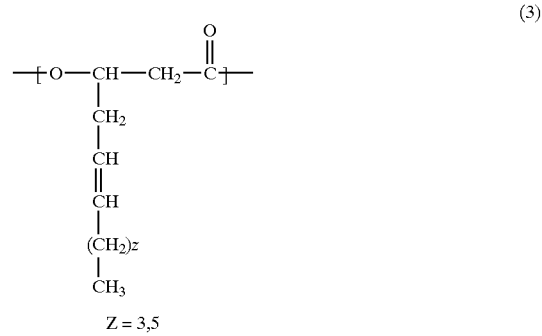 (3)

$Z = 3, 5$ wherein y and z may assume any one integral value within the range shown in the chemical formulas, independently from the unit represented by Chemical Formula (1).

24. The process according to claim 7, which is a process comprising culturing the microorganism in a culture medium containing 5-(2-thienoyl)valeric acid represented by Chemical Formula (9):

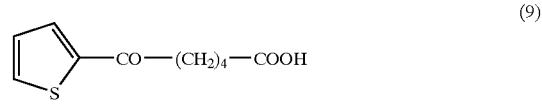 (9)

to produce a polyhydroxyalkanoate containing a unit represented by Chemical Formula (5):

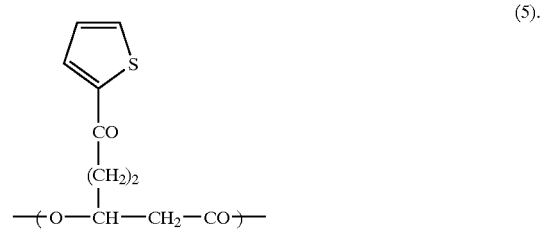 (5).

25. The process according to claim 7, which is a process comprising culturing the microorganism in a culture medium containing at least one 6-(2-thienoyl)hexanoic acid represented by Chemical Formula (10):

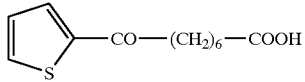
(10)

and 6-(2-thienoyl)hexane represented by Chemical Formula (11):

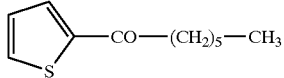
(11)

to produce a polyhydroxyalkanoate containing a unit represented by Chemical Formula (6):

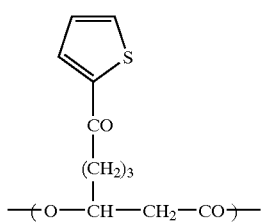
(6).

26. The process according to claim 7, wherein the microorganism is a microorganism belonging to the genus Pseudomonas.

27. The process according to claim 26, wherein the microorganism is a strain of at least one of *Pseudomonas cichorii* strain H45 (FERM BP-7374), *Pseudomonas cichorii* strain YN2 (FERM BP-7375) and *Pseudomonas jessenii* strain P161 (FERM BP-7376).

28. The process according to claim 7, which further comprises the step of collecting the polyhydroxyalkanoate from cells of the microorganism.

29. In a charge control agent composition for controlling the state of charge of a powder, the improvement which comprises a polyhydroxyalkanoate charge control agent having in the molecule at least one unit of units represented by Chemical Formula (1):

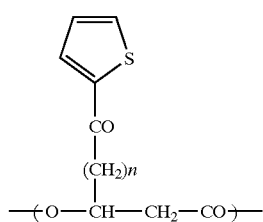
(1)

wherein n may assume any one integral value within the range of from 1 to 8.

30. The charge control agent composition according to claim 29, which contains, in addition to the unit represented by Chemical Formula (1), at least one of units represented by Chemical Formulas (2) and (3):

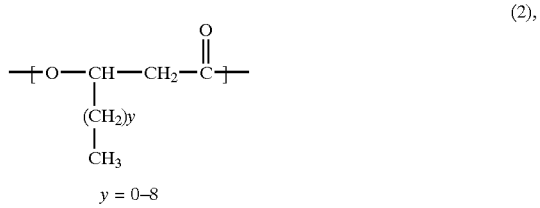
(2), $y = 0–8$

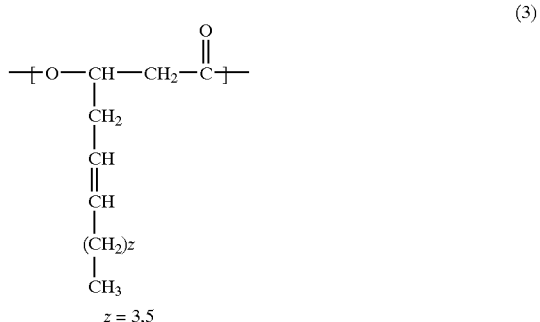
(3)

$z = 3, 5$ wherein y and z may assume any one integral value within the range shown in the chemical formulas, independently from the unit represented by Chemical Formula (1).

31. In a charge control agent composition for controlling the state of charge of a powder, the improvement which comprises a polyhydroxyalkanoate charge control agent having in the molecule at least one unit of units represented by Chemical Formula (12):

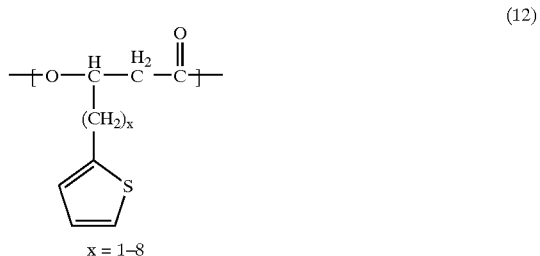
(12)

$x = 1–8$ wherein x may assume any one integral value within the range of from 1 to 8.

32. The charge control agent composition according to claim 31, which contains, in addition to the unit represented by Chemical Formula (12), at least one of units represented by Chemical Formulas (2) and (3):

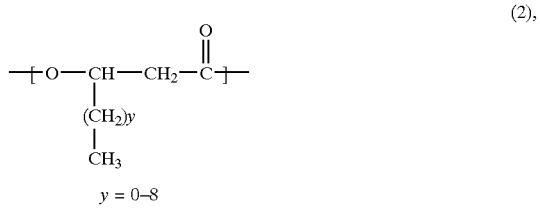
(2), $y = 0–8$

-continued

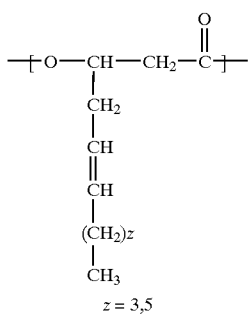

(3)

$z = 3,5$ wherein y and z may assume any one integral value within the range shown in the chemical formulas, independently from the unit represented by Chemical Formula (1).

33. The charge control agent composition according to claim 29, wherein the powder is a toner for developing electrostatic latent images.

34. The charge control agent composition according to claim 29, wherein the polyhydroxyalkanoate has a number-average molecular weight of from 1,000 to 500,000.

35. In a toner binder composition used in a toner for developing electrostatic latent images, the improvement which comprises the charge control agent according to claim 29.

36. A toner for developing electrostatic latent images, comprising a binder resin, a colorant and the charge control agent according to claim 29.

37. An image-forming method comprising:
a charging step of applying a voltage to a charging member from its outside to charge an electrostatic-latent-image-bearing member electrostatically;
a latent-image-forming step of forming an electrostatic latent image on the electrostatic-latent-image-bearing member thus charged;
a developing step of developing the electrostatic latent image by the use of a toner for developing electrostatic latent images, to form a toner image on the electrostatic-latent-image-bearing member;
a transfer step of transferring to a recording medium the toner image formed on the electrostatic-latent-image-bearing member; and
a heat fixing step of fixing by heat the toner image held on the recording medium;
wherein the toner for developing electrostatic latent images comprises a binder resin, a colorant and the charge control agent according to claim 29.

38. The image-forming method according to claim 37, which comprises:
a charging step of applying a voltage to a charging member from its outside to charge an electrostatic-latent-image-bearing member electrostatically;
a latent-image-forming step of forming an electrostatic latent image on the electrostatic-latent-image-bearing member thus charged;
a developing step of developing the electrostatic latent image by the use of a toner for developing electrostatic latent images, to form a toner image on the electrostatic-latent-image-bearing member;
a first transfer step of transferring to an intermediate transfer member the toner image formed on the electrostatic-latent-image-bearing member;
a second transfer step of transferring to a recording medium the toner image held on the intermediate transfer member; and
a heat fixing step of fixing by heat the toner image held on the recording medium;
wherein the toner for developing electrostatic latent images comprises a binder resin, a colorant and the charge control agent according to claim 29.

39. An image-forming apparatus comprising:
a charging means for applying a voltage to a charging member from its outside to charge an electrostatic-latent-image-bearing member electrostatically;
a latent-image-forming means for forming an electrostatic latent image on the electrostatic-latent-image-bearing member thus charged;
a developing means for developing the electrostatic latent image by the use of a toner for developing electrostatic latent images, to form a toner image on the electrostatic-latent-image-bearing member;
a transfer means for transferring to a recording medium the toner image formed on the electrostatic-latent-image-bearing member; and
a heat fixing means for fixing by heat the toner image held on the recording medium;
wherein the toner for developing electrostatic latent images comprises a binder resin, a colorant and the charge control agent according to claim 29.

40. The image-forming apparatus according to claim 39, which comprises:
a charging means for applying a voltage to a charging member from its outside to charge an electrostatic-latent-image-bearing member electrostatically;
a latent-image-forming means for forming an electrostatic latent image on the electrostatic-latent-image-bearing member thus charged;
a developing means for developing the electrostatic latent image by the use of a toner for developing electrostatic latent images, to form a toner image on the electrostatic-latent-image-bearing member;
a first transfer means for transferring to an intermediate transfer member the toner image formed on the electrostatic-latent-image-bearing member;
a second transfer means for transferring to a recording medium the toner image held on the intermediate transfer member; and
a heat fixing means for fixing by heat the toner image held on the recording medium;
wherein the toner for developing electrostatic latent images comprises a binder resin, a colorant and the charge control agent according to claim 29.

* * * * *

UNITED STATES PATENT AND TRADEMARK OFFICE
CERTIFICATE OF CORRECTION

PATENT NO. : 6,777,153 B2
DATED : August 17, 2004
INVENTOR(S) : Tetsuya Yano et al.

It is certified that error appears in the above-identified patent and that said Letters Patent is hereby corrected as shown below:

Title page,
Item [56], References Cited, OTHER PUBLICATIONS,
"Y.B. Kim et al.. ..." reference, "Groups" should read -- Group --; and
"B.A. Ramsay et al., ..." reference, "Poly-β-Hdroxylakanoate" should read
-- Poly-β-Hydroxylakanoate --.
Item [74], *Attorney, Agent or Firm*, "Fitzpatrick Cella Harper & Scinto" should read
-- Fitzpatrick, Cella, Harper & Scinto --.

Column 2,
Line 27, "ally" should read -- allyl --.

Column 3,
Line 58, "the" should be deleted.

Column 6,
Line 1, "disclose" should read -- discloses --.

Column 7,
Line 25, "which conditions" should read -- in which the condition --.

Column 8,
Line 16, "come" should de deleted; and
Line 32, "structure," should read -- structures, --.

Column 9,
Line 6, "images" should read -- images. --.

Column 10,
Lines 48-57,

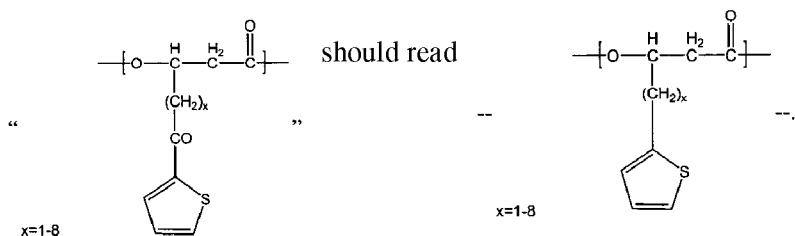

Column 12,
Line 15, "structure," should read -- structures, --; and
Line 25, "And" should read -- and --.

Column 14,
Line 38, "pre-culuring," should read -- pre-culturing, --; and
Line 52, "the" (second occurrence) should be deleted.

UNITED STATES PATENT AND TRADEMARK OFFICE
CERTIFICATE OF CORRECTION

PATENT NO. : 6,777,153 B2  Page 2 of 7
DATED : August 17, 2004
INVENTOR(S) : Tetsuya Yano et al.

It is certified that error appears in the above-identified patent and that said Letters Patent is hereby corrected as shown below:

Columns 15 and 16,

"
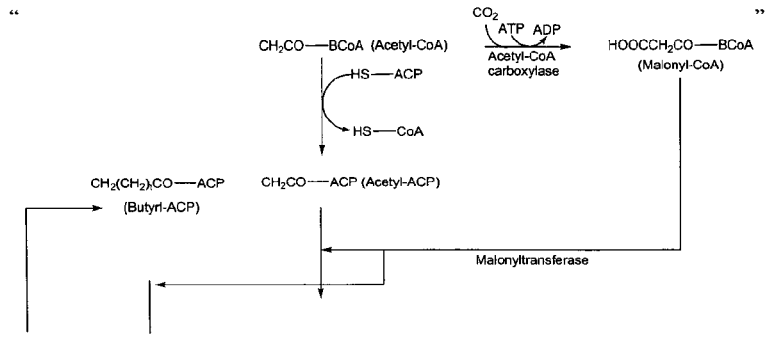

should read

--
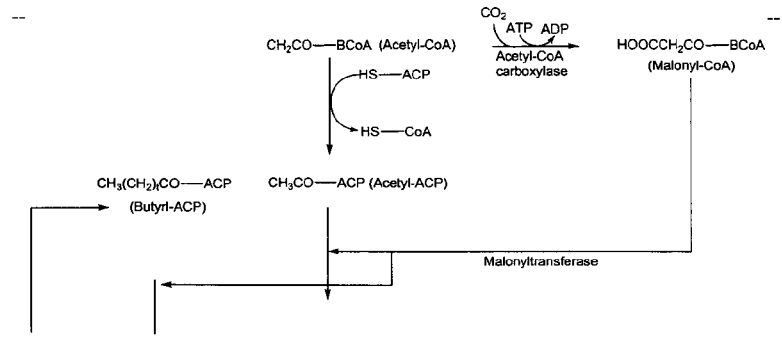
--.

Columns 17 and 18,

"
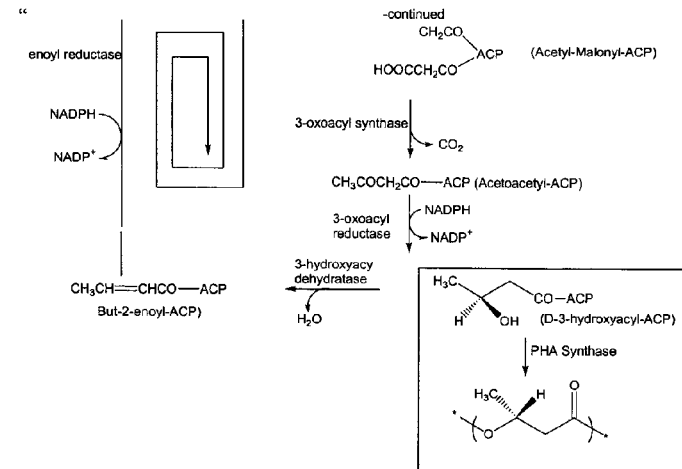
"

UNITED STATES PATENT AND TRADEMARK OFFICE
CERTIFICATE OF CORRECTION

PATENT NO.    : 6,777,153 B2
DATED         : August 17, 2004
INVENTOR(S)   : Tetsuya Yano et al.

It is certified that error appears in the above-identified patent and that said Letters Patent is hereby corrected as shown below:

Columns 17 and 18 (cont'd),
should read

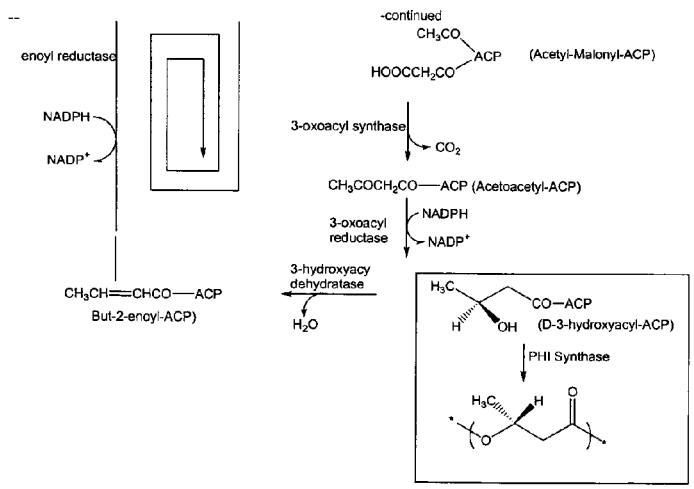

Column 18,
Lines 34 and 37, "the" should be deleted.

Column 19,
Line 45, "to" should read -- in --; and
Line 50, "use." should read -- used. --.

Column 20,
Line 36, "periphery" should read -- periphery, --; and
Line 57, "Accumulation of poly-β-hydroxybutyric acid: negative." should be deleted.

Column 21,
Line 19, "periphery" should read -- periphery, --; and
Line 62, "diameter." should read -- diameter, --.

Column 22,
Line 3, "periphery" should read -- periphery, --; and
Line 67, "along" should read -- long --.

Column 23,
Line 20, "meet" should read -- meat --;
Line 22, "to" should read -- in --;
Line 30, "use." should read -- used. --; and
Line 47, "leas" should read -- least --.

UNITED STATES PATENT AND TRADEMARK OFFICE
CERTIFICATE OF CORRECTION

PATENT NO. : 6,777,153 B2
DATED : August 17, 2004
INVENTOR(S) : Tetsuya Yano et al.

It is certified that error appears in the above-identified patent and that said Letters Patent is hereby corrected as shown below:

Column 24,
Line 61, "to" should read -- in --.

Column 26,
Lines 40-63, 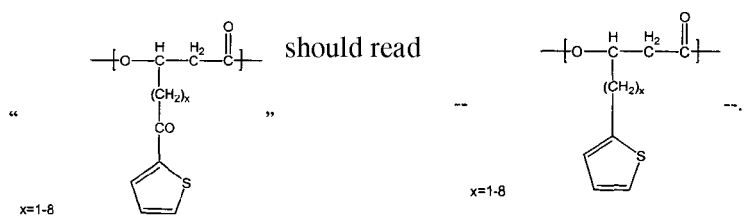

Column 30,
Line 35, "p-ethylstyrenee," should read -- p-ethylstyrene, --.

Column 31,
Line 31, "methacyloxypolyethoxyphenyl)propane," should read
-- methacryloxypolyethoxyphenyl)propane, --; and
Line 32, "triallyl asocyanurate" should be deleted.

Column 34,
Line 48, "optionally" should read -- optional --;

Column 35,
Line 50, "300 pin," should read -- 300 $\mu$m, --; and
Line 55, "coated." should read -- coat. --.

Column 36,
Line 3, "material" should read -- materials --; and
Line 65, "quantity" (second occurrence) should be deleted.

Column 37,
Line 54, "A-807, available" should read -- A-807 (available --; and
Line 55, "Denko K.K.," should read -- Denko K.K. --.

Column 38,
Line 16, "to;" should read -- to: --.

Column 47,
Line 41, "Ltd)" should read -- Ltd.) --.

Column 48,
Line 11, "shaked" should read -- shaken --.

UNITED STATES PATENT AND TRADEMARK OFFICE
CERTIFICATE OF CORRECTION

PATENT NO. : 6,777,153 B2
DATED : August 17, 2004
INVENTOR(S) : Tetsuya Yano et al.

It is certified that error appears in the above-identified patent and that said Letters Patent is hereby corrected as shown below:

Column 49,
Lines 11 and 47, "treatment" should read -- treatments --.

Column 50,
Line 19, "treatment" should read -- treatments --; and
Line 64, "then the polymerizable monomer composition" should be deleted.

Column 51,
Line 60, "a" should be deleted.

Column 52,
Line 11, "obatained" should read -- obtained --; and
Line 12, "agitation" should read -- agitations --.

Column 53,
Line 17, "agitation" should read -- agitations --.

Column 54,
Line 24, "agitation" should read -- agitations --.

Column 56,
Line 27, "a" should be deleted; and
Line 47, "agitation" should read -- agitations --.

Column 58,
Line 32, "agitation" should read -- agitations --.

Column 59,
Line 59, "Example" should read -- Examples --.

Column 60,
Line 23, "a" should be deleted; and
Line 49, "agitation" should read -- agitations --.

Column 62,
Line 37, "degree" should read -- degrees --.

Column 64,
Line 44, "was" should read -- were --; and
Line 45, "arouse" should read -- arose --.

UNITED STATES PATENT AND TRADEMARK OFFICE
CERTIFICATE OF CORRECTION

PATENT NO. : 6,777,153 B2
DATED : August 17, 2004
INVENTOR(S) : Tetsuya Yano et al.

It is certified that error appears in the above-identified patent and that said Letters Patent is hereby corrected as shown below:

Column 65,
Table 21,

"

| Two-component Developer | Evaluation of Printout Image | | | | | |
|---|---|---|---|---|---|---|
| | Normal Temperature and Humidity | | | High Temperature and Humidity | | |
| | Image Density | Image Fog | Transfer Properties | Image Density | Image Fog | Transfer Properties |
| 66 red 1 | AA | AA | AA | A | AA | A |

"

should read

--

| Two-component Developer | Evaluation of Printout Image | | | | | |
|---|---|---|---|---|---|---|
| | Normal Temperature and Humidity | | | High Temperature and Humidity | | |
| | Image Density | Image Fog | Transfer Properties | Image Density | Image Fog | Transfer Properties |
| Example | | | | | | |
| 66 red 1 | AA | AA | AA | A | AA | A |

--; and

Line 14, "Co. Ex" should read -- Co. Ex. --;
Line 22, "Co. Ex" should read -- Co. Ex. --; and
Line 42, "reuse 23," should read -- recycler 23 --.

Column 67,
Line 8, "LTD)" should read -- LTD.) --.

Column 71,
Line 41, "Z = 2,5" should read -- z = 3,5 --.

Column 78,
Line 33, "Z = 3,5" should read -- z = 3,5 --.

UNITED STATES PATENT AND TRADEMARK OFFICE
CERTIFICATE OF CORRECTION

PATENT NO. : 6,777,153 B2
DATED : August 17, 2004
INVENTOR(S) : Tetsuya Yano et al.

It is certified that error appears in the above-identified patent and that said Letters Patent is hereby corrected as shown below:

Column 79,
Line 8, " 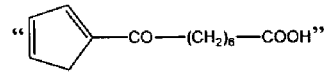 " should read -- 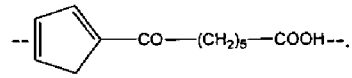 --.

Signed and Sealed this

Eighteenth Day of January, 2005

JON W. DUDAS
*Director of the United States Patent and Trademark Office*